United States Patent [19]

Schilling et al.

[11] Patent Number: 5,310,743
[45] Date of Patent: May 10, 1994

[54] 1-ACYLPIPERIDINE COMPOUNDS

[75] Inventors: Walter Schilling, Himmelried; Silvio Ofner, Münchenstein; Siem J. Veenstra, Basel, all of Switzerland

[73] Assignee: Ciba-Geigy Corp., Ardsley, N.Y.

[21] Appl. No.: 929,186

[22] Filed: Aug. 11, 1992

[30] Foreign Application Priority Data

Dec. 8, 1991 [CH] Switzerland .................. 2374/91

[51] Int. Cl.$^5$ ............... C07D 215/12; C07D 215/16; A01N 43/42
[52] U.S. Cl. .................. 514/311; 514/312; 514/314; 546/153; 546/155; 546/156; 546/168; 546/174; 546/175; 546/176; 546/177
[58] Field of Search ........... 546/192, 196, 207, 208, 546/209, 174, 175, 176, 195, 198, 153, 155, 156, 166, 177; 514/311, 312, 314

[56] References Cited

U.S. PATENT DOCUMENTS 5,126,455  6/1992  Feldman et al. .................. 546/223
5,145,967  9/1992  Lin et al. ........................... 546/223

FOREIGN PATENT DOCUMENTS 428434  5/1991
429366  5/1991  European Pat. Off.
9005525  5/1990  PCT Int'l Appl.
9118878  12/1991  PCT Int'l Appl.
9118899  12/1991  PCT Int'l Appl.
9206079  4/1992  PCT Int'l Appl.

OTHER PUBLICATIONS

Garret et al, Proc. Natl. Acad. Sci. USA 88, 10208–10212, Nov. 1991 Pharmacological Properties of a Patent and Selective Nonpeptide Substance P Antagoni.
Snider et al, Science 251, 435–437, Jan. 25, 1991. A Potent Nonpeptide Antagonist of the Substance P (NK) Receptor.
McLean et al, Science 251, 437–439, Jan. 25, 1991. Activity and Distribution of Binding Sites in Brain of a Nonpeptide Substance P (NK) Receptor Antagoni.
Chem. Abst. 68:38700v (1968) Becker et al.
Chem. Abst. 63:11494c (1965) Becker et al.
Chem. Abst. 56: 7263i (1961) Becker et al.
Watling, Tips vol. 13, pp. 266–269, Jul. 1992 Nonpeptide Antagonists Herald New Era in Tachykin in Research.

Primary Examiner—C. Warren Ivy
Assistant Examiner—Raymond Covington
Attorney, Agent, or Firm—Irving M. Fishman; Karen G. Kaiser

[57]  ABSTRACT

1-Acylpiperidine compound of the formula I

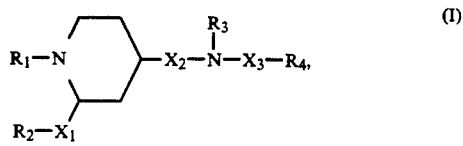

in which $R_1$ is an optionally substituted aralkyl, aryloxyalkyl, heteroaralkyl, aroyl, heteroaroyl, cycloalkylcarbonyl, aralkanoyl, heteroarylalkanoyl, aralkoxycarbonyl or arylcarbamoyl radical or the acyl radical of an α-amino acid which is optionally N-substituted by lower alkanoyl or carbamoyl-lower-alkanoyl, $R_2$ is cycloalkyl or an optionally substituted aryl or heteroaryl radical, $R_3$ is hydrogen, alkyl, carbamoyl or an alkanoyl or alkenoyl radical which is optionally substituted by carboxyl or esterified or amidated carboxyl, $R_4$ is an optionally substituted aryl or optionally partially hydrogenated heteroaryl radical, $X_1$ is methylene, ethylene, a direct linkage, an optionally ketalised carbonyl group or an optionally etherified hydroxymethylene group, $X_2$ is alkylene, carbonyl or a direct linkage, and $X_3$ is carbonyl, oxo-lower-alkylene, oxo(aza)-loweralkylene or an alkylene radical which is optionally substituted by phenyl, hydroxymethyl, optionally esterified or amidated carboxyl or, in higher than the α position, by hydroxyl, and its salts have substance-P-antagonistic properties and can be used as pharmaceutically active substances in pharmaceuticals for the treatment of disorders in whose development substance P plays an essential part.

10 Claims, No Drawings

1-ACYLPIPERIDINE COMPOUNDS

The invention relates to novel 1-acrylpiperidine compounds of the formula I

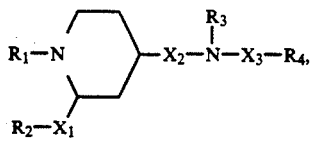

in which $R_1$ is an optionally substituted aralkyl, aryloxyalkyl, heteroaralkyl, aroyl, heteroaroyl, cycloalkylcarbonyl, aralkanoyl, heteroarylalkanoyl, aralkoxycarbonyl or arylcarbamoyl radical or the acyl radical of an α-amino acid which is optionally N-substituted by lower alkanoyl or carbamoyl-lower-alkanoyl, $R_2$ is cycloalkyl or an optionally substituted aryl or heteroaryl radical, $R_3$ is hydrogen, alkyl, carbamoyl or an alkanoyl or alkenoyl radical which is optionally substituted by carboxyl or esterified or amidated carboxyl, $R_4$ is an optionally substituted aryl or optionally partially hydrogenated heteroaryl radical, $X_1$ is methylene, ethylene, a direct linkage, an optionally ketalised carbonyl group or an optionally etherified hydroxymethylene group, $X_2$ is alkylene, carbonyl or a direct linkage, and $X_3$ is carbonyl, oxo-lower-alkylene, oxo(aza)-lower-alkylene or an alkylene radical which is optionally substituted by phenyl, hydroxymethyl, optionally esterified or amidated carboxyl or, in higher than the α position, by hydroxyl and their salts, to process for the preparation of the compounds according to the invention, to pharmaceutical products containing these, and to their use as pharmaceutically active substances.

The said aryl, aroyl, aralkanoyl, heteroaryl and heteroaroyl radicals can be unsubstituted or substituted, such as mono-, di- or trisubstituted, in particular mono- or disubstituted, for example by aromatically bonded lower alkyl, lower alkoxy, halogen and/or trifluoromethyl. Aryl, aralkyl, aryloxyalkyl, cycloalkylcarbonyl and aroyl radicals are preferably mono- or disubstituted, such as 3-mono- or 3,5-disubstituted, in the stated manner; heteroaryl, heteroaralkyl, heteroaralkanoyl and heteroaroyl radicals are preferably unsubstituted. Aralkyl is, for example, phenyl- or diphenyl-lower-alkyl which is optionally substituted in the phenyl or naphthyl moiety.

Aryloxy-lower-alkyl is, for example, phenoxy-lower-alkyl which is optionally substituted in the phenyl moiety.

Heteroalkyl is, for example, heteroaryl-lower-alkyl which has as heteroaryl radical aza-heteroaryl which is 6-membered and monocyclic or is bicyclic and composed of a 6-membered and a 5- or 6-membered ring.

Aroyl is, for example, optionally substituted benzoyl such as benzoyl, 3-lower-alkyl-, 3-lower-alkoxy-, 3-halogeno-, 3-dimethylamino-, 3,5-di-lower-alkyl, 3,5-di-lower-alkoxy-, 3,5-dihalogeno- or 3,5-ditrifluoromethylbenzoyl, or secondarily optionally substituted naphthoyl such as 1- or 2-naphthoyl or fluorenoyl.

Heteroaroyl is, for example, aza-heteroaroyl which is 6-membered and monocyclic or is bicyclic and composed of a 6-membered and a 5- or 6-membered ring, such as pyridylcarbonyl or quinolinylcarbonyl.

Cycloalkylcarbonyl is, for example, optionally substituted 3- to 8-, in particular 5- to 7-membered, cycloalkylcarbonyl such as cyclohexylcarbonyl, 3-lower-alkyl-, 3-lower-alkoxy-, 3-halogeno-, 3-dimethylamino-, 3,5-di-lower-alkyl, 3,5-di-lower-alkoxy-, 3,5-dihalogeno- or 3,5-ditrifluoromethylcyclohexylcarbonyl.

Aralkanoyl means, for example, phenyl- or diphenyl-lower-alkanoyl which is optionally substituted in the phenyl moiety.

Heteroarylalkanoyl is, for example, heteroaryl-lower-alkanoyl which has as heteroaryl radical aza-heteroaryl which is 6-membered and monocyclic or is bicyclic and composed of a 6-membered and a 5- or 6-membered ring.

Arylcarbamoyl means, for example, N-phenylcarbamoyl which is unsubstituted or optionally substituted in the phenyl moiety.

Acyl radicals of optionally N-alkanoylated α-amino acids are derived, in particular, from α-amino acids which occur in nature as building blocks of peptides and are optionally lower-alkanoylated, for example N—C-2–$C_7$alkanoylated, such as substituted by acetyl, propionyl, butyryl or pivaloyl. Examples are groups of the formula

in which $R_5$ is hydrogen, or a lower alkyl radical which is optionally substituted by hydroxyl, amino, mercapto, optionally hydroxyl-substituted phenyl, carboxyl, carbamoyl or ureido, such as $C_1$–$C_4$alkyl radical, for example methyl, isopropyl, isobutyl, secondary butyl, hydroxymethyl, mercaptomethyl, 2-methylmercaptoethyl, 3-ureidopropyl, 4-aminobutyl, carboxymethyl, carbamoylmethyl, 2-carboxyethyl, 2-carbamoylethyl, benzyl or 4-hydroxybenzyl, and $R_6$ is lower alkanoyl, for example $C_2$–$C_7$alkanyol, such as acetyl, propionyl, butyryl or pivaloyl. However, it can also be the acryl group of a heterocyclic α-amino acid which occurs naturally as building blocks of peptides, such as prolyl, tryptophanyl or histidinyl.

Cycloalkyl is, for example, 5- to 7-membered cycloalkyl such as, in particular, cyclohexyl or secondarily cyclopentyl or cycloheptyl.

Aryl is, for example, phenyl or, in particular as $R_4$, naphthyl.

Heteroaryl is, for example, 6-membered monocyclic aza-heteroaryl such as pyridyl, or, as $R_4$ in particular heteroaryl which is composed of an optionally partially hydrogenated 5- or 6-membered mono- or diaza- or oxa-heteroaryl radical and of a 6-membered aryl radical, such as benzofuranyl, for example benzofuran-2-yl or -3-yl, indolyl, for example indol-2-yl or -3-yl, 2,3-dihydroindolyl, for example 2,3-dihydroindol-2-yl or -3-yl, benzimidazolyl, for example benzimidazol-2-yl, quinolyl, for example quinolin-4-yl, or 1,2,3,4-tetrahydroquinolin-4-yl.

As heteroaryl radical of heteroaryl-lower-alkanoyl which has aza-heteroaryl which is 6-membered and monocyclic or is bicyclic and composed of a 6-membered and 5- or 6-membered ring is, for example, corresponding heteroaryl-$C_1$–$C_4$alkanoyl, such as 2-pyridyl- or4-pyridylacetyl, 2,3,4,9-tetrahydro-1H-pyrido[3,4-b]indol-3-ylcarbonyl.

Alkyl is, in particular, lower alkyl; alkylene in particular lower alkylene.

Ketalised carbonyl groups are, for example, ketalised with an aliphatic alcohol or a dialcohol such as with a lower alkanol or a lower alkanediol and are, for example, di-lower-alkoxymethylene or lower alkylenedioxymethylene.

Etherified hydroxymethylene is, in particular, etherified with an aliphatic alcohol such as a lower alkanol and is, for example, lower alkoxymethylene.

Optionally esterified or amidated carboxyl is, for example, carboxyl, lower alkoxycarbonyl, carbamoyl or N-mono- or N,N-di-lower-alkylcarbamoyl.

Alkanoyl or alkenoyl radicals which are optionally substituted by carboxyl or esterified or amidated carboxyl are, for example, lower alkanoyl such as $C_2$–$C_7$alkanoyl such as acetyl, propionyl, butyryl or pivaloyl, carboxy-lower-alkanoyl such as carboxy-$C_3$–$C_7$alkanoyl such as succinoyl, glutaroyl or adipoyl, or carboxy-lower-alkenoyl such as carboxy-$C_1$–$C_5$alkenoyl such as maleyl, fumaroyl or tartroyl, in which carboxyl can also be esterified or amidated, and, for example, lower alkoxycarbonyl such as $C_1$–$C_4$alkoxycarbonyl, for example methoxy- or ethoxycarbonyl, carbamoyl or N-mono- or N,N-di-lower-alkylcarbamoyl such as N-mono- or N,N-di-$C_1$–$C_4$alkylcarbamoyl, for example N-methyl- or N,N-dimethylcarbamoyl.

Lower alkylene substituted in higher than the α position by hydroxyl is, for example, hydroxylated in position 2 with respect to the N atom.

Lower alkylene substituted by hydroxymethyl or optionally esterified or amidated carboxyl is, for example, substituted in position 1, 2 or, where present, 3 with respect to the N atom by carboxyl, lower alkoxycarbonyl, carbamoyl, N-mono- or N,N-di-lower-alkylcarbamoyl or hydroxymethyl.

Hereinbefore and hereinafter lower radicals and compounds are to be understood to be, for example, those which have up to and including 7, preferably up to and including 4, carbon atoms (C atoms).

Lower alkyl is, for example, $C_1$–$C_7$alkyl, preferably $C_1$–$C_4$alkyl, such as, in particular, methyl or secondarily ethyl, propyl, isopropyl or butyl, but can also be isobutyl, secondary butyl, tertiary butyl or a $C_5$–$C_7$alkyl such as pentyl, hexyl or heptyl group.

Lower alkylene is, for example, $C_1$–$C_7$alkylene, preferably $C_1$–$C_4$alkylene such as methylene, ethylene, 1,3-propylene, 1,4-butylene or 1,5-pentylene.

Phenyl or diphenyl-lower-alkyl which is optionally substituted in the phenyl is, for example, corresponding phenyl- or diphenyl-$C_1$–$C_4$alkyl such as benzyl, 2,4-dichlorobenzyl, 3,5-ditrifluoromethylbenzyl, 2-phenylethyl or 2,2-diphenylethyl.

Phenyl- or diphenyl-lower-alkanoyl which is optionally substituted in the phenyl moiety is, for example, corresponding phenyl- or diphenyl-$C_1$–$C_4$alkanoyl such as 2,2-diphenylacetyl or 2,3-diphenylpropionyl.

Phenoxy-lower-alkyl which is optionally substituted in the phenyl is, for example, phenoxy-$C_1$–$C_4$alkyl which is substituted by halogen and/or triazolyl, such as 2-[2-(1H-1,2,4-triazol-1-yl)-4-chlorophenoxy]ethyl.

As heteroaryl radical of heteroaryl-lower-alkyl which has aza-heteroaryl which is 6-membered and monocyclic or is bicyclic and composed of a 6-membered and a 5- or 6-membered ring is, for example, pyridyl- or quinolinyl-$C_1$–$C_4$alkyl such as 4-quinolinylmethyl.

Lower alkoxy is, for example, $C_1$–$C_7$alkoxy, preferably $C_1$–$C_4$alkoxy, such as methoxy, ethoxy, propyloxy, isopropyloxy or butyloxy, but can also be isobutyloxy, secondary butyloxy, tertiary butyloxy or a pentyloxy, hexyloxy or heptyloxy group.

Halogen is, for example, halogen of atomic number up to and including 35, such as chlorine or fluorine, furthermore bromine.

Lower alkoxycarbonyl is, for example, $C_1$–$C_7$alkoxycarbonyl, preferably $C_1$–$C_4$alkoxycarbonyl, such as methoxycarbonyl, ethoxycarbonyl, propyloxycarbonyl, isopropyloxycarbonyl or butyloxycarbonyl, but can also be isobutyloxycarbonyl, secondary butyloxycarbonyl, tertiary butyloxycarbonyl or a pentyloxycarbonyl, hexyloxycarbonyl or heptyloxycarbonyl group.

N-lower-alkylcarbamoyl is, for example, N—$C_1$–$C_7$alkylcarbamoyl, preferably N—$C_1$–$C_4$alkylcarbamoyl, such as methylcarbamoyl, ethylcarbamoyl, propylcarbamoyl, isopropylcarbamoyl or butylcarbamoyl, but can also be isobutylcarbamoyl, secondary butylcarbamoyl, tertiary butylcarbamoyl or a pentylcarbamoyl, hexylcarbamoyl or heptylcarbamoyl group.

N,N-di-lower-alkylcarbamoyl is, for example, N,N-di-$C_1$–$C_7$alkylcarbamoyl, preferably N,N-di-$C_1$–$C_4$alkylcarbamoyl, such as N,N-dimethylcarbamoyl, N,N-diethylcarbamoyl, N-ethyl-N methylcarbamoyl, N,N-dipropylcarbamoyl, N-methyl-N-propylcarbamoyl, N-isopropyl-N-methylcarbamoyl or N-butyl-N-methylcarbamoyl, but can also be N-isobutyl-N-methylcarbamoyl, N-methyl-N-secondary butylcarbamoyl, N-methyl-N-tertiary butylcarbamoyl or a N-methyl-N-pentylcarbamoyl, N-hexyl-N-methylcarbamoyl or N-heptyl-N-methylcarbamoyl group.

Lower alkylene which is substituted in higher than the α position and in lower than the ω position by hydroxyl is, for example, 1,3-(2-hydroxy)propylene, 1,4-(2-hydroxy)butylene, 1,4-(3-hydroxy)butylene, 1,5-(2-hydroxy)pentylene 1,5-(3-hydroxy)pentylene or 1,5-(4-hydroxy)pentylene.

Lower alkylene substituted by carboxyl is, for example, carboxymethylene, 1- or 2-carboxyethylene, 1,3-(2-carboxy)propylene, 1,4-(2-carboxy)butylene, 1,4-(3-carboxy)butylene, 1,5-(2-carboxy)pentylene 1,5-(3-carboxy)pentylene or 1,5-(4-carboxy)pentylene.

Lower alkylene substituted by lower alkoxycarbonyl is, for example, lower alkoxycarbonylmethylene, 1- or 2-lower-alkoxycarbonylethylene, 1,3-(2-lower-alkoxycarbonyl)propylene, 1,4-(2-lower-alkoxycarbonyl)butylene, 1,4-(3-lower-alkoxycarbonyl)butylene, 1,5-(2-lower-alkoxycarbonyl)pentylene 1,5-(3-lower-alkoxycarbonyl)pentylene or 1,5-(4-lower-alkoxycarbonyl)pentylene, where lower alkoxycarbonyl means in each case, for example, $C_1$–$C_4$alkocycarbonyl, such as methoxycarbonyl, ethoxycarbonyl, propoxycarbonyl or butoxycarbonyl.

Lower alkylene substituted by carbamoyl, N-mono- or N,N-di-lower-alkylcarbamoyl is, in particular, substituted by carbamoyl and means, for example, carbamoylmethylene, 1- or 2-carbamoylethylene, 1,3-(2-carbamoyl)propylene, 1,4-(2-carbamoyl)butylene, 1,4-(3-carbamoyl)butylene, 1,5-(2-carbamoyl)pentylene, 1,5-(3-carbamoyl)pentylene or 1,5-(4-carbamoyl)pentylene.

Lower alkylene substituted by hydroxymethyl is, for example, 2-hydoxyethylidene, 2,3-(1-hydroxy)propyl 1,3-(2-hydroxymethyl)propylene, 2,4-(1-hydroxy)butylene, 1,4-(2-hydroxymethyl)butylene, 1,4-(3-hydroxymethyl)butylene, 1,5-(2-hydroxymethyl)pentylene 1,5-(3-hydroxymethyl)pentylene or 1,5-(4-hydroxymethyl)pentylene.

Lower alkoxymethylene is, for example, $C_1$–$C_4$alkoxymethylene such as methoxymethylene, ethoxymethylene, propyloxymethylene or butyloxymethylene.

Di-lower-alkoxymethylene is, for example, di-$C_1$–$C_4$alkoxymethylene such as dimethoxymethylene, diethoxymethylene, dipropyloxymethylene or dibutyloxymethylene.

Lower alkylenedioxymethylene is, for example, 5- to 8-membered, in particular 5- or 6-membered 1,3-dioxacycloalk-2-yl, such as 1,3-dioxacyclobut-2-yl, 1,3-dioxacyclopent-2-yl (1,3-dioxolan-2-yl), 1,3-dioxacyclohex-2-yl (1,3-dioxan-2-yl) or 1,3-dioxacyclohept-2-yl.

The compounds of the formula I have basic or, where $R_3$ and/or $X_3$ is substituted by carboxyl, amphoteric characteristics and can accordingly form acid addition salts and, where appropriate, inner salts.

Acid addition salts of compounds of the formula I are, for example, their pharmaceutically utilisable salts with suitable mineral acids such as hydrohalic acids, sulfuric acid or phosphoric acid, for example hydrochlorides, hydrobromides, sulfates, hydrogensulfates or phosphates, or salts with suitable aliphatic or aromatic sulfonic acids or N-substituted sulfamic acids, for example methanesulfonates, benzenesulfonates, p-toluenesulfonates or N-cyclohexylsulfamates (cyclamates).

It is also possible to use pharmaceutically unsuitable salts for isolation or purification. Only the pharmaceutically utilisable non-toxic salts are used therapeutically and they are therefore preferred.

The compounds prepared according to the invention have valuable pharmacological properties. In particular, they show a pronounced antagonistic action against substance P and display the spectrum of properties typical of substance P antagonists. Thus, the compounds of the formula I and their pharmaceutically utilisable salts completely inhibit in vitro the binding of $^3$H-substance P to the bovine retina in the radioreceptor assay of H. Bittiger, Ciba Foundation Symposium 91, 196–199 (1982) in concentrations from about 10 $\mu$mol/L. In vivo, they inhibit, from a dose of about 0.01 mg/kg i.v., the vasodilatation induced by substance P, measured on the guinea pig ear based on the experimental design of Andrews and Helme, Regul. Pept. 25, 267–275 (1989) and, from a dose of about 1.0 mg/kg i.v., based on the experimental design of Lundberg et al, Proc. Nat. Acad. Sci. (USA) 80, 1120–1124 vagally induced bronchospasms in the guinea pig, which indicates their suitability for the treatment of asthma. Their utilisability for the treatment of disorders of the central nervous system is indicated, for example, by their inhibitory effect on the change in behaviour induced by icv-applied substance P methyl ester in the gerbil according to A. Vassout et al., Meeting on Substance P, Worcester, Mass. (1990) with an $ED_{50}$ from about 10 mg/kg s.c., from about 30 mg/kg i.p. and from about 100 mg/kg p.o.

Substance P is a naturally occurring undecapeptide of the tachykinin family. It is produced in the mammalian body and acts pharmacologically as neuropeptide. Substance P plays an essential role in various disorders, for example in conditions of pain, in migraine and in some disorders of the central nervous system, such as in anxiety states, schizophrenia and depression, as well as in certein movement disorders, such as in Parkinson's disease, but also in inflammatory disorders such as in rheumatoid arthritis, iritis and conjunctivitis, in disorders of the respiratory organs such as in asthma and chronic bronchitis, in disorders of the gastrointestinal system, such as in ulcerative colitis and Crohn's disease, and in hypertension.

There has therefore been no lack of attempts to develop substance P antagonists. However, a series of the substance P antagonists disclosed to date are peptidic compounds which are too metabolically labile to be employed as pharmaceutically active substances.

The substance P antagonists, prepared according to the invention, of the formula I and their pharmaceutically utilisable salts are, by contrast, metabolically stable and accordingly outstandingly suitable for the therapeutic treatment of the said disorders.

The invention primarily relates to compounds of the formula I in which $R_1$ is a phenyl-, diphenyl-, naphthyl- or fluorenyl-lower-alkyl radical which is unsubstituted or substituted in the phenyl moiety by lower alkyl, lower alkoxy, di-lower-alkylamino, halogen and/or trifluoromethyl, a phenoxy-lower-alkyl radical which is unsubstituted or substituted in the phenyl moiety by halogen and/or triazolyl, a heteroaryl-lower-alkyl radical which has as heteroaryl radical aza-heteroaryl which is 6-membered and monocyclic or is bicyclic and composed of a 6-membered and a 5- or 6-membered ring, a benzoyl, naphthoyl fluorenoyl or 3- to 8-membered cycloalkylcarbonyl radical which is unsubstituted or substituted by lower alkyl, lower alkoxy, hydroxyl, di-lower-alkylamino, halogen, cyano and/or trifluoromethyl, a phenyl- or diphenyl-lower-alkanoyl radical which is unsubstituted or substituted in the phenyl moiety by lower alkyl, lower alkoxy, di-lower-alkylamino, halogen and/or trifluoromethyl, a heteroaryl-lower-alkanoyl radical which has as heteroaryl radical aza-heteroaryl which is 6-membered and monocyclic or is bi- or tricyclic and composed of a 6-membered and one or two 5- or 6-membered ring(s), a phenyl-lower-alkoxycarbonyl or N-phenylcarbamoyl radical which is unsubstituted or substituted in the phenyl moiety by lower alkyl, lower alkoxy, di-lower-alkylamino, halogen and/or trifluoromethyl, or the acyl radical of an $\alpha$-amino acid which occurs in nature as peptide building block and is optionally N-substituted by lower alkanoyl or carbamoyl-lower-alkanoyl, $R_2$ is 5- to 7-membered cycloalkyl or a phenyl, naphthyl or 6-membered monocyclic aza-heteroaryl radical which is unsubstituted or substituted by aromatically bonded lower alkyl, lower alkoxy, halogen and/or trifluoromethyl, $R_3$ is hydrogen, lower alkyl, carbamoyl, lower alkanoyl, carboxy-lower-alkanoyl or carboxy-lower-alkenoyl, lower alkoxycarbonyl-lower-alkyl, carbamoyl-lower-alkanoyl, N-mono- or N,N-di-lower-alkylcarbamoyl-lower-alkanoyl, N-cyclalkylcarbarnoyl-lower-alkanoyl or N-phenylcarbamoyl-lower-alkanoyl, $R_4$ is a phenyl, naphthyl or pyridyl radical which is unsubstituted or substituted by lower alkyl, lower alkoxy, halogen and/or trifluoromethyl, or a heteroaryl radical which is unsubstituted or C-substituted by lower alkyl, lower alkoxy, halogen and/or trifluoromethyl and optionally N-substituted by lower alkanoyl and is composed of an optionally partially hydrogenated 5- or 6-membered mono- or diaza- or oxa-heteroaryl radical and a 6-membered aryl radical, $X_1$ is methylene, ethylene, a carbonyl group which is optionally ketalised with a lower alkanol or a lower alkanediol, a hydroxymethylene group which is optionally etherified with a lower alkanol, or a direct linkage, $X_2$ is carbonyl, lower alkylene or a direct linkage, and $X_3$ is carbonyl, oxo-lower-alkylene, oxo(aza)-lower-alkylene or a lower alkylene radical which is unsubstituted or substituted by phenyl or in the 1, 2 or, where present, 3 position with respect to the N atom by carboxyl, lower alkoxycarbonyl, carbamoyl, N-mono- or N,N-di-lower-alkylcarbamoyl or hydroxymethyl, and the salts thereof.

The invention particularly relates to compounds of the formula I in which $R_1$ is phenyl- or diphenyl-$C_1$-$C_4$alkyl which is unsubstituted or substituted in the phenyl moiety by lower alkyl, lower alkoxy, di-lower-alkylamino, halogen and/or trifluoromethyl, such as benzyl, 2,4-dichlorobenzyl, 3,5-ditrifluoromethylbenzyl, 2-phenylethyl or 2,2-diphenylethyl, phenoxy-$C_1$-$C_4$alkyl which is unsubstituted or substituted in the phenyl by halogen and/or triazolyl, pyndyl- or quinolinyl-$C_1$-$C_4$alkyl, such as 4-quinolinylmethyl, benzoyl which is unsubstituted or substituted by lower alkyl, lower alkoxy, di-lower-alkylamino, halogen and/or trifluoromethyl, such as benzoyl, 3-lower-alkyl-, 3-lower-alkoxy-, 3-halogeno-, 3-dimethylamino-, 3,5-di-lower-alkyl, 3,5-di-lower-alkoxy-, 3,5-dihalogeno- or 3,5-ditrifluoromethylbenzoyl, or secondarily naphthoyl which is unsubstituted or substituted by lower alkyl, lower alkoxy, di-lower-alkylamino, halogen and/or trifluoromethyl, such as 1- or 2-naphthoyl, pyridylcarbonyl or quinolinylcarbonyl which is unsubstituted or substituted by lower alkyl, lower alkoxy, halogen and/or trifluoromethyl, 5- to 7-membered cycloalkylcarbonyl which is unsubstituted or substituted by lower alkyl, lower alkoxy, di-lower-alkylamino, halogen and/or trifluoromethyl, such as cyclohexylcarbonyl, 3-methyl-, 3-methoxy-, 3-chloro-, 3-dimethylamino-, 3,5-dmethyl-, 3,5-dimethoxy-, 3,5-dichloro or 3,5-ditrifluoromethylcyclohexylcarbonyl, phenyl- or diphenyl-$C_1$-$C_4$alkanoyl which is unsubstituted or substituted in the phenyl by lower alkyl, lower alkoxy, di-lower-alkylamino, halogen and/or trifluoromethyl, such as 2,2-diphenylacetyl or 2,3-diphenylpropionyl, N-phenylcarbamoyl which is unsubstituted or optionally substituted in the phenyl moiety by lower alkyl, lower alkoxy, di-lower-alkylamino, halogen and/or trifluoromethyl, or a group of the formula Ia

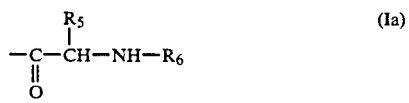

in which $R_5$ is hydrogen, $C_1$-$C_4$alkyl which is unsubstituted or substituted by hydroxyl, mercapto, amino, optionally hydroxy-substituted phenyl, carboxyl, carbamoyl or ureido, and $R_6$ is $C_2$-$C_7$alkanoyl, $R_2$ is 5- to 7-membered cycloalkyl or a phenyl, naphthyl or pyridyl radical which is unsubstituted or substituted by $C_1$-$C_4$alkyl, $C_1$-$C_4$alkoxy, halogen and/or trifluoromethyl, $R_3$ is hydrogen, $C_1$-$C_7$alkyl, carbamoyl, $C_2$-$C_7$alkanoyl, carboxy-$C_1$-$C_4$alkanoyl or carboxy-$C_2$-$C_4$alkenoyl, $R_4$ is phenyl or naphthyl which is unsubstituted or substituted by $C_1$-$C_4$alkyl, $C_1$-$C_4$alkoxy, halogen and/or trifluoromethyl, or unsubstituted pyridyl, benzofuranyl, indolyl, 2,3-dihydroindolyl, benzimidazolyl, quinolyl or 1,2,3,4-tetrahydroquinolinyl, $X_1$ is methylene, hydroxymethylene, $C_1$-$C_4$alkoxymethylene, carbonyl, di-$C_1$-$C_4$alkoxymethylene or a direct linkage, $X_2$ is $C_1$-$C_7$alkylene, carbonyl or a direct linkage, and $X_3$ is carbonyl, $C_1$-$C_4$alkylene, carboxy-$C_1$-$C_4$alkylene, $C_1$-$C_4$alkoxycarbonyl-$C_1$-$C_4$alkylene, carbamoyl-$C_1$-$C_4$alkylene or hydroxymethyl-$C_1$-$C_4$alkylene and the salts thereof.

The invention particularly relates to compounds of the formula I in which $R_1$ is benzoyl, naphthoyl or phenyl-$C_1$-$C_4$alkanoyl which is unsubstituted or substituted by $C_1$-$C_4$alkyl, such as methyl, $C_1$-$C_4$alkoxy, such as methoxy, halogen and/or trifluoromethyl, unsubstituted pyridylcarbonyl or quinolinylcarbonyl or a group of the formula Ia

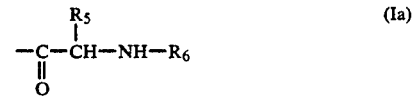

in which $R_5$ is hydrogen, $C_1$-$C_4$alkyl which is unsubstituted or substituted by hydroxyl, mercapto, amino, optionally hydroxy-substituted phenyl, carboxyl, carbamoyl or ureido, for example methyl, isopropyl, isobutyl, secondary butyl, hydroxymethyl, mercaptomethyl, 2-methylmercaptoethyl, 3-ureidopropyl, 4-aminobutyl, carboxymethyl, carbamoylmethyl, 2-carboxyethyl, 2-carbamoylethyl, benzyl or 4-hydroxybenzyl, and $R_6$ is $C_2$-$C_7$alkanoyl, such as acetyl, propionyl, butyryl or pivaloyl, $R_2$ is 5- to 7-membered cycloalkyl, especially cyclohexyl or secondarily cyclopentyl or cycloheptyl, or a phenyl, naphthyl or pyridyl radical which is unsubstituted or substituted by $C_1$-$C_4$alkyl, such as methyl, $C_1$-$C_4$alkoxy, such as methoxy, halogen and/or trifluoromethyl, $R_3$ is hydrogen, $C_1$-$C_7$alkyl, such as methyl, ethyl, propyl, isopropyl or butyl, isobutyl, secondary butyl or tertiary butyl, carbamoyl, $C_2$-$C_7$alkanoyl such as acetyl, propionyl, butyryl or pivaloyl, carboxy-$C_1$-$C_4$alkanoyl such as succinoyl, glutaroyl or adipoyl, or carboxy-$C_3$-$C_5$alkenoyl such as maleyl, fumaroyl or tartroyl, $R_4$ is phenyl or naphthyl which is unsubstituted or substituted by $C_1$-$C_4$alkyl, such as methyl, $C_1$-$C_4$alkoxy, such as methoxy, halogen and/or trifluoromethyl, or unsubstituted pyridyl, benzofuranyl, indolyl, benzimidazolyl or quinolyl, $X_1$ is methylene, hydroxymethylene, $C_1$-$C_4$alkoxymethylene such as methoxymethylene, ethoxymethylene, propyloxymethylene or butyloxymethylene, carbonyl, di-$C_1$-$C_4$alkoxymethylene such as dimethoxymethylene, diethoxymethylene, dipropyloxymethylene or dibutyloxymethylene, or a direct linkage, $X_2$ is $C_1$-$C_7$alkylene such as methylene or secondarily ethylene or 1,3-propylene, carbonyl or a direct linkage, and $X_3$ is carbonyl, $C_1$-$C_4$alkylene, such as methylene, ethylene or or 1,3-propylene, carboxy-$C_1$-$C_4$alkylene such as 1,3-(2-carboxy)propylene, 1,4-(2-carboxy)butylene, 1,4-(3-carboxy)butylene, $C_1$-$C_4$alkoxycarbonyl-$C_1$-$C_4$alkylene, such as 1,3-(2-$C_1$-$C_4$alkoxycarbonyl)propylene, 1,4-(2-$C_1$-$C_4$alkoxycarbonyl)butylene, 1,4-(3-$C_1$-$C_4$alkoxycarbonyl)butylene, 1,5-(2-$C_1$-$C_4$alkoxycarbonyl)pentylene 1,5-(3-$C_1$-$C_4$alkoxycarbonyl)pentylene or 1,5-(4-$C_1$-$C_4$alkoxycarbonyl)pentylene, where $C_1$-$C_4$alkoxycarbonyl means in each case, for example, methoxycarbonyl, ethoxycarbonyl, propoxycarbonyl or butoxycarbonyl, carbamoyl-$C_1$-$C_4$alkylene such as 1,3-(2-carbamoyl)propylene, 1,4-(2-carbamoyl)butylene, 1,4-(3-carbamoyl)butylene, 1,5-(2-carbamoyl)pentylene, 1,5-(3-carbamoyl)pentylene or 1,5-(4-carbamoyl)pentylene, or hydroxymethyl-$C_1$-$C_4$alkylene such as 1,3-(2-hydroxymethyl)propylene, 1,4-(2-hydroxymethyl)butylene, 1,4-(3-hydroxymethyl)butylene, 1,5-(2-hydroxymethyl)pentylene 1,5-(3-hydroxymethyl)pentylene or 1,5-(4-hydroxymethyl)-pentylene, and the salts thereof.

The invention preferably relates to compounds of the formula I in which $R_1$ is benzoyl which is unsubstituted or mono- or disubstituted by $C_1$-$C_4$alkyl, such as methyl, $C_1$-$C_4$alkoxy, such as methoxy, halogen of atomic number up to and including 35, such as chlorine, and/or trifluoromethyl, or unsubstituted naphthoyl or phenyl-$C_1$-$C_4$alkanoyl, $R_2$ is phenyl which is unsubstituted or mono- or disubstituted by $C_1$-$C_4$alkyl, such as methyl, $C_1$-$C_4$alkoxy, such as methoxy, halogen of atomic number up to and including 35, such as chlorine, and/or trifluoromethyl, or unsubstituted pyridyl, $R_3$ is hydrogen, $C_1$-$C_4$alkyl such as methyl, ethyl, propyl. or isopropyl, carbamoyl or $C_2$-$C_7$alkanoyl such as acetyl, propionyl, butyryl or pivaloyl, $R_4$ is phenyl which is unsubstituted or mono- or disubstituted by $C_1$-$C_4$alkyl, such as methyl, $C_1$-$C_4$alkoxy, such as methyl, halogen of atomic number up to and including 35, such as chlorine, and/or trifluoromethyl, or unsubstituted naphthyl, pyridyl, benzofuranyl, indolyl, benzimidazolyl or quinolyl, $X_1$ is methylene, hydroxymethylene, carbonyl or a direct linkage, $X_2$ is a direct linkage, and $X_3$ is $C_1$-$C_4$alkylene, such as methylene or secondarily ethylene or 1,3-propylene, and the salts thereof.

The invention relates above all to compounds of the formula I in which $R_1$ is benzoyl which is unsubstituted or mono- or disubstituted by $C_1$-$C_4$alkyl such as methyl, $C_1$-$C_4$alkoxy such as methoxy, halogen of atomic number up to and including 35 such as chlorine and/or trifluoromethyl, or unsubstituted naphthoyl, $R_2$ is unsubstituted phenyl or phenyl mono- or disubstituted by halogen of atomic number up to and including 35 such as chlorine and/or trifluoromethyl, $R_3$ is hydrogen, $R_4$ is unsubstituted quinolinyl, $X_1$ is methylene, $X_2$ is a direct linkage, and $X_3$ is $C_1$-$C_4$alkylene such as methylene or secondarily ethylene or 1,3-propylene, and to the salts thereof.

The invention especially relates to the compounds of the formula I, and the salts thereof, specified in the examples.

The invention furthermore relates to a process, which is based on methods known per se, for the preparation of the compounds according to the invention. This is characterised in that a) the radical $R_1$ is introduced into a compound of the formula II

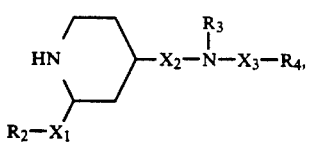

(II)

in which $R_2$, $R_3$, $R_4$, $X_1$, $X_2$ and $X_3$ have the indicated meanings, or b) compounds of the formulae III and IV

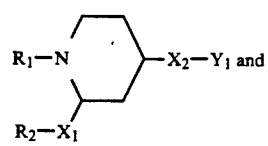

(III)

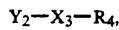

$Y_2$—$X_3$—$R_4$, (IV)

in which $Y_1$ is a group of the formula —N($R_3$)—H and $Y_2$ is hydroxyl, reactive esterified hydroxyl or, if $X_3$ is carbonyl, is etherified hydroxyl, or $Y_1$ is hydroxyl, reactively esterified hydroxyl or, if $X_2$ is carbonyl, is etherified hydroxyl and $Y_2$ is a group of the formula —N($R_3$)—H, where $R_2$, $R_3$, $R_4$, $X_1$, $X_2$ and $X_3$ have the indicated meanings, or the salts thereof, are condensed together or c) for the preparation of compounds of the formula I in which one of the radicals $X_2$ and $X_3$ is alkylene and the other is alkylene, carbonyl or, in the case of $X_2$, a direct linkage or, in the case of $X_3$, an alkylene radical which is optionally substituted by hydroxymethyl or optionally esterified or amidated carboxyl, in a compound of the formula V

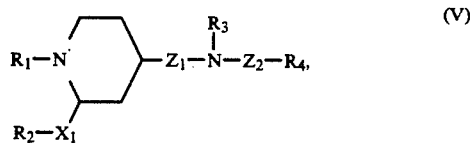

(V)

in which $Z_1$ is an alkylene radical which is substituted by oxo or hydroxyl in the α position to the group —N($R_3$)—, and $Z_2$ is alkylene, carbonyl or an alkylene radical which is optionally substituted by hydroxymethyl or optionally esterified or amidated carboxyl, or $Z_1$ is alkylene, carbonyl or a direct linkage and $Z_2$ is alkylene radical substituted by oxo or hydroxyl in the α position to the group —N($R_3$)—, and $R_2$, $R_3$, $R_4$, $X_1$, $X_2$ and $X_3$ have the indicated meanings, or in a salt thereof, the oxo or hydroxyl group in the α position to the group —N($R_3$)— is replaced by hydrogen by reduction, or in a compound of the formula VI

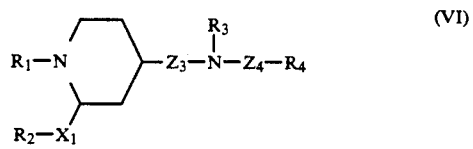

(VI)

in which $Z_3$ is a radical of the formula —C($R_a$)=C($R_b$)— and $Z_4$ is alkylene, carbonyl or an alkylene radical which is optionally substituted by hydroxymethyl or optionally esterified or amidated carboxyl, or $Z_3$ is alkylene, carbonyl or a direct linkage and $Z_4$ is a radical of the formula —C($R_a$)=C($R_b$)—, where $R_a$ and $R_b$ are each hydrogen or lower alkyl, the radical of the formula —C($R_a$)=C($R_b$)— is reduced by reduction of the double bond to the corresponding radical —CH($R_a$)—CH($R_b$)—, or d) for the preparation of compounds of the formula I in which $X_1$ is a carbonyl or hydroxymethylene group, compounds of the formulae VII and VIII

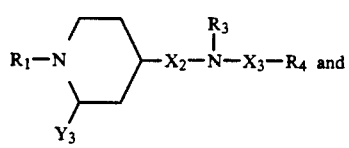

(VII)

$Y_4$—$R_2$, (VIII)

in which one of the radicals $Y_3$ and $Y_4$ is formyl or an optionally anhydrised or esterified carboxyl group and the other is a metallic radical, and $R_2$, $R_3$, $R_4$, $X_2$ and $X_3$ have the indicated meanings, are condensed together or e) for the preparation of compounds of the formula I in which $R_3$ is hydrogen, the group $Y_5$ is eliminated from a compound of the formula IX

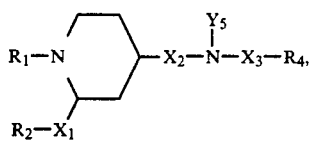

(IX)

in which $Y_5$ is an amino-protective group, and $R_2$, $R_4$, $X_1$, $X_2$ and $X_3$ have the indicated meanings, or from a salt thereof, or f) for the preparation of compounds of the formula I in which $X_3$ is alkylene, compounds of the formulae X and XI

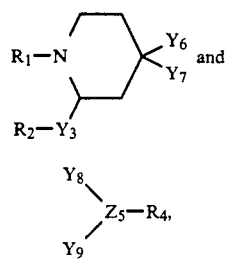

(X)

(XI)

in which $Y_6$ is a group of the formula $—N(R_3)—H$, $Y_7$ is hydrogen, $Y_8$ and $Y_9$ together are oxo and $Z_5$ is an alkanylylidene radical corresponding to $X_3$, or $Y_6$ and $Y_7$ together are oxo, $Y_8$ is a group of the formula $—N(R_3)—H$, $Y_9$ is hydrogen and $Z_5$ is a radical $X_3$, are condensed together under reducing conditions and, if required, a resulting compound is converted into another compound of the formula I, a mixture of isomers which can be obtained according to the process is fractionated into the components, and the isomer preferred in each case is separated off and/or a free compound which can be obtained according to the process is converted into a salt, or a salt which can be obtained according to the process is converted into the corresponding free compound.

The carrying out of the reactions according to the process, and the preparation of novel starting materials and intermediates takes place in analogy to the way of reacting and forming known starting materials and intermediates respectively. The aids customary in each case are used for this, even when not expressly mentioned hereinafter, such as catalysts, condensing and solvolysing agents and/or solvents or diluents, and reaction conditions such as temperature and pressure conditions, as well as, where appropriate, protective gases.

Introduction of the radical $R_1$ according to process variant a) is carried out in a conventional way, for example by reaction with an agent introducing the radical $R_1$, such as an N-acylating agent of the formula $R_1—Y_a$ (IIa1) in which $R_1$ is an optionally substituted aroyl, heteroaroyl, cycloalkylcarbonyl, aralkanoyl, heteroarylalkanoyl or arylcarbamoyl radical or the acyl radical of an optionally N-alkanoylated α-amino acid and $Y_a$ is optionally ehterified hydroxy, such as hydroxy, lower alkoxycarbonyl or optionally substituted phenyloxycarbonyl, or reactively esterified hydroxy, such as halogen, especially chlorine, or a radical of the formula $—O—R_1$, or with an aralkylating, aryloxyalkylating or heteroarylalkylating agent of the formula $R_1—Y_b$(IIa2) in which $R_1$ is an optionally substituted aralkyl, aryloxyalkyl, heteroalkyl radical and $Y_b$ is reactive esterified hydroxyl, such as halogen, for example chlorine, bromine or iodine, or a sulfonyloxy group such as an alkane- or optionally substituted benzenesulfonyloxy group, for example methane-, ethane-, benzene-, p-toluene- or p-bromobemzenesulfonyloxy, or by reaction with under reducing conditions with a compound of the formula $R_1=O$ (IIa3) in which $R_1$ is an optionally substituted aralkyl, aryloxyalkyl, heteroaralkyl radical.

If necessary, the operation is carried out with thermal decomposition of ammonium salts formed as intermediates, or in the presence of a condensing agent such as a water-binding agent, or basic condensing agent, and in the presence of a solvent or diluent. Thus, reaction with acids of the formula IIa1 (Y=COOH) is preferably carried out in the presence of a water-binding agent, such as of N,N-dicyclohexylcarbodiimide, or with thermal decomposition of the ammonium salt initially formed, while reaction with acid anhydrides of the formula IIa1 (Y=halogen or $—O—(C=O)—R_1$) and with compounds of the formula IIa2 is preferably carried out in the presence of a basic condensing agent, such as of an alkali metal hydroxide or carbonate, or of a tertiary or sterically hindered secondary organic amine such as of a tri-lower-alkylamine, for example of triethylamine or diisopropylamine, or of an aromatic nitrogen base, for example of pyridine.

Reaction of compounds of the formula IIa3 is carried out, for example, in the presence of hydrogen and of a hydrogenation catalyst such as of a platinum or palladium catalyst or of Raney nickel, or in the presence of a di-light-metal hydride such as sodium borohydride or sodium cyanoborohydride, preferably in a solvent which is inert under the reaction conditions, such as of a lower alkanol, such as methanol or ethanol, or of a di-lower-alkyl or lower alkylene ether such as diethyl ether, dioxane or tetrahydrofuran.

The starting materials of the formula II can be prepared in a conventional way, for example by reacting compounds of the formulae

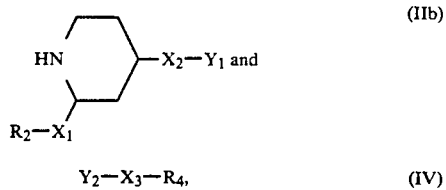

(IIb)

$Y_2—X_3—R_4$, (IV)

with one another, for example as described hereinafter for process variant b).

Reactive esterified hydroxyl in starting materials of the formula III or IV according to process variant b) means, for example, a halogen, such as chlorine, bromine or iodine atom, or, if $X_3$ is different from carbonyl, denotes a sulfonyloxy group, for example methanesulfonyloxy or p-toluenesulfonyloxy, or, if $X_3$ represents carbonyl, denotes a group of the formula $—O—(C=O)—R_4$. Etherified hydroxyl means, for example, lower alkoxy such as methoxy or ethoxy, or optionally substituted phenyloxy. Anhydridised hydroxyl is, for example, halogen, especially chlorine, or a group of the formula $—O—(C=O)—R_4$.

Reaction of compounds of the formulae III and IV is carried out in a conventional way, for example with thermal decomposition of ammonium salts formed as intermediates, or in the presence of a condensing agent such as a water-binding agent, or basic condensing agent, and in the presence of a solvent or diluent. Thus, reaction with acids of the formula IV or III ($Y_2$ or $Y_1$=OH) is preferably carried out in the presence of a water-binding agent, such as of N,N-dicyclohexylcarbodiimide, or with thermal decomposition of the ammonium salt formed initially, while reaction with reactive esters of the formula IV or III ($Y_2$ or $Y_1$=reactive esterified hydroxyl) or with acid anhydrides of the formula IV or III ($Y_2$ or $Y_1$=anhydridised hydroxyl) is preferably carried out in the presence of a basic condensing agent, such as of an alkali metal hydroxide or carbonate, or of a tertiary or sterically hindered secondary organic amine, such as of a tri-lower-alkylamine, for example of triethylamine or diisopropylamine, or of an aromatic nitrogen base, for example of pyridine.

The starting materials of the formula III can be prepared in a conventional way, for example by introducing the radical $R_1$ into a compound of the formula IIIa

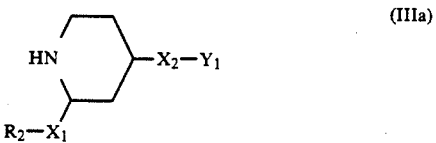

for example as described above under process variant a).

Reductive replacement of the oxo or hydroxyl group in the α position to the group —N($R_3$)— by hydrogen or the reduction of the double bond in the radical of the formula —C($R_a$)=C($R_b$)— according to process variant c) is carried out, for example, by catalytic hydrogenation, that is to say treatment with hydrogen in the presence of a hydrogenation catalyst, such as of a metal or of a metal compound of a metal of group VIIIb of the periodic table, such as platinum, plantinumoxide, palladium/carbon or of Raney nickel, or by reaction with a di-light-metal hydride such as an alkali metal borohydride, for example with sodium cyanoborohydride, of by treatment with formic acid.

Starting materials of the formula V or VI can, for example, by condensation of compounds of the formulae Va and Vb

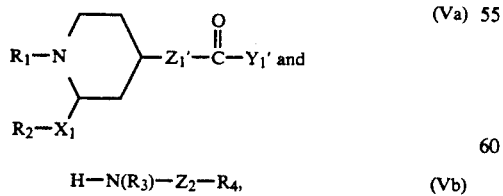

in which $Z_1'$ is a direct linkage or a radical $X_2$ shortened by a C atom and $Y_1'$ is hydrogen, lower alkyl or free, etherified or reactive esterified hydroxyl, and $Z_2$ has the indicated meaning, or of compounds of the formula VIa and VIb

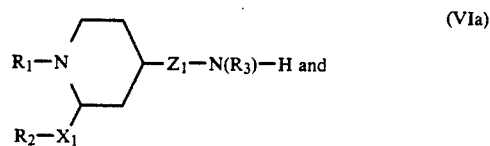

in which $Z_1$ has the indicated meaning, $Z_2'$ is a direct linkage or a radical $X_3$ shortened by a C atom and $Y_2'$ is hydrogen, lower alkyl or free, etherified or reactive esterified hydroxyl. If $Y_1'$ in compounds of the formula Va or $Y_2'$ in compounds of the formula VIb is hydrogen or lower alkyl there is formation of the corresponding compounds of the formula V under mild reaction conditions, especially in a basic or neutral medium, and of the corresponding compounds of the formula VI under drastic reaction conditions, especially in acid medium. In the last-mentioned case this entails formation of the corresponding compounds of the formula V as intermediates, from which the corresponding compounds of the formula VI are then formed by elimination of water. Starting materials of the formulae V and VI can also be produced side by side. In a preferred embodiment of the invention, the intermediates of the formula V or VI are formed in situ and reduced without isolation to the corresponding compounds of the formula I by carrying out the condensation of starting materials of the formulae Va and Vb or VIa and VIb in the presence of one of the said reducing agent.

Optionally anhydridised or esterified carboxyl $Y_3$ or $Y_4$, respectively, in starting materials compounds of the formula VII or VIII for process variant d) means, for example, halogenocarbonyl or, in the case of $Y_4$, a group of the formula $R_2$—C(=O)—O— and a metallic radical $Y_3$ or $Y_4$, for example an alkali metal atom or a group of the formula —$M^{II}$/2 or $M^{II}$—Hal in which $M^{II}$ is a metal atom of group IIb of the periodic table of the elements, such as Mg or Zn.

Reaction of compounds of the formulae VII and VIII is carried out in a conventional way, for example in an ether-like solvent such as an aliphatic or cycloaliphatic ether, for example in diethyl ether, methoxybutane, dibutyl ether, tetrahydrofuran or dioxane Starting materials of the formula VII in which $Y_3$ is formyl or optionally anhydridised or esterified carboxyl are prepared, for example, by condensing together compounds of the formulae VIIa and VIIIa

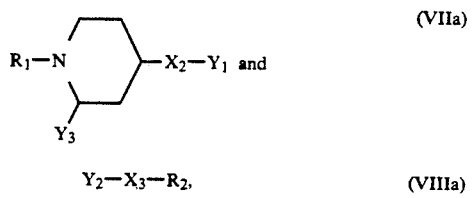

in which $Y_1$ is a group of the formula —N($R_3$)—H and $Y_2$ is hydroxyl, are reactive esterified hydroxyl or, if $X_3$ is carbonyl, etherified or anhydridised hydroxyl, or $Y_1$ is hydroxyl, reactively esterified hydroxyl or, if $X_2$ is carbonyl, etherified or anhydridised hydroxyl and $Y_2$ is a group of the formula —N($R_3$)—H, where $R_2$, $R_3$, $R_4$, $X_1$, $X_2$ and $X_3$ have the indicated meanings, or the salts thereof, for example as indicated under process variant b).

Starting materials of the formulae VII and VIII in which $Y_3$ or $Y_4$ is a metallic radical are preferably prepared in situ by reacting a compound of the formula VIIb

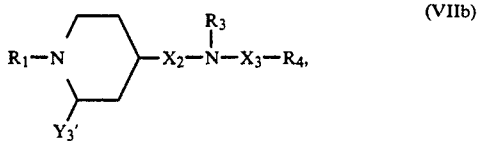

in which $Y'_3$ is a halogen atom, especially chlorine, bromine or iodine, with a metal of the formula $M^{II}$, or starting from compounds of the formula $Y_4'$—$R_2$ (VIIIb) in which $Y_4'$ is hydrogen or a halogen atom, especially chlorine, bromine or iodine, reacting a compound of the formula VIIIb in which $Y_4'$ is hydrogen with an organometallic compound, for example a metal derivative of an aliphatic hydrocarbon, for example with butyllithium, or reacting a compound of the formula VIIIb in which $Y_4'$ is a halogen atom with a metal of the formula $M^{II}$.

The amino-protective group $Y_5$ in starting materials of the formula IX according to process variant e) is, for example, an optionally halogenated lower alkanoyl group such as trifluoroacetyl, or an acyl group derived from a monoester of carbonic acid, such as a lower alkoxycarbonyl or α-phenyl-lower-alkoxycarbonyl group, for example teritary butyloxycarbonyl or benzyloxycarbonyl, or a silyl group such as tri-lower-alkylsilyl, for example trimethylsilyl. The elimination of the amino-protective group is carried out in a conventional way, for example by acid treatment, or starting from compounds IX in which $Y_5$ is halogenated lower alkanoyl, such as trifluoroacetyl, by reductive elimination, for example by treatment with a di-light-metal hydride such as sodium borohydride, preferably in a lower alkanol such as methanol.

The starting materials of the formula IX can be prepared, for example, in analogy to process variant a) starting from corresponding compounds of the formula IXa

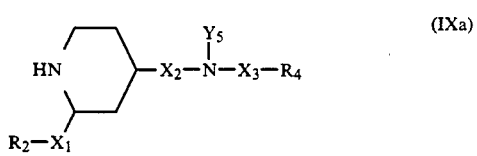

Reaction of compounds of the formulae X and XI according to process variant f) is carried out, for example, by elimination of water, for example by azeotropic distillation, in particular with toluene, and subsequent reduction with borane or a di-light-metal hydride such as an alkali metal borohydride, for example with sodium boranate or sodium cyanoborohydride.

Starting materials of the formula X, wherein $R_1$ denotes an acyl radical as defined under formula I, $X_1$ is hydroxymethylene and $Y_6$ and $Y_7$ together represent oxo, and their pharmazeutically acceptable salts, exhibit the same pharmacological properties and comparable activities as the final products of formula I.

The inventions, therefore, relates also to 1-acylpiperidones of formula X

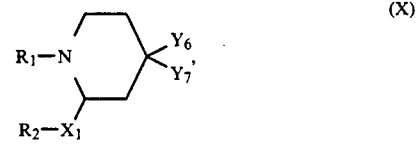

wherein $R_1$ is an optionally substituted aroyl, heteroaroyl, cycloalkylcarbonyl, aralkanoyl, heteroarylalkanoyl, aralkoxycarbonyl or arylcarbamoyl radical or the acyl radical of an α-amino acid which is optionally N-substituted by lower alkanoyl or carbamoyl-lower-alkanoyl, $R_2$ is cycloalkyl or an optionally substituted aryl or heteroaryl radical, $X_1$ denotes hydroxymethylene and $Y_6$ and $Y_7$ together represent oxo, and to their salts, to a process for the preparation of the compounds according to the invention, to pharmaceutical products containing these, and to their use as pharmaceutically active substances.

In these compounds, $R_2$ preferably has the meaning indicated for the compounds of the formula I, above all the meaning indicated for especially preferred compounds of formula I.

The invention most preferably relates to those compounds of formula X, wherein $R_1$ denotes benzoyl, benzoyl mono- or disubstituted by $C_1$-$C_4$-alkyl, such as methyl, $C_1$-$C_4$-alkoxy, such as methoxy, halogen of atomic number up to and including 35, such as chloro, and/or trifluoromethyl or unsubstituted naphthoyl, $R_2$ represents phenyl or phenyl mono- or disubstituted by halogen of atomic number up to and including 35, such as chloro, and/or trifluoromethyl, $X_1$ denotes hydroxymethylene and $Y_6$ and $Y_7$ together represent oxo, and to their salts.

The invention specifically relates to the compounds or formula X described in the Examples herein and to their salts.

The compounds of formula X according to invention in which $R_1$ and $R_2$ have the meanings indicated, $X_1$ denotes hydroxymethylene and $Y_6$ and $Y_7$ together represent oxo, and their salts are prepared by methods known per se. The process for their manufacture is characterised in that a compound of the formula Xa

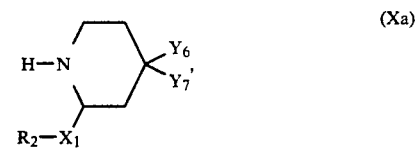

is condensated with an agent suitable to introduce the group $R_1$ and, if required, a resulting compound is converted into another compound of the formula I, a mixture of isomers which can be obtained according to the process is fractionated into the components, and the isomer preferred in each case is separated off and/or a free compound which can be obtained according to the process is converted into a salt, or a salt which can be obtained according to the process is converted into the corresponding free compound.

Agents suitable to introduce the group $R_1$ are, for example, compounds of the formula $R_1$—$Y_{10}$ (Xb) in which $Y_{10}$ denotes reactive esterified hydroxy, such as halogen or a sulfonyloxy group, for example, benzene-, p-toluene- or methansulfonyloxy, or if $R_1$ denotes an aroyl-, heteroaroyl-, cycloalkylcarbonyl-, aralkanoyl-, heteroarylalkanoyl-, aralkoxycarbonyl- or arylcarbamoylrest or the acyl moiety of an α-amino acid which may be N-substituted by lower alkanoyl or carbamoyl-lower alkanoyl, is etherified hydroxy, such as lower alkoxy or phenyloxy which may be substituted by halogen and/or nitro.

The condensation is performed in a manner, for example, in the presence of a basic condensation adjuvan, such as in the presence of an alkalimetall hydrogencarbonate, for example, of Sudium hydrogencarbonate, preferably in a water-containing bi-phasic system, for example, in methylenechloride/water.

Compounds of formula Xa con, in turn, be obtained by reacting a N-protected piperidin-4-one ketal, such as 1-(tert.-butyloxycarbonyl)piperindin-4-one ethyleneketal, with an aldehyd of the formula $R_2$—CH=O (Xc), for example in the presence of a hydorcarbon-metal, such as a hydorocarbon alkalimetal derivative, preferably of a lower-alkyl lithium compound, such as of sec.-butyl lithium, preferaböy in an etheric solvent, such as diethyl ether, at −30+ to −80° C., for example at −60° to −75° C.

Compounds of formula X, wherein $Y_6$ denotes a group of the formula —N($R_3$)—H and $Y_7$ denotes hydrogen, are, for example, prepared by condensing a compound of the formula $R_2$—$X_1$—Y (Xd) in which Y is reactive esterified hydroxyl, such as halogen, lower alkanesulfonyloxy or optionally substituted benzenesulfonyloxy, in the presence of an alkali metal lower alkanolate such as sodium methanolate, in a lower alkanol such as methanol, or in the presence of sodamide in toluene with a lower alkyl but-2-ene-1,1-dicarboxylate of the formula $CH_2$=CH—$CH_2$—CH(COOR)$_2$ (Xe; R=lower alkyl), hydrolysing and decarboxylating the reaction product of the formula Xf

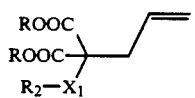

(Xc)

by treatment with an alkali metal hydroxide, for example with potassium hydroxide in aqueous methanol, amidating the resulting acid of the formula Xg

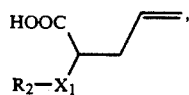

(Xg)

for example by treatment with a halogenating agent such as oxalyl chloride or thionyl chloride followed by reaction with ammonia, and subsequently degrading to the corresponding amine of the formula Xh

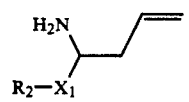

(Xh)

condensing the latter, after protection of the amino group, for example by acylation, with a is lower alkoxymethyl halide of the formula RO—$CH_2$—Hal (Xf; R=lower alkyl; Hal=halogen), for example with chlorodimethyl ether in the presence of sodium hydroxide in dichloromethane/water, cyclocondensing the reaction product of the formula Xi

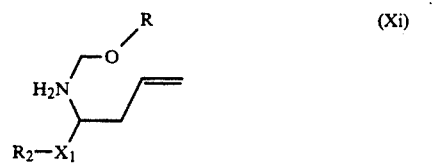

(Xi)

by acid treatment, for example treatment with a Lewis acid such as tin tetrachloride, iron-III chloride, titanium tetrachloride, or pretic acid such as sulfuric acid, chlorosulfonic acid, p-toluenesulfonic acid or trifluoromethyl acetic acid or -methanesulfonic acid, in acetonitrile and, if required, acetic anhydride and another solvent such as dichloromethane, benzene or toluene, to the corresponding N-protected compound of the formula Xj

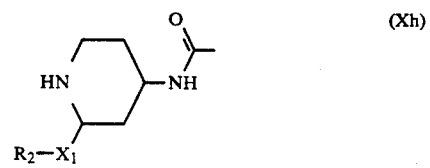

(Xh)

eliminating the amino-protective group, if required fractionating a resulting racemate into the enantiomers, introducing the group $R_1$ in a conventional way, for example, as described hereinbefore for the manufacture of compounds of formula X, wherein $X_1$ denotes hydroxymethylene and $Y_6$ eliminating the amino-protecting group by acid treatment, for example with 6N hydrochloric acid.

Compounds obtainable according to the process can be converted in a conventional way into other compounds of the formula I.

Thus, in compounds of the formula I in which $X_1$ is carbonyl can be reduced in a conventional manner to the corresponding compounds of the formula I in which $X_1$ is hydroxymethylene, for example as described under process variant c) or for the preparation of intermediates of the formulae V and VI. It is also possible in an analogous way for resulting compounds of the formula I in which $X_1$ is hydroxymethylene or $X_2$ and/or $X_3$ is carbonyl can be reduced to the corresponding compounds of the formula I in which $X_1$, $X_2$ and/or $X_3$ is methylene.

The carbonyl group in resulting compounds of the formula I in which $X_1$ is ketalised carbonyl can be liberated in a conventional way, for example by acid treatment. Conversely, carbonyl $X_1$ can be ketalised by reaction with an appropriate alcohol such as a lower alkanol or a lower alkanediol.

It is furthermore possible in resulting compounds of the formula I in which $R_3$ is hydrogen to introduce a radical $R_3$ different from hydrogen, alkyl for example by conventional alkylation, carbamoyl for example by condensation with isocyanic acid or a carbamoyl halide and alkanoyl or alkenoyl optionally substituted as indicated by conventional acylation. Conversely, in resulting compounds of the formula I in which $R_3$ is alkyl, especially methyl, the alkyl group can be eliminated by treatment with an ester, such as methylester, of haloformic acid.

Furthermore, esterified or amidated carboxyl as substituent of alkanoyl or alkenoyl $R_3$ or of alkylene $X_3$ in resulting compounds of the formula I can be hydrolysed to carboxyl or, conversely, free carboxyl can be esterified or amidated.

Resulting salts can be converted in a manner known per se into the free compounds, for example by treatment with a base such as an alkali metal hydroxide, a metal carbonate or bicarbonate, or ammonia, or with another salt-forming base mentioned in the introduction, or with an acid such as a mineral acid, for example with hydrogen chloride, or with another salt-forming acid mentioned in the introduction.

Resulting salts can be converted in a manner known per se into other salts, acid addition salts for example by treatment with a suitable metal such as a sodium, barium or silver salt, of another acid in a suitable solvent in which an inorganic salt which forms is insoluble and thus separates out of the reaction mixture, and base salts by liberation of the free acid and renewed salt formation.

The compounds of the formula I, including their salts, can also be obtained in the form of hydrates or include the solvent used for crystallisation.

As a consequence of the close relation between the novel compounds in free form and in the form of their salts, hereinbefore and herinafter the free compounds and their salts also mean, where appropriate for the sense and purpose, the corresponding salts and free compounds respectively.

Resulting mixtures of diastereomers and mixtures of racemates can also be fractionated on the basis of the physicochemical differences of the components in a known manner into the pure diastereomers and racemates respectively, for example by chromatography and/or fractional crystallisation.

Resulting racemates can furthermore be separated by known methods into the optical antipodes, for example by recrystallisation from an optically active solvent, with the aid of microorganisms or by converting the resulting mixture of diastereomers or racemate with an optically active auxiliary compound, for example appropriate for the acidic, basic or functionally modifiable groups contained in compounds of the formula I with an optically active acid, base or an optically active alcohol, into mixtures of diastereomeric salts or functional derivatives such as esters, separation thereof into the diastereomers from which the enantiomer required in each case can be liberated in the way conventional in each case. Examples of bases, acids and alcohols suitable therefore are optically active alkaloid bases such as strychnine, cinchonine or brucine, or D- or L-(1-phenyl)ethylamine, 3-pipecoline, ephedrine, amphetamine and similar bases obtainable by synthesis, optically active carboxylic or sulfonic acids such as quinic acid or D- or L-tartaric acid, D- or L-di-o-toluyltartaric acid, D- or L-malic acid, D- or L-mandelic acid, or D- or L-camphorsulfonic acid, or optically active alcohols such as borneol or L- or L-(1-phenyl)ethanol.

The invention also relates to those embodiments of the process which start from a compound obtainable as intermediate at any stage of the process and in which the missing steps are carried out or a starting material is used in the form of a salt or, in particular, forms under the reaction conditions.

The invention likewise relates to the novel starting materials which have been specifically developed for the preparation of the compounds according to the invention, in particular the choice of starting materials leading to the compounds of the formula I which are characterised as preferred in the introduction, to the processes for the preparation thereof and to the use thereof as intermediates.

The novel compounds of the formula I can be used, for example, in the form of pharmaceutical products which contain a therapeutically effective amount of the active substance, where appropriate together with inorganic or organic, solid or liquid, pharmaceutically utilisable vehicles which are suitable for example, for example oral, or parenteral administration. Thus, tablets or gelatin capsules which contain the active substance together with diluents, for example lactose, dextrose, sucrose, mannitol, sorbitol, cellulose and/or lubricants, for example diatomaceous earth, talc, stearic acid or salts thereof, such as magnesium or calcium stearate, and/or polyethylene glycol, are used. Tablets can likewise contain binders, for example magnesium aluminium silicate, starches such as maize, wheat, rice or arrowroot starch, gelatine, tragacanth, methylcellulose, sodium carboxymethylcellulose and/or polyvinylpyrrolidone and, if desired, disintegrants, for example starches, agar, alginic acid or a salt thereof, for example sodium alginate, and/or effervescent mixtures, or absorbents, colorants, flavourings and sweeters. It is furthermore possible to use the novel compounds of the formula I in the form of products which can be administered parenterally or of infusion solutions. Solutions of this type are preferably isotonic aqueous solutions or suspensions, and these can, for example in the case of lyophilised products which contain the active substance alone or together with a vehicle, for example mannitol, be prepared before use. The pharmaceutical products can be sterilised and/or contain ancillary substances, for example preservatives, stabilisers, wetting agents and/or emulsifiers, solubilisers, salts to regulate the osmotic pressure and/or buffers. The present pharmaceutical products, which can, if required, contain further pharmacologically active substances, are prepared in a manner known per se, for example by conventional mixing, granulating, coating, dissolving or lyophilising processes, and contain from about 0.1% to 100%, in particular from about 1% to about 50%, lyophilisates up to about 100% of the active substance.

The invention likewise relates to the use of the compounds of the formula I, preferably in the form of pharmaceutical products. The dosage may depend on a variety of factors such as mode of administration, species, age and/or individual condition. The doses to be administered each day are an oral administration of between about 0.25 and about 10 mg/kg and, for warm-blooded animals with a body weight of about 70 kg, preferably between about 20 mg and about 500 mg.

The following examples serve to illustrate the invention; temperatures are indicated in degrees celsius, pressures in mbar.

EXAMPLE 1

(2R,4S) and (2R,4R)-2-Benzyl-1-(3,5-dimethylbenzoyl)-N-(2-phenethyl)-4-piperidinamine hydrochloride 1.26 g (17.1 mmol) of sodium cyanoborohydride (85%) are added in portions over the course of 10 minutes to a mixture of 3.65 g (11.4 mmol) of (2R,4RS)-2-benzyl-1-(3,5-dimethylbenzoyl)-4-piperidinamine in 30 ml of methanol, 935 mg (11.4 mmol) of sodium acetate, 0.65 ml (11.4 mmol) of acetic acid and 1.44 g (12 mmol) of phenylacetaldehyde under nitrogen at 0°. The reaction mixture is then stirred at room temperature for 3 hours, a further 0.376 g (2.4 mmol) of phenylacetaldehyde is added, and stirring is completed at 4° for 16 hours. The methanol is removed in a rotary evaporator, and the reddish reaction mixture is partitioned between ether and 1N sodium bicarbonate solution. The organic phases are washed with brine, dried over magnesium sulfate and evaporated to dryness. A mixture of the hydrochlorides of the title compounds of the formulae

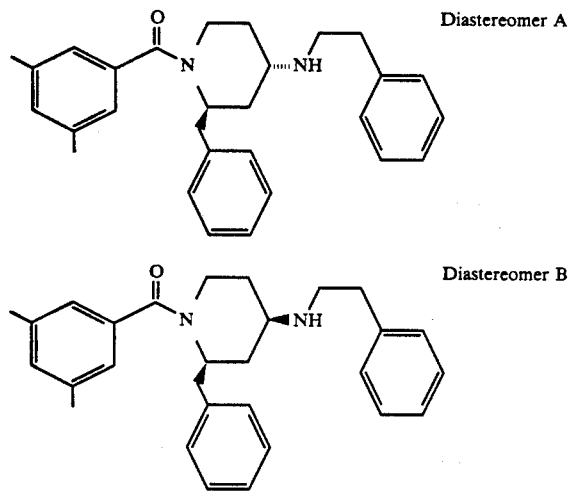

Diastereomer A

Diastereomer B is obtained as a yellow oil. This is chromatographed on silica gel to separate the diastereomers using the eluent mixture methylene chloride/methanol/conc. ammonia (97.5:2.25:0.25), and the diasterereomers are obtained pure as free bases.

TLC: methylene chloride/methanol (98:2)

Diastereomer A (2R,4R): $R_f=0.16$, melting point 248°–249° C., $[\alpha]_D = -56.9°$ (c=0.946,methanol), MS: M+ =426 (free base).

Diastereomer B (2R,4S): $R_f=0.06$, melting point 270° C. (decomposition), $[\alpha]_D = +30.6°$ (c=0.759, methanol), MS: M+ =426 (free base).

The starting compounds for this are prepared as follows:

a) Ethyl (R)-3-benzylamino-4-phenylbutyrate

A total of 19.1 g of sodium cyanoborohydride (0.304 mol) is added in portions to a solution of 42.2 g (0.203 mol) of ethyl (R)-3-amino-4-phenylbutyrate obtainable by esterification of the known (R)-3-amino-4-phenylbutyrate with ethanol, 11.6 ml (0.203 mol) of glacial acetic acid, 33.3 g (0.406 mol) of sodium acetate and 20.9 ml ((0.207 mol) of benzaldehyde in 400 ml of methanol at −5° to 5°. After the addition is complete, reaction is allowed to go to completion at room temperature for 1 hour. The yellow suspension is almost completely concentrated in a rotary evaporator, and the pasty residue is partitioned between ethyl acetate and water which is adjusted to about pH 8 with ammonia solution. The organic phases are washed with water and brine until neutral, dried over magnesium sulfate and evaporated to dryness, resulting in a yellow oil. This is chromatographed on silica gel with methylene chloride/methanol 99:1, resulting in the title compound of the formula as a pale yellow oil. The oxalate is obtained by adding oxalic acid to an ethereal solution of the title compound.

Melting point 142°–143°.

TLC: methylene chloride/methanol (95:5): $R_f=0.63$

MS: M+ −91=206 (60%)

$[\alpha]_D = +3°$ (c=1, Ethanol) free base $[\alpha]_D = -0.8°$ (c=1, CHCl$_3$) Oxalate $C_{21}H_{25}NO_6$(Oxalate): C calc. 65.11%, found 65.12% H calc. 6.51%, found 6.46% N calc. 3.62%, found 3.77%.

b) Methyl (R)-N-benzyl-N-[(1-ethoxycarbonylmethyl-2-phenyl)ethyl]carbamoyl-acetate A solution of 43.8 ml (0.408 mol) of methyl malonyl chloride in 480 ml of toluene is added dropwise over the course of 2½ hours to a solution, cooled in an ice-water bath, of 115.8 g (0.389 mol) of ethyl (R)-3-benzylamino-4-phenylbutyrate, 56.8 ml (0.408 mol) of triethylamine and 366 mg of dimethylaminopyridine in 630 ml of toluene so that the temperature remains within 0°–5°. The suspension is left to react to completion for 2 hours and then poured into 500 ml of ice-water. The organic phase is separated off, washed successively with 0.1N hydrochloric acid solution, 1N sodium bicarbonate solution and ice-water, and then dried over sodium sulfate and evaporated to dryness. The resulting yellow oil is chromatographed on silica gel with ethyl acetate/hexane (1:2), resulting in the title compound.

TLC: ethyl acetate/hexane (1:2), $R_f=0.25$

MS: M+ =397 (3%)

$[\alpha]_D = +19.5°$ (c=1.3, CHCl$_3$)

c) Methyl (6R)-1,6-dibenzyl-2,4-dioxo-3-piperidine carboxylate 15.2 g (0.135 mol) of potassium tertiary butanolate are added to a solution of 53.9 g (0.135 mol) of methyl (R)-N-benzyl-N-[(1-ethoxycarbonylmethyl-2-phenyl)ethyl]carbamoyl-acetate in 520 ml of tert.-butanol at room temperature and left to react to completion for 1 hour. The pale yellow suspension is mixed at room temperature with 1 equivalent (8.1 g) of glacial acetic acid and concentrated to a total volume of about 100 ml. The concentrate is diluted with 300 ml of water and extracted 3 times with 300 ml of ethyl acetate each time. The organic phases are subsequently washed with water and brine, and the combined organic phases are dried over sodium sulfate and evaporated to dryness, resulting in the title compound of a clear yellow oil which is used further without further purification; TLC. ethyl acetate/methanol (1:1); $R_f=0.3$.

d) (6R)-1,6-Dibenzyl-2,4-piperidinedione

A solution of 106.1 g (0.301 mol) of methyl (6R(-1,6-dibenzyl-2,4-dioxo3-piperidine carboxylate in 298 ml of toluene and 445 ml of 10% strength (vol/vol) acetic acid is heated at 80° for 2½ hours. The reaction mixture is cooled to room temperature, neutralised by adding 48 g of solid sodium carbonate while cooling in ice-water, the phases are separated, and the aqueous phase is extracted once more with 300 ml of ethyl acetate. The combined organic phases are washed with water, then with brine dried over sodium sulfate and evaporated to dryness. The resulting oil is crystallised from ether, resulting in the title compound.

Melting point 97°–97.5°

TLC: ethyl acetate/hexane (2:1), $R_f=0.31$ $[\alpha]_D: +166.9°$ (c=1, CHCl$_3$)

MS: M+ =293 (2.4%)

e) (2R,4RS)-1,2-Dibenzyl-4-piperidinamine (Variant e1)

e1a) 6R)-1,6-Dibenzyl-4-(methoxyimino)-2-piperidone

A solution of 10 g (0.034 mol) of (6R)-1,6-dibenzyl-2,4-piperidinedione in 68 ml of pyridine is mixed with 3.09 g (0.037 mol) of methoxyamine hydrochloride and heated at 85° for 1 h. The clear yellow solution is poured into ice-cold 1N hydrochloric acid solution (pH about 3) and extracted with toluene. The organic extracts are washed with 1N hydrochloric acid solution, then with 1N sodium carbonate solution and with brine. This is, followed by drying over sodium sulfate and evaporating to dryness, resulting in the title compound in the form of waxy crystals.

Melting point 63°–77°
TLC: ethyl acetate/hexane (1:1), $R_f$=0.52
MS: M+: 322 (1.4%)

On the basis of the $^1$H NMR (CDCl$_3$) a syn/anti mixture in the ratio of about 7:3 is present, methoxy signals of the oxime ether at 3.92 and 3.88 ppm.

e1b) (2R,4RS)-1,2-Dibenzyl-4-piperidinamine

A solution of 9.19 g (0.0285 mol) of (6R)-1,6-dibenzyl-4-(methoxyimino)-2-piperidone in 90 ml of tetrahydrofuran is heated to reflux under argon in a distillation apparatus with fitted Vigreux column and condenser through which water at 40° flows. To this solution are added dropwise over the course of 20 minutes 6.1 ml (0.0643 mol) of borane/dimethyl sulfide complex followed by a second addition of 9 ml (0.0949 mol) of borane/dimethyl sulfide complex over the course of 4 hours. During the addition of the borane/dimethyl sulfide complex, the liberated dimethyl sulfide escapes through the distillation apparatus.

After the addition is complete, the reaction mixture is cooled to 0°–4° in an ice-water bath, and excess borane is hydrolysed by slow addition of a total of 20 ml of methanol. After the vigorous, exothermic hydrolysis has subsided, the solvent is removed directly from the apparatus under water-pump vacuum. The residue is then boiled for 2 hours after addition of 90 ml of 5N hydrochloric acid solution. The solution is cooled to room temperature and diluted with 200 ml of water and extracted with ether to remove the acid and neutral portion, then the aqueous phase is cooled in an ice-water bath, adjusted to about pH 9 with 5N sodium hydroxide solution, and the base portion is extracted with ether/tetrahydrofuran (2:1). The organic extracts are dried over magnesium sulfate and evaporated to dryness, resulting in the crude base in the form of a yellowish oil. This is employed directly in the next stage; TLC: methylene chloride/methanol/conc. ammonia (90:10:0.4), $R_f$=0.3.

Amorphous dihydrochloride of the title compound is precipitated by dissolving in methanolic hydrochloric acid solution and adding ether; melting point 150°–182°.

Variant e2)

e2a) (6R)-1,6-Dibenzyl-2,4-piperidinedione 4-ethylene ketal

A solution of 30 g (0.102 mol) of (6R)-1,6-dibenzyl-2,4-piperidinedione, 50 ml of ethylene glycol and 1.8 g of p-toluenesulfonic acid monohydrate in 800 ml of toluene is heated with a water separator for 3 h. The solution is cooled to room temperature and washed with 100 ml of 1N sodium bicarbonate solution and brine, and the organic phase is dried over magnesium sulfate and evaporated to dryness, resulting in the crude ketal as oil. This is chromatographed on silica gel with ethyl acetate, and the oil resulting from the chromatography is crystallised from ether, resulting in the title compound in the form of white crystals.

Melting point 91°–93°
TLC: ethyl acetate/hexane (3:1), $R_f$=0.53
MS: M+: 337 e2b) (2R)-1,2-Dibenzyl-4-piperidone ethylene ketal 7.6 ml (0.0756 mol) of borane/dimethyl sulfide complex are added over the course of 10 minutes to a solution of 10.2 g (0.0302 mol) of (6R)-1,6-dibenzyl-2,4-piperidinedione 4-ethylene ketal in 100 ml of tetrahydrofuran under argon, and the mixture is heated to reflux for 1 h. The solution is cooled to room temperature and then 40 ml of 2N sodium hydroxide solution are added, and heating to reflux is resumed for 2 h, and subsequently the tetrahydrofuran is removed in a rotary evaporator and the reaction mixture is extracted with ether the organic extracts are washed with sodium bicarbonate, dried over magnesium sulfate and evaporated to dryness, resulting in the title compound; TLC: ethyl acetate/hexane (2:1), $R_f$=0.81; MS: M+: 323.

e2c) (2R)-1,2-Dibenzyl-4-piperidone

A solution of 85.7 g (0.261 mol) of (2R)-1,2-dibenzyl-4-piperidone ethylene ketal in 170 ml of dioxane and 1000 ml of 2.25M hydrochloric acid solution are heated at 70° for 29 hours. The dioxane is then removed in vacuo, the aqueous phase is adjusted to about pH 8 with 30% strength sodium hydroxide solution while cooling in ice-water and is extracted with ether the ether extracts are washed with 1N sodium bicarbonate solution, dried over sodium sulfate and evaporated to dryness, resulting in the title compound as a reddish oil which, because of its instability, is further processed without further purification; TLC: ethyl acetate/hexane (1:1); $R_f$=0.71; FD-MS: M+: 279 e2d) (2R)-1,2-Dibenzyl-4-(methoxyimino)piperidine 3 g (0.01071 mol) of (2R)-1,2-dibenzyl-4-piperidone, 4.4 g (0.0537 mol) of sodium acetate and 942 mg (0.0113 mol) of methoxyamine hydrochloride are dissolved in 30 ml of ethanol, and the suspension is heated at 60° for 30 minutes. The ethanol is then removed in vacuo, and the residue is partitioned between water and ethyl acetate, and the organic extracts are dried over sodium sulfate and evaporated to dryness, resulting in the crude product. This is chromatographed on silica gel with ethyl acetate/hexane (3:1), resulting in the title compound in the form of an oil.

TLC: ethyl acetate/hexane (1:1), $Rf_1$=0.84, $Rf_2$=0.76 (syn/anti oxime ethers)
MS: M+: 308 (1%), M+ −91:217 (90%).
$^1$H-NMR-spectrum (CD$_3$OD), δ(ppm)=3.85 (s, =N—OCH$_3$), 3.825 (s): approx. 1:1 e2e) (2R,4RS)-1,2-Dibenzyl-4-piperidinamine 180 ml of gaseous ammonia which has been dried over potassium hydroxide are condensed into a solution of 5.43 g (17.6 mmol) of (2R)-1,2-dibenzyl-4(methoxyimino)piperidine in 60 ml of tetrahydrofuran at −78°. To this solution are added at −70° 3.7 g (69 mmol) of ammonium chloride and, in portions, 1.6 g (70.4 mmol) of sodium metal. After one hour, a further 3.7 g of ammonium chloride and 0.6 g of sodium metal are added to the resulting suspension, which is then stirred at −70° for 2 hours. The cooling bath is then removed and the gaseous ammonia is allowed to evaporate. The residue is partitioned between 1N sodium hydroxide solution and ether, the organic phase is separated off, the aqueous phase is back-extracted, the organic phases are washed with brine, and the combined organic phases are dried over sodium sulfate and evaporated to dryness, resulting in the title compound in the form of a yellow oil; TLC: methylene chloride/methanol/conc. ammonia (90:9:1), $R_f$=0.33); MS: M+ =280.

f) (2R,4RS)-N-(1,2-Dibenzyl-4-piperidyl)trifluoroacetamide trifluoroacetate 5.1 ml (36.8 mmol) of trifluoroacetic anhydride are added to a solution of 6.88 g (24.5 mmol) of (2R,4RS)-1,2-dibenzyl-4-piperidinamine in 20 ml of methylene chloride in an ice-water bath, and stirring is then completed at room temperature for 1 hour. The reaction mixture is evaporated to dryness, resulting in the title compound as pale yellow foam; TLC: methylene chloride/methanovconc. ammonia (190:9:1), $R_f=0.41$ (cis) and 0.57 (trans) diastereomer; MS: M+ $-91$ (benzyl)=285 (14%).

g) (2R,4RS)-N-(2-Benzyl-4-piperidyl)trifluoroacetamide trifluoroacetate 3.0 g of 10% palladium catalyst on carbon are added to a solution of 19.3 g (39.4 mmol) of (2R,4RS)-N-(1,2-dibenzyl-4piperidyl)trifluoroacetamide trifluoroacetate in 160 ml of dioxane under nitrogen, and hydrogenation is carried out under atmospheric pressure at room temperature. The reaction mixture is freed of catalyst over Celite ® and the residue is washed with dioxane. The filtrate is evaporated to dryness and dried under high vacuum, resulting in the title compound which is used further without further purification; TLC: methylene chloride/methanol/conc. ammonia (90:9:1) $R_f=0.24$ and 0.3 (two poorly separated diastereomers)

h) (2R,4RS)-N-[2-Benzyl-1-(3,5-dimethylbenzoyl)-4-piperidyl]trifluoroacetamide 710 mg of solid sodium bicarbonate and 712 mg of 3,5-dimethylbenzoyl chloride are added to a stirred mixture of 1.39 g (3.44 mmol) of (2R,4RS)-N-(2-benzyl-4-piperidyl)trifluoroacetamide trifluoroacetate and 10 ml of toluene/water (1:1) cooled in ice-water. The reaction mixture is then allowed to warm to room temperature, subsequently stirred for 2 hours and partitioned between toluene and 1N sodium bicarbonate solution. The organic phases are washed with water, dried over magnesium sulfate and evaporated to dryness. The colourless oil is chromatographed on silica gel with ethyl acetate/hexane 1:2, resulting in the title compound. This is used further without further purification.

TLC: methylene chloride/methanol/conc. ammonia (190:9:1) $R_f=0.5$, (no separation of the two diastereomers under these conditions)

MS: M+=418 (3%), M+ 91 (43%)

i) (2R,4RS)-2-Benzyl-1-(3,5-dimethylbenzoyl)-4-piperidinamine 4.1 ml of 5N sodium hydroxide solution are added to a solution of 4.73 g (10.4 mmol) of (2R,4RS)-N-[2-benzyl-1-(3,5-dimethylbenzoyl)-4-piperidyl]trifluoroacetamide in 50 ml of tetrahydrofuran/methanol 1:1 at room temperature under nitrogen, and the mixture is heated to reflux for 3 hours. After the reaction is complete, the reaction mixture is cooled in ice-water, adjusted to about pH 1 with 1N hydrochloric acid solution, and the organic solvent is removed in a rotary evaporator. The remaining acidic aqueous phase is extracted first with ether to remove acidic and neutral portions, and is then adjusted to about pH 10 by adding 10N sodium hydroxide solution while cooling in ice-water and is extracted with ether. The organic phases are washed with brine, dried over sodium sulfate and evaporated to dryness, resulting in the free base as brownish oil, which is used further without purification; TLC: methylene chloride/methanol/conc. ammonia (90:9:1) $R_f=0.29$; MS: M+=322 (0.03%), M+$-91=231$ (62%).

(2S,4RS)2-Benzyl-1-(3,5-dimethylbenzoyl)-4-piperidinamine is obtained analogously thereto starting from L-phenylalaninol in accordance with the above reaction sequence.

EXAMPLE 2

(2R*,4S*)-2-Benzyl-1-(2-naphthoyl)-N-(4-quinolylmethyl)-4-piperidinamine 28 mg (0.73 mmol) of sodium borohydride are added in three portions over the course of 20 minutes to a solution of 106 mg (0.182 mmol) of (2R*,4S*)-2-benzyl-1-(2-naphthoyl)-N-(4-quinolylmethyl)-N-trifluoroacetyl-4-piperidinamine in 1.5 ml of methanol at 0°, and the mixture is subsequently stirred at 0° for 3 hours. 0.06 ml (0.81 mmol) of acetone is then added to the reaction mixture, and the stirring is completed for 10 minutes. The methanol is removed in a rotary evaporator, and the solid white residue is partitioned between ethyl acetate and water. The organic phases are washed with brine, dried over magnesium sulfate and evaporated to dryness. The resulting white foam is chromatographed with methylene chloride/methanol/conc. ammonia (1500:50:1) on silica gel. The title compound of the formula

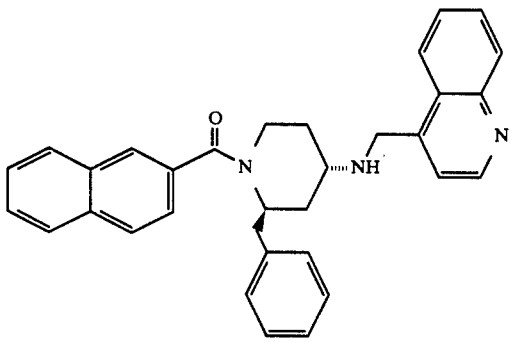

as white foam is obtained as white foam. TLC: methylene chloride/methanol/conc. ammonia (700:50:1) $R_f=0.34$, FD-MS: M+=485.

The starting compound for this is prepared as follows:

a) 2-Benzyl-N-benzyloxycarbonyl-2,3-dihydro-4-(1H)-pyridone 165 ml (1.16 mol) of benzyl chloroformate are added dropwise over the course of 20 minutes to a solution of 104 g (0.95 mol) of 4-methoxypyridine in 1 l of anhydrous tetrahydrofuran at $-70°$ under argon. The thick beige suspension is then diluted with 200 ml of anhydrous tetrahydrofuran. The Grignard reagent prepared from 460 ml (1.46 mol) of a 3 molar solution of benzyl chloride in anhydrous ether and 35.5 g (1.46 mol) of magnesium turnings in 160 ml of anhydrous ether is then added dropwise to the reaction mixture over the course of 75 minutes, maintaining the temperature at $-70°$. After a further 10 minutes, it is allowed to warm to room temperature. It is diluted with 500 ml of ether, 900 ml of 4N hydrochloric acid are added dropwise, and the phases are separated. The organic phases are washed with water and brine, dried over magnesium sulfate and evaporated to dryness. The residue is chromatographed on silica gel with hexane/ethyl acetate (3:1). The title compound is obtained as a colourless viscous oil. TLC: hexane/ethyl acetate (1:3) $R_f=0.7$, IR: 1725, 1665, 1602 cm$^{-1}$.

b) (2R*,4R*)-2-Benzyl-4-hydroxypiperidine 150 g (0.467 mol) of 2-benzyl-N-benzyloxycarbonyl-2,3-dihydro-4-(1H)-pyridone in 1.5 l of methanol are hydrogenated with 7.5 g of Pd/C (10%) as catalyst, then 50 g of Raney nickel and a further 200 ml of methanol are added, and hydrogenation is left to go to completion. Filtration is followed by evaporation in a rotary evaporator, and the brownish oil is chromatographed on silica gel with methylene chloride/methanol/conc. ammonia (60:10:1). The title compound is obtained as a semi-crystalline mass which is used further without additional purification. Crystallisation of a sample from ether/hexane yielded white crystals of melting point 111°–112°. TLC: methylene chloride/methanol/conc. ammonia (40:10:1) $R_f=0.55$, FD-MS: $M^+=191$.

c) (2R*,4R*)-2-Benzyl-1-t-butyloxycarbonyl-4-hydroxy-piperidine

A solution of 28 g (146 mmol) of (2R*,4R*)-2-benzyl-2-hydroxypiperidine and 35.1 g (161 mmol) of di-tert-butyl dicarbonate in 500 ml of chloroform is stirred at 50° for 20 hours. It is then concentrated in a rotary evaporator, and the yellow oil is chromatographed on silica gel with methylene chloride/methanol/conc. ammonia (2000:50:1). The title compound is obtained as yellow oil. TLC: methylene chloride/methanol/conc. ammonia (2000:50:1) $R_f=0.43$, FD-MS: $M^+=291$.

d) (2R*,4R*)-2-Benzyl-1-t-butyloxycarbonyl-4-methanesulfonyloxy-hydroxypiperidine 33.3 ml (428 mmol) of methanesulfonyl chloride are added dropwise to a solution of 62.4 g (214 mmol) of (2R*,4R*)-2-benzyl- 1-t-butyloxycarbonyl-4-hydroxypiperidine in 75 ml of pyridine while cooling in ice. After 30 minutes at 0°, stirring of the suspension is completed at room temperature for 3 hours. After concentration in a rotary evaporator, the reaction mixture is taken up in ethyl acetate, washed with water and brine, dried over magnesium sulfate and evaporated in a rotary evaporator. The title compound crystallises from ether as white crystals; melting point 110°–115°; TLC: toluene/ethyl acetate (4:1) $R_f=0.42$, FD-MS: $M^+=369$.

e) (2R*,4S*)-2-Benzyl-1-t-butyloxycarbonyl-4-piperidine azide

A mixture of 98.9 g (267 mmol) of (2R*,4R*)-2-benzyl-1-t-butyloxycarbonyl-4-methansulfonyloxy-hydroxypiperidine, 14.4 g (294 mmol) of lithium azide and 500 ml of N,N-dimethylformamide is stirred at 80° under argon for 3 hours. The reaction mixture is diluted with ethyl acetate and washed with water and brine, dried over magnesium sulfate and evaporated to dryness. The brownish oil is chromatographed on silica gel with toluene/ethyl acetate (9:1) as eluent. The title compound is obtained mixed with 2-benzyl-N-t-butyloxycarbonyl-1,2,5,6-tetrahydropyridine (ratio=4.2:1 by weight according to $^1$HNMR) which is not fractionated further. TLC: toluene/ethyl acetate (9:1) $R_f=0.59$, FD-MS: $M^+=316$, IR: 2100, 1685 cm$^{-1}$.

f) (2R*,4S*)-2-Benzyl-1-t-butyloxycarbonyl-4-piperidinamine

A mixture of 4.16 g (13.1 mmol) of (2R*,4S*)-2-benzyl-1-t-butyloxycarbonyl-4-piperidine azide and 0.99 g (3.62 mmol) of 2-benzyl-N-t-butyloxycarbonyl-1,2,5,6-tetrahydropyridine (calculated on the basis of the $^1$H-NMR spectrum) in 100 ml of methanol is hydrogenated with hydrogen and 1 g of 10% Pd/C. After the hydrogen uptake is complete, the mixture is filtered and evaporated in a rotary evaporator. The brown oil is chromatographed on silica gel with methylene chloride/methanol/conc. ammonia (350:50: 1). The title compound is obtained as a yellow oil. TLC: methylene chloride/methanol/conc. ammonia (350:50:1) $R_f=0.4$, FD-MS: $M^+=290$.

g) (2R*,4S*)-2-Benzyl-1-t-butyloxycarbonyl-N-(4-guinolylmethyl)-4-piperidinamine A mixture of 5 g (17.2 mmol) of (2R*,4S*)-2-benzyl-1-t-butyloxycarbonyl-4-piperidinamine and 2.7 g (17.2 mmol) of quinoline-4-carboxaldehyde in 50 ml of toluene is stirred at room temperature and, after 2 hours, 2.8 g (23.3 mmol) of anhydrous magnesium sulfate are added. After a further 16 hours, the mixture is filtered and the filtrate is concentrated. The brown oil is dissolved in 50 ml of methanol, and 0.69 g (1 8.3 mmol) of sodium borohydride is added in 4 portions. After stirring at room temperature for 3 hours, the reaction mixture is concentrated, taken in ethyl acetate and washed with water and brine. The organic phases are dried over magnesium sulfate and evaporated to dryness. The brown oil is chromatographed on silica gel with methylene chloride/methanol/conc. ammonia 850:50:1). The title compound is obtained as yellow oil. TLC: methylene chloride/methanol/conc. ammonia (700:50:1) $R_f=0.38$, FD-MS: $M^+=431$.

h) (2R*,4S*)-2-Benzyl-1-t-butyloxycarbonyl-N-(4-quinolylmethyl)-N-trifluoroacetyl-4-piperidinamine 2.2 ml (15.8 mmol) of trifluoroacetic anhydride are added to a solution of 6.2 g (14.4 mmol) of (2R*,4S*)-2-benzyl-1-t-butyloxycarbonyl-N-(4-quinolylmethyl)-4-piperidinamine and 2.6 ml (1 8.7 mmol) of triethylamine in 60 ml of methylene chloride at 0° under argon, and the reaction mixture is stirred at 0° for 3 hours. It is diluted with methylene chloride and washed with water. The organic phases are dried over magnesium sulfate and evaporated to dryness. The title compound is obtained as TLC-pure product as yellow oil. TLC: methylene chloride/methanol/conc. ammonia (700:50:1) $R_f=0.62$, DCI-MS: $(M+H)^+=528$.

i) (2R*,4S*)-2-Benzyl-N-(4-quinolylmethyl)-N-trifluoroacetyl-4-piperidinamine 250 n-A of 6N hydrogen chloride in dioxane is added dropwise over the course of 3 minutes to 7.73 g (14.7 mmol) of (2R*,4S*)-2-benzyl-1-t-butyloxycarbonyl-N-(4-quinolylmethyl)-N-trifluoroacetyl-4-piperidinamine while cooling in ice, and the mixture is subsequently stirred at room temperature for 1 hour. The reaction mixture is concentrated in a rotary evaporator, basified with 1N sodium bicarbonate solution and extracted with methylene chloride. The organic phases are dried over magnesium sulfate and evaporated to dryness. The brownish oil (7.14 g) is chromatographed on silica gel with methylene chloride/methanol/conc. ammonia (700:50:1). The title compound is obtained as yellow oil. TLC: methylene chloride/methanol/conc. ammonia (700:50:1) $R_f=0.42$, DCI-MS: $(M+H)^+=428$, IR: 1690 cm$^{-1}$.

j) (2R*,4S*)-2-Benzyl-1-(2-naphthoyl)-N-(4-quinolylmethyl)-N-trifluoroacetyl-4-piperidinamine A solution of 58 μl (0.795 mmol) of thionyl chloride in 0.2 ml of toluene is added dropwise to a solution of 97 mg (0.56 mmol) of 2-naphthoic acid in 1 ml of toluene over the course of 10 minutes at 50° under argon, and the reaction mixture is stirred at 80° for 2 hours. It is then concentrated in a rotary evaporator, and 1 ml of toluene is added, and evaporation is repeated, twice each. The brown oil is dissolved in 1 ml of methylene chloride and added under argon to a solution of 200 mg (0.468 mmol) of (2R*,4S*)-2-benzyl-N-(4-quinolylmethyl)-N-trifluoroacetyl-4-piperidinamine at 0° and stirred at 0° for 2 hours. Water is subsequently added to the reaction mixture, and extraction with methylene chloride is carried out. The organic phases are washed with brine, dried over magnesium sulfate and evaporated to dryness. The yellow oil is chromatogaphed on silica gel with methylene chloride/methanol/conc. ammonia (1000:50:1). The title compound is obtained as yellow oil. TLC: methylene chloride/methanol/conc. ammonia (2000:50:1) $R_f=0.36$, FD-MS: M+ =581.

EXAMPLE 3

2R*,4S*)-2-benzyl-1-(3-trifluoromethylbenzoyl)-N-(4-guinolylmethyl)-4-piperidinamine 0.184 g (0.307 mmol) of (2R*,4S*)-2-benzyl-1-(3-trifluoromethylbenzoyl)-N-(4-quinolylmethyl)-N-trifluoroacetyl-4-piperidinamine is reacted with 0.046 g (1.23 mmol) of sodium borohydride in analogy to Example 2. The title compound of the formula

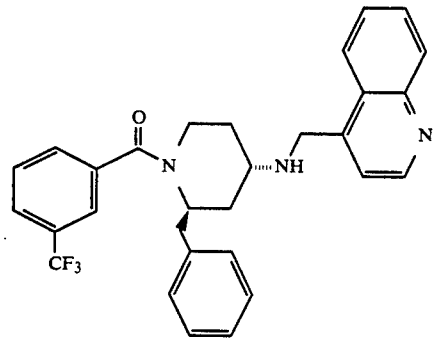

is obtained as yellow oil. TLC: methylene chloride/methanol/conc. ammonia (700:50:1) $R_f=0.28$, FD-MS: M+ =503.

The starting compound for this is prepared as follows:

(2R*,4S*)-2-Benzyl-1-(3-trifluoromethylbenzoyl)-N-(4-quinolylmethyl)-N-trifluoroacetyl-4-piperidinamine 106 mg (0.56 mmol) of 3-trifluoromethylbenzoic acid are reacted in analogy to Example 2j first with 58 µl (0.795 mmol) of thionyl chloride and subsequently with 200 mg (0.468 mmol) of (2R*,4S*)-2-benzyl-N-(4-quinolylmethyl)-N-trifluoroacetyl-4-piperidinamine to give the product. TLC: methylene chloride/methanol/-conc. ammonia (700:50:1) $R_f=0.56$, FD-MS: M+ =599.

EXAMPLE 4

(2R*,4S*)-2-benzyl-1-(3,5-bis-(trifluoromethyl)-benzoyl)-N-(4-quinolylmethyl)-4-piperidinamine 0.271 g (0.406 mmol) of (2R*,4S*)-2-benzyl-1-(3,5-bis-(trifluoromethyl)-benzoyl)-N-(4-quinolylmethyl)-N-trifluoroacetyl-4-piperidinamine is reacted with 0.061 g (1.23 mmol) of sodium borohydride in analogy to Example 2. The title compound

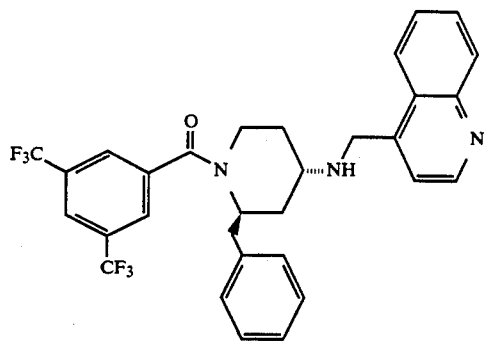

is obtained as white foam. TLC: methylene chloride/-methanol/conc. ammonia (1000:50:1) $R_f=0.21$, FD-MS: M+ =571.

The starting compound for this is prepared as follows:

(2R*,4S*)-2-Benzyl-1-(3,5-bis-(trifluoromethyl)-benzoyl)-N-(4-quinolylmethyl)-N-trifluoroacetyl-4-piperidinamine 143 mg (561 mmol) of bis-(2-oxo-3-oxazolidinyl)phosphinic chloride and 144 µl (1.03 mmol) of triethylamine are added to a solution of 200 mg (467 mmol) of (2R*,4S*)-2-benzyl-N-(4-quinolylmethyl)-N-trifluoroacetyl-4-piperidinamine and 113 mg (561 mmol) of 3,5-bis-(trifluoromethyl)-benzoic acid in 3 ml of methylene chloride, and the reaction mixture is left to stir at room temperature for 16 hours. It is then diluted with methylene chloride, and the organic phase is washed once each with 10% strength citric acid, 1N sodium bicarbonate solution and with brine, dried over magnesium sulfate and evaporated to dryness. The yellowish foam is chromatographed on silica gel with methylene chloride/methanol/conc. ammonia (1000:50:1). The title compound is obtained as yellow oil. TLC: methylene chloride/methanol/conc. ammonia (1000: 50:1) $R_f=0.34$, FD-MS: M+ =667.

EXAMPLE 5

(2R*,4S*)-2-benzyl-1-(3,5-dimethoxybenzoyl)-N-(4-quinolylmethyl)-4-piperidinamine 250 mg (0.423 mmol) of (2R*,4S*)-2-benzyl-1-(3,5-dimethoxybenzoyl)-N-(4-quinolylmethyl)-N-trifluorpacetyl-4-piperidinamine are reacted with 64 mg (1.69 mmol) of sodium borohydride in analogy to Example 2. The title compound

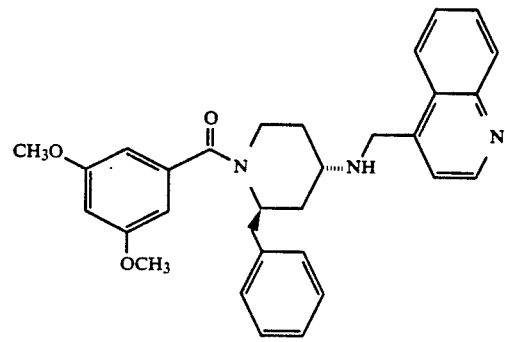

is obtained as white foam. TLC: methylene chloride/methanol/conc. ammonia (1000:50:1) R$_f$=0.23, DCI-MS: (M+H)+ =496.

The starting compound for this is prepared as follows:

(2R*,4S*)-2-Benzyl-1-(3,5-dimethoxybenzoyl)-N-(4-guinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted with 102 mg (0.561 mmol) of 3,5-dimethoxybenzoic acid, 143 mg (0.561 mmol) of bis(2-oxo-3-oxazolidinyl)phosphinic chloride and 144 μl (1.03 mmol) of triethylamine in analogy to Example 4. The title compound is obtained as white foam. TLC: methylene chloride/methanol/conc. ammonia (1000:50:1) R$_f$=0.31, FD-MS: M+ =591.

EXAMPLE 6

(2R*,4S*)-2-benzyl-1-(1-naphthoyl)-N-(4-quinolylmethyl)-4-piperidinamine 200 mg (0.344 mmol) of (2R*,4S*)-2-benzyl-1-(1-naphthoyl(-N-(4-quinolylmethyl)-N-trifluoroacetyl-4-piperidinamine are reacted with 52 mg (1.37 mmol) of sodium borohydride in analogy to Example 2. The title compound

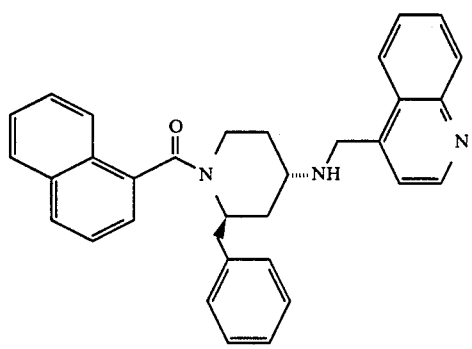

is obtained as white foam. TLC: methylene chloride/methanol/conc. ammonia (1000:50:1) R$_f$=0.35, FD-MS: M+ =485.

The starting compound for this is prepared as follows:

(2R*,4S*)-2-Benzyl-1-(1-naphthoyl)-N-(4-guinolylmethyl)-N-trifluoroacetyl-4-piperidinamine 92 μl (0.655 mmol) of 1-chloro-N,N,2-trimethyl-1-propen-1-amine are added to a solution of 96 mg (0.561 mmol) of 1-naphthoic acid in 2 ml of dry methylene chloride at 0°, and the mixture is stirred at 0° for 1 hour and at room temperature for 1 hour. Subsequently a solution of 200 mg (0.468 mmol) of (2R*,4S*)-2-benzyl-N-(4-quinolylmethyl)-N-trifluoroacetyl-4-piperidinamine and 130 μl (0.936 mmol) of triethylamine in 3 ml of methylene chloride is added dropwise over the course of 10 minutes to this yellow solution at room temperature. After stirring at room temperature for 3 hours, water is added, the organic phase is separated off and washed twice more with water. The organic phases are dried over magnesium sulfate and evaporated to dryness. The yellow oil is chromatographed on silica gel with methylene chloride/methanol/conc. ammonia (800:50:1). The title compound is obtained as yellow oil.

TLC: methylene chloride/methanol/conc. ammonia (700:50:1) R$_f$=0.49, FD-MS: M+ =581.

EXAMPLE 7

(2R*,4S*)-2-benzyl-1-(3,5-dichlorobenzoyl)-N-(4-quinolylmethyl)-4-piperidinamine 1.21 g (2.01 mmol) of (2R*,4S*)-2-benzyl-1-(3,5-dichlorobenzoyl)-N-(4-quinolylmethyl)-N-trifluoroacetyl-4-piperidinamine are reacted with 0.305 mg (8.06 mmol) of sodium borohydride in analogy to Example 2. The title compound

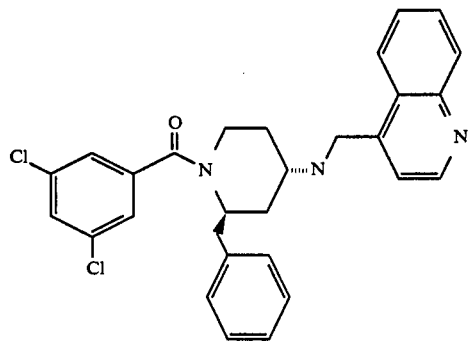

is obtained as white foam; TLC: methylene chloride/methanol/conc. ammonia (700:50:1) R$_f$=0.37; FD-MS: M+ =503.

The starting compound for this is prepared as follows:

(2R*,4S*)-2-Benzyl-1-(3,5-dichlorobenzoyl)-N-(4-quinolylmethyl)-N-trifluoroacetyl-4-piperidinamine 1.11 g (5.85 mmol) of 3,5-dichlorobenzoic acid are reacted in analogy to Example 2j first with 0.63 nil (8.77 mmol) of thionyl chloride and subsequently with 1 g (2.34 mmol) of (2R*,4S*)-2-benzyl-N-(4-quinolylmethyl)-N-trifluoroacetyl-4-piperidinamine to give the product. TLC: methylene chloride/methanol/conc. ammonia (700:50:1) R$_f$=0.65, FD-MS: M+ =599.

EXAMPLE 8

(2R*,4S*)-2-benzyl-1-(2-quinolinylcarbonyl)-N-(4-guinolylmethyl)-4-piperidinamine 155 mg (0.266 mmol) of (2R*,4S*)-2-benzyl-1-(2-quinolinylcarbonyl)-N-(4-quinolylmethyl)-N-trifluoroacetyl-4-piperidinamine are reacted with 40 mg (1.06 mmol) of sodium borohydride in analogy to Example 2. The title compound

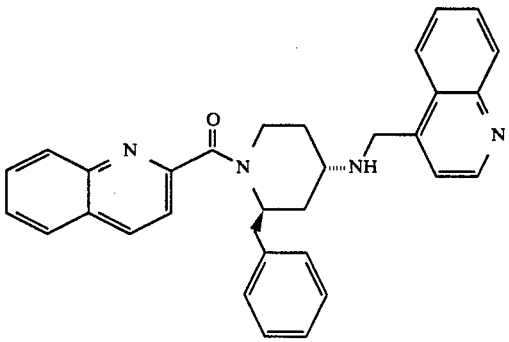

is obtained as white foam. TLC: methylene chloride/methanol/conc. ammonia (700:50:1) R$_f$=0.42, FD-MS: M+ =486.

The starting compound for this is prepared as follows:

(2R*,4S*)-2-Benzyl-1-(2-quinolinylcarbonyl)-N-(4-quinolylmethyl)-N-trifluoroacetyl-4-piperidinamine 97 mg (0.56 mmol) of quinoline-2-carboxylic acid are reacted in analogy to Example 2j first with 58 μl (0.795 mmol) of thionyl chloride and subsequently with 200 mg (0.468 mmol) of (2R*,4S*)-2-benzyl-N-(4-quinolylmethyl)-N-trifluoroacetyl-4-piperidinamine to give the product. TLC: methylene chloride/methanol/conc. ammonia (700:50:1) R$_f$=0.45, FD-MS: M+ =582.

EXAMPLE 9

(2R*,4S*)-2-benzyl-1-(4-chlorophenylacetyl)-N-(4-guinolylmethyl)-4-piperidinamine 256 mg (0.441 mmol) of (2R*,4S*)-2-benzyl-1-(4-chlorophenylacetyl)-N-(4-quinolylmethyl)-N-trifluoroacetyl-4-piperidinamine are reacted with 66 mg (1.76 mmol) of sodium borohydride in analogy to Example 2. The title compound

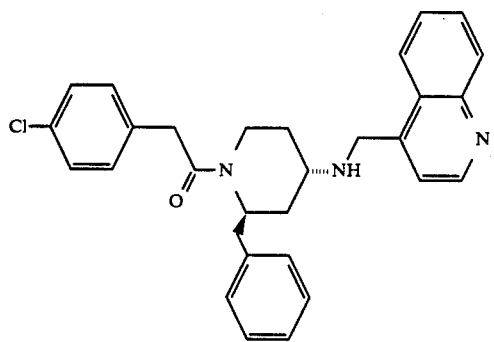

is obtained as white foam. TLC: methylene chloride/methanol/conc. ammonia (700:50:1) R$_f$=0.48, FD-MS: M+ =484.

The starting compound for this is prepared as follows:

(2R*,4S*)-2-Benzyl-1-(4-chlorophenylacetyl)-N-(4-quinolylmethyl)-N-trifluoroacetyl-4-piperidinamine 96 mg (0.56 mmol) of 4-chlorophenylacetic acid are reacted in analogy to Example 2j first with 58 μl (0.795 mmol) of thionyl chloride and subsequently with 200 mg (0.468 mmol) of (2R*,4S*)-2-benzyl-N-(4-quinolylmethyl)-N-trifluoroacetyl-4-piperidinamine to give the product. TLC: methylene chloride/methanol/conc. ammonia (700:50:1) R$_f$=0.39, FD-MS: M+ =580.

EXAMPLE 10

I(2R*,4S*)-2-benzyl-1-(benzyloxycarbonyl)-N-(4-guinolylmethyl)-4-piperidinamine 80 mg (0.142 mmol) of (2R*,4S*)-2-benzyl-1-(benzyloxycarbonyl)-N-(4-quinolylmethyl)-N-trifluoroacetyl-4-piperidinamine are reacted with 22 mg (0.57 mmol) of sodium borohydride in analogy to Example 2. The title compound

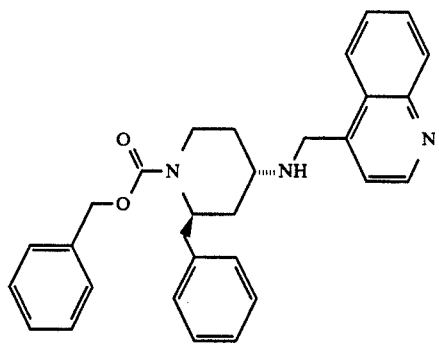

is obtained as colourless oil. TLC: methylene chloride/methanol/conc. ammonia (700:50:1) R$_f$=0.43, FD-MS: M+ =465.

The starting compound for this is prepared as follows:

(2R*,4S*)-2-Benzyl-1-(benzyloxycarbonyl)-N-(4-quinolylmethyl)-N-trifluoroacetyl-4-piperidinamine 67 μl (0.468 mmol) of benzyl chloroformate and 72 μl (0.515 mol) of triethylamine are added to a solution of 200 mg (0.468 mmol) of (2R*,4S *)-2-benzyl-N-(4-quinolylmethyl)-N-trifluoroacetyl-4-piperidinaniine in 4 ml methylene chloride at 0°, and the mixture is left to stir at this temperature for 16 hours. Then a further 34 μl (0.234 mmol) of benzyl chloroformate and 36 μl (0.257 mmol) of triethylamine are added and stirred at room temperature for 3 hours. This is followed by dilution with methylene chloride, and the organic phase is washed with brine, dried over magnesium sulfate and evaporated to dryness. The oil is chromatographed on silica gel with methylene chloride/methanol/conc. ammonia (1000:50:1). The title compound is obtained as oil. TLC: methylene chloride/methanol/conc. ammonia (700:50:1) Rf=0.61, FD-MS: M+ =561.

EXAMPLE 11

(2R*,4S*)-2-benzyl-1-(2-phenylethyl)-N-(4-guinolylmethyl)-4-piperidinamine 215 mg (0.494 mmol) of (2R*,4S*)-2-benzyl-1-(2-phenylethyl)-N-(4-quinolylmethyl)-N-trifluoroacetyl-4-piperidinamine are reacted with 77 mg (1.97 mmol) of sodium borohydride in analogy to Example 2. The title compound

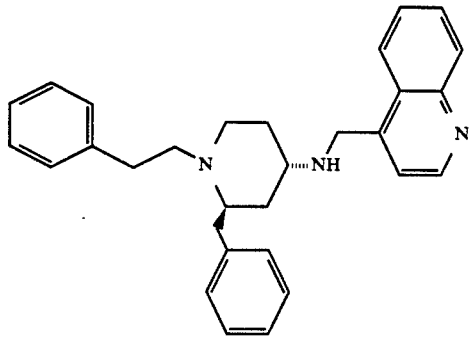

is obtained as oil. TLC: methylene chloride/methanol/conc. ammonia (700:50:1) R$_f$=0.34, FD-MS: M+ =435.

The starting compound for this is prepared as follows:

(2R*,4S*)-2-Benzyl-1-(2-phenylethyl)-N-(4-quinolylmethyl)-N-trifluoroacetyl-4-piperidinamine 209 μl (0.936 mmol) of phenylacetaldehyde are added dropwise over the course of 10 minutes to a solution of 100 mg (0.233 mmol) of (2R*,4S*)-2-benzyl-N-(4-quinolylmethyl)-N-trifluoroacetyl-4-piperidinamine, 58 mg (0.702 mmol) of sodium acetate, 44 mg (0.702 mmol) of sodium cyanoborohydride and 67 μl (1.17 mmol) of acetic acid in 2 ml of ethanol at room temperature. The reaction mixture is left to stir at room temperature for 16 hours. The residue after evaporation in a rotary evaporator is taken up in ethyl acetate, and the organic phase is washed with water and with brine, dried over magnesium sulfate and evaporated to dryness. The yellow oil is chromatographed on silica gel with methylene chloride/methanol/conc. ammonia (2000:50:1). The title compound is obtained as oil. TLC: methylene chloride/methanol/conc. ammonia (2000:50:1) R$_f$=0.33, FD-MS: M+ =531.

EXAMPLE 12

(2R*,4S*)-2-benzyl-1-(2-naphthylacetyl)-N-(4-quinolylmethyl)-4-piperidinamine 160 mg (0.269 mmol) of (2R*,4S*)-2-benzyl-1-(2-naphthylacetyl)-N-(4-quinolylmethyl)-N-trifluoroacetyl-4-piperidinamine are reacted with 42 mg (1.13 mmol) of sodium borohydride in analogy to Example 2. The title compound

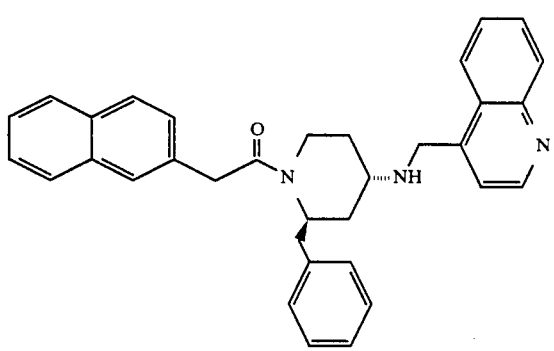

is obtained as colourless oil. TLC: methylene chloride/methanol/conc. ammonia (700:50:1) R$_f$=0.27, FD-MS: M+ =499.

The starting compound for this is prepared as follows:

(2R*,4S*)-2-Benzyl-1-(2-naphthylacetyl)-N-(4-quinolylmethyl)-N-trifluoroacetyl-4-piperidinamine 105 mg (0.561 mmol) of 2-naphtylacetic acid are reacted in analogy to Example 6 first 92 μl (0.655 mmol) of 1-chloro-N,N,2-trimethyl-1-propen-1-amine and subsequently with 200 mg (0.468 mmol) of (2R*,4S*)-2-benzyl-N-(4-quinolylmethyl)-N-trifluoroacetyl-4-piperidinamine and 130 μl (0.936 mmol) of triethylamine to give the product. TLC: methylene chloride/methanol/conc. ammonia (700:50:1) R$_f$=0.56, FD-MS: M+ =595.

EXAMPLE 13

(2R*,4S*)-2-benzyl-1-(4-quinolylmethyl)-N-(4-quinolylmethyl)-4-piperidinamine 128 mg (0.225 mmol) of (2R*,4S*)-2-benzyl-1-(4-quinolylmethyl) N-(4-quinolylmethyl)-N-trifluoroacetyl-4-piperidinamine are reacted with 34 mg (0.872 mmol) of sodium borohydride in analogy to Example 2. The title compound

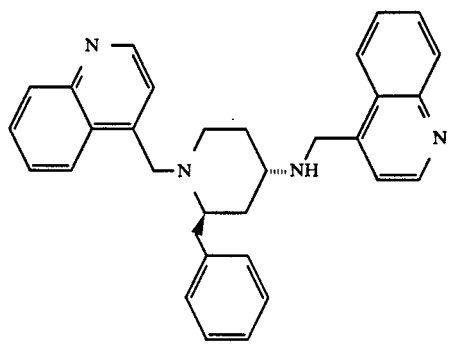

is obtained as yellow oil. TLC: methylene chloride/methanol/conc. ammonia (700:50:1) R$_f$=0.45, FD-MS: M+ =490.

The starting compound for this is prepared as follows:

(2R*,4S*)-2-Benzyl-1-(4-quinolylmethyl)-N-(4-guinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 11 with 88 mg (1.4 mmol) of sodium cyanoborohydride, 115 mg (1.4 mmol) of sodium acetate, 134 μl (2.34 mmol) of acetic acid and 294 mg (1.87 mmol) quinoline-4-carboxaldehyde to give the product. TLC: methylene chloride/methanol/conc. ammonia (700:50:1) R$_f$=0.33, FD-MS: M+ =568.

EXAMPLE 14

(2R*,4S*)-2-benzyl-1-(214-dichlorobenzyl)-N-(4-quinolylmethyl)-4-piperidinamine 128 mg (0.218 mmol) of (2R*,4S*)-2-benzyl-1-(2,4-dichlorobenzyl)-N-(4-quinolylmethyl)-N-trifluoroacetyl-4-piperidinamine are reacted with 34 mg (0.920 mmol) of sodium borohydride in analogy to Example 2. The title compound

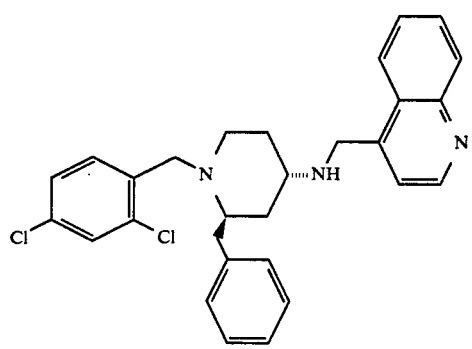

is obtained as yellow oil. TLC: methylene chloride/methanol/conc. ammonia (700:50:1) R_f=0.25, FD-MS: M+ =472.

The starting compound for this is prepared as follows:

(a) (2R*,4S*)-2-Benzyl-1-(4-quinolylmethyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 11 with 88 mg (1.4 mmol) of sodium cyanoborohydride, 115 mg (1.4 mmol) of sodium acetate, 134 μl (2.34 mmol) of acetic acid and 294 mg (1.87 mmol) of quinoline-4-carboxaldehyde to give the product. TLC: methylene chloride/methanol/conc. ammonia (700:50:1) R_f=0.33, FD-MS: M+ =568.

EXAMPLE 15

(2R*,4S*)-2-benzyl-1-(2,2-diphenylethyl)-N-(4-guinolylmethyl)-4-piperidinamine 170 mg (0.280 mmol) of (2R*,4S*)-2-benzyl-1-(2,2-diphenylethyl)-N-(4-quinolylmethyl)-N-trifluoroacetyl-4-piperidinamine are reacted with 42 mg (1.12 mmol) of sodium borohydride in analogy to Example 2. The title compound

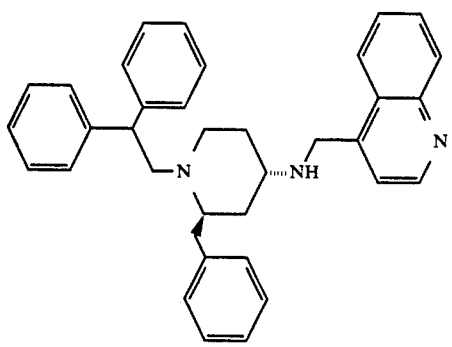

is obtained as white foam. TLC: methylene chloride/methanol/conc. ammonia (1000:50:1) R_f=0.28, FD-MS: M+ =511.

The starting compound for this is prepared as follows:

(2R*,4S)-2-Benzyl-1-(2,2-diphenylethyl)-N-(4-guinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 11 with 88 mg (1.4 mmol) of sodium cyanoborohydride, 115 mg (1.4 mmol) of sodium acetate, 134 μl (2.34 mmol) of acetic acid and 335 μl (1.87 mmol) of diphenylacetaldehyde with the product. TLC: methylene chloride/methanol/conc. ammonia (2000:50:1) R_f=0.50, FD-MS: M+ =607.

EXAMPLE 16

(2R*,4S*)-2-benzyl-1-(phenylcarbamoyl)-N-(4-quinolylmethyl)-4-piperidinamine 210 mg (0.384 mmol) of (2R*,4S*)-2-benzyl-1-(phenylcarbamoyl)-N-(4-quinolylmethyl)-N-trifluoroacetyl-4-piperidinamine are reacted with 58 mg (1.54 mmol) of sodium borohydride in analogy to Example 2. The title compound

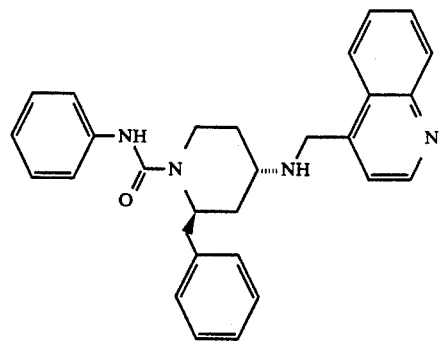

is obtained as white foam. TLC: methylene chloride/methanol/conc. ammonia (1000:50:1) R_f=0.33, FD-MS: M+ =450.

The starting compound for this is prepared as follows:

(2R*,4S*)-2-Benzyl-1-(phenylcarbamoyl)-N-(4-quinolylmethyl)-N-trifluoroacetyl-4-piperidinamine A solution of 200 mg (0.468 mmol) of (2R*,4S*)-2-benzyl-N-(4-quinolylmethyl)-N-trifluoroacetyl-4-piperidinamine is added to a solution of 72 mg (0.608 mmol) of phenyl isocyanate in 5 ml of toluene, and the reaction mixture is stirred at 100° for 2 hours. The white suspension is cooled and filtered. The tide compound is obtained as white crystals of melting point 245° (decomposition). TLC: methylene chloride/methanol/conc. ammonia (700:50:1) R_f=0.76, FD-MS: M+ =546.

EXAMPLE 17

(2R*,4S*)-2-benzyl-1-(diphenylacetyl)-N-(4-guinolylmethyl)-4-piperidinamine 235 mg (0.378 mmol) of (2R*,4S*)-2-benzyl-1-(diphenylacetyly-N-(4-quinolylmethyl)-N-trifluoroacetyl-4-piperidinamine are reacted with 58 mg (1.51 mmol) of sodium borohydride in analogy to Example 2. The title compound

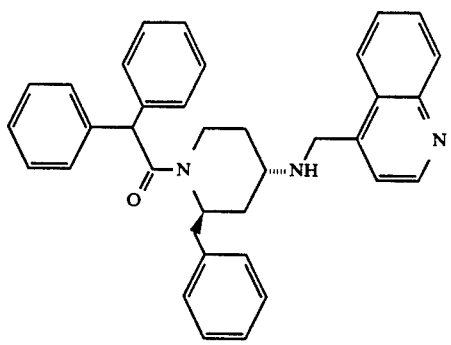

is obtained as white foam. TLC: methylene chloride/methanol/conc. ammonia (700:50:1) R_f=0.49, FD-MS: M+ =525.

The starting compound for this is prepared as follows:

(2R*,4S*)-2-Benzyl-1-(diphenylacetyl)-N-(4-quinolymethyl-N-trifluoroacetyl-4-piperidinamine 248 mg (1.17 mmol) of diphenylacetic acid are reacted in analogy to Example 2j first with 128 μl (1.76 mmol) of thionyl chloride and subsequently with 200 mg (0.468 mmol) of (2R*,4S*)-2-benzyl-N-(4-quinolylmethyl)-N-trifluoroacetyl-4-piperidinamine to give the product. TLC: methylene chloride/methanol/conc. ammonia (700:50:1) R$_f$=0.45, FD-MS: M+ =621.

EXAMPLE 18

(2R*,4S*)-2-benzyl-1-(2-pyridylaceytl)-N-(4-quinolylmethyl)-4-piperidinamine 180 mg (0.329 mmol) of (2R*,4S*)-2-benzyl-1-(2-pyridylacetyl)-N-(4-quinolylmethyl)-N-trifluoroacetyl-4-piperidinamine are reacted with 50 mg (1.32 mmol) of sodium borohydride in analogy to Example 2. The title compound

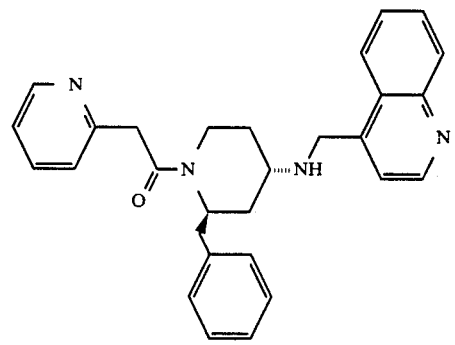

is obtained as white foam. TLC: methylene chloride/methanol/conc. ammonia (700:50:1) R$_f$=0.28, FD-MS: M+ =450.

The starting compound for this is prepared as follows:

(2R*,4S*)-2-Benzyl-1-(2-pyridylacetyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted in analogy to Example 4 with 98 mg (0.561 mmol) of 2-pyridylacetic acid hydrochloride, 143 mg (0.562 mmol) of bis-(2-oxo-3-oxazolidinyl)phosphinic chloride and 209 μl (1.50 mmol) of triethylamine. The title compound is obtained as white foam. TLC: methylene chloride/methanol/conc. ammonia (700:50:1) R$_f$=0.60, FD-MS: M+ =546.

EXAMPLE 19

(2R*,4S*)-2-benzyl-1-(4-pyridylacetyl)-N-(4-quinolylmethyl)-4-piperidinamine 200 mg (0.366 mmol) of (2R*,4S*)-2-benzyl-1-(4-pyridylacetyl)-N-(4-quinolylmethyl)-N-trifluoroacetyl-4-piperidinamine are reacted with 55 mg (1.46 mmol) of sodium borohydride in analogy to Example 2. The title compound

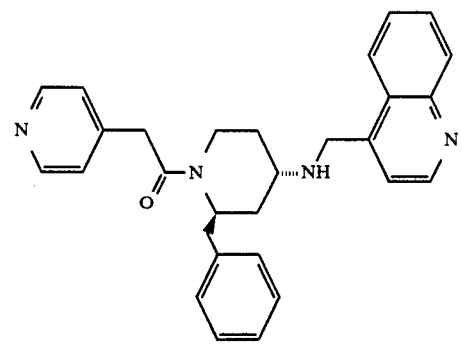

is obtained as white foam. TLC: methylene chloride/methanol/conc. ammonia (700:50:1) R$_f$=0.3 1, FD-MS: M+ =450.

The starting compound for this is prepared as follows:

(2R*,4S*)-2-Benzyl-1-(4-pyridylacetyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 4 with 98 mg (0.561 mmol) of 4-pyridylacetic acid hydrochloride, 143 mg (0.562 mmol) of bis-(2-oxo-3-oxazolidinyl)phosphinic chloride and 209 μl (1.50 mmol) of triethylaniine. The title compound is obtained as white foam. TLC: methylene chloride/methanol/conc. ammonia (700:50:1) R$_f$=0.56, FD-MS: M+ =546.

EXAMPLE 20

(2R*,4S*)-2-benzyl-1-(2,3-diphenylpropionyl)-N-(4-guinolylmethyl)-4-piperidinamine 340 mg (0.535 mmol) of (2R*,4S*)-2-benzyl-1-(2,3-diphenylpropionyl)-N-(4-quinolylmethyl)-N-trifluoroacetyl-4-piperidinamine are reacted with 81 mg (2.14 mmol) of sodium borohydride in analogy to Example 2. The title compound

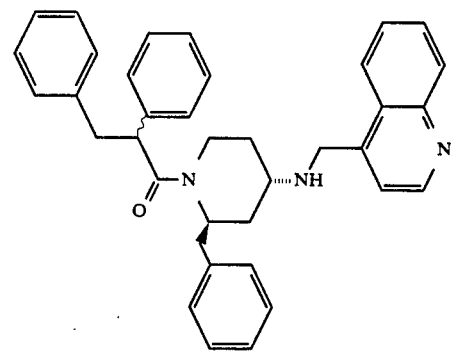

is obtained as mixture of diastereomers in the form of white foam. TLC: methylene chloride/methanol/conc. ammonia (1000:50:1) R$_f$=0.37, FD-MS: M+ =539.

The starting compound for this is prepared as follows:

(2R*,4S*)-2-Benzyl-1-(2,3-diphenylpropionyl)-N-(4-guinolylmethyl)-N-trifluoroacetyl-4-piperidinamine 300 mg (0.702 mmol) of (2R*,4S*)-2-benzyl-N-(4-quinolylmethyl)-N-trifluoroacetyl-4-piperidinamine are reacted in analogy to Example 4 with 190 mg (0.842 mmol) of (R,S)-2,3-diphenylpropionic acid, 214 mg (0.842 mmol) of bis-(2-oxo-3-oxazolidinyl)phosphinic chloride and 216 μl (1.54 mmol) of triethylamine. The title compound is obtained as white foam. TLC: methylene chloride/methanol/conc. ammonia (700:50:1) R$_f$=0.74, FD-MS: M+=635.

EXAMPLE 21

(2R*,4S*)-2-benzyl-1-((3S)-(2,3,4,9-tetrahydro-1H-pyrido[3,4-b]indol-3-yl)carbonyl)-N-(4-guinolylmethyl)-4-piperidinamine 197 mg (0.315 mmol) of the mixture of (2R*,4S*)-2-benzyl-1-((3S)-(2,3,4,9-tetrahydro-1H-pyrido[3,4-b]indol-3-yl)carbonyl)-N-(4-quinolylmethyl)-N-trifluoroacetyl-4-piperidinamine diastereomers are reacted with 48 mg (1.26 mmol) of sodium borohydride in analogy to Example 2. The title compound

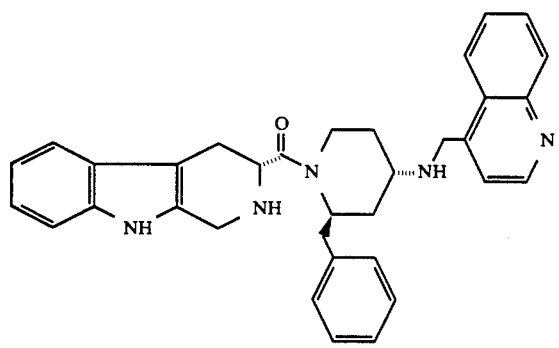

is obtained as mixture of diastereomers in the form of white foam. TLC: methylene chloride/methanol/conc. ammonia (350:50:1) R$_f$=0.50, FD-MS: M+=529.

The starting compounds for this are prepared as follows:

(2R*,4S*)-2-Benzyl-1-((3S)-(2,3,4,9-tetrahydro-1H-pyrido[3,4-b]indol-3-yl)carbonyl)-N-(4-quinolylmethyl)-N-trifluoroacetyl-4-piperidinamine 1.97 ml, 19.9 mmol) of piperidine are added to a solution of 338 mg (0.399 mmol) of (2R*,4S*)-2-benzyl-1-((3S)-(2-(9-fluorenylmethyloxycarbonyl)-2,3,4,9-tetrahydro-1H-pyrido[3,4-b]indol-3-yl)carbonyl)-N-(4-quinolymethyl)-N-trifluoroacetyl-4-piperidinamine in 3 ml of N,N-dimethylformamide, and the mixture is stirred at room temperature for 2 hours. It is then concentrated in a rotary evaporator, and the residue is chromatographed on silica gel with methylene chloride/methanol/conc. ammonia (2000:50:1) to separate the diastereomers. TLC: methylene chloride/methanol/conc. ammonia (700:50:1)
Diastereomer A:R$_f$=0.21, FD-MS: M+=625,
Diastereomer B:R$_f$=0.13, FD-MS: M+=625.

EXAMPLE 22

(2R*,4S*)-2-benzyl-1-(3-methoxybenzoyl)-N-(4-quinolylmethyl)- 4-piperidinamine 230 mg (0.409 mmol) of (2R*,4S*)-2-benzyl-1-(3-methoxybenzoyl)-N-(4-quinolylmethyl)-N-trifluoroacetyl-4-piperidinamine are reacted with 81 mg (2.14 mmol) of sodium borohydride in analogy to Example 2. The title compound of the formula

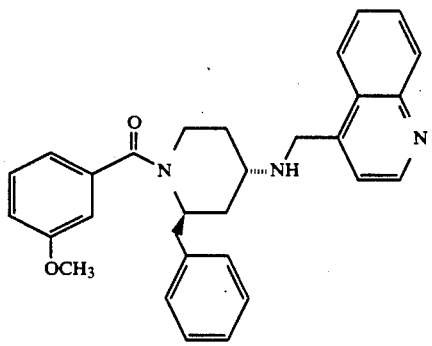

is obtained as white foam. TLC: methylene chloride/methanol/conc. ammonia (1000:50:1) R$_f$=0.26, FD-MS: M+=465.

The starting compound for this is prepared as follows:

(2R*,4S*)-2-Benzyl-1-(3-methoxybenzoyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 4 with 85 mg (0.561 mmol) of 3-methoxybenzoic acid, 143 mg (0.561 mmol) of bis-(2-oxo-3-oxazolidinyl)phosphinic chloride and 144 μl (1.03 mmol) of triethylamine. The title compound is obtained as white foam. TLC: methylene chloride/methanol/conc. ammonia (1000:50:1) R$_f$=0.45, FD-MS: M+=561.

EXAMPLE 23

2R*,4S*)-2-benzyl-1-(3-N,N-dimethylaminobenzoyl)-N-(4-quinolylmethyl)-4-piperidinamine 225 mg (0.391 mmol) of (2R*,4S*)-2-benzyl-1-(3-N,N-dimethylaminobenzoyl)-N-(4-quinolylmethyl)-N-trifluoroacetyl-4-piperidinamine are reacted with 59 mg (1.56 mmol) of sodium borohydride in analogy to Example 2. The title compound

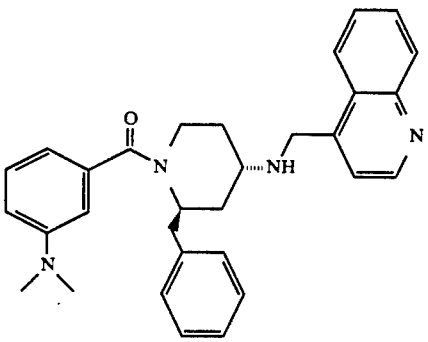

is obtained as white foam. TLC: methylene chloride/methanol/conc. ammonia (700:50:1) R$_f$=0.36, FD-MS: M+=478.

The starting compound for this is prepared as follows:

(2R*,4S*)-2-Benzyl-1-(3-N,N-dimethylaminobenzoyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 4 with 93 mg (0.561 mmol) of 3-N,N-dimethylaminobenzoic acid, 143 mg (0.561 mmol) of bis-(2-oxo-3-oxazolidinyl)phosphinic chloride and 144 μl (1.03 mmol) of triethylamine. The title compound is obtained as yellow oil. TLC: methylene chloride/methanol/conc. ammonia (1000:50:1) R$_f$=0.65, FD-MS: M+ =574.

EXAMPLE 24

(2R*,4S*)-2-benzyl-1-(cis,cis-3,5-dimethylcyclohexylcarbonyl)-N-(4-quinolylmethyl)-4-piperidinamine 195 mg (0.345 mmol) of (2R*,4S*)-2-benzyl-1-(cis,cis-3,5-dimethylcyclohexylcarbonyl)-N-(4-quinolylmethyl)-N-trifluoroacetyl-4-piperidinamine are reacted with 52 mg (1.38 mmol) of sodium borohydride in analogy to Example 2. The title compound

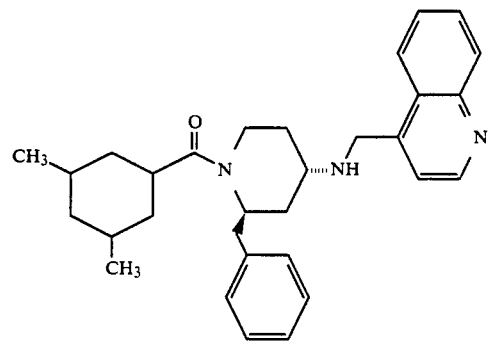

is obtained as white foam. TLC: methylene chloride/methanol/conc. ammonia (1000:50:1) R$_f$=0.24, FD-MS: M+ =469.

The starting compound for this is prepared as follows:

(2R*,4S*)-2-Benzyl-1-(cis,cis-3,5-dimethylcyclohexylcarbonyl)-N-(4-guinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 4 with 87 mg (0.561 mmol) of cis,cis-3,5-dimethylcyclohexylcarboxylic acid (prepared by the method of H. van Bekkum et. al. (Koninkl. Ned. Akad. Wetenschap, Proc. Ser. B. 64, 161 (1961)), 143 mg (0.561 mmol) of bis-(2-oxo-3-oxazolidinyl)phosphinic chloride and 144 μl (1.03 mmol) of triethylamine. The title compound is obtained as yellow oil. TLC: methylene chloride/methanol/conc. ammonia: (1000:50:1) R$_f$=0.32, FD-MS: M+ =565.

EXAMPLE 25

(2R*,4S*)-2-benzyl-1-(3,5-bis-(trifluoromethyl)benzyl)-N-(4-guinolylmethyl)-4-piperidinamine 280 mg (28 mmol) of (2R*,4S*)-2-benzyl-1-(3,5-bis-(trifluoromethyl)benzyl)-N-(4-quinolylmethyl)-N-trifluoroacetyl-4-piperidinamine are reacted with 65 mg (1.71 mmol) of sodium borohydride in analogy to Example 2. The title compound

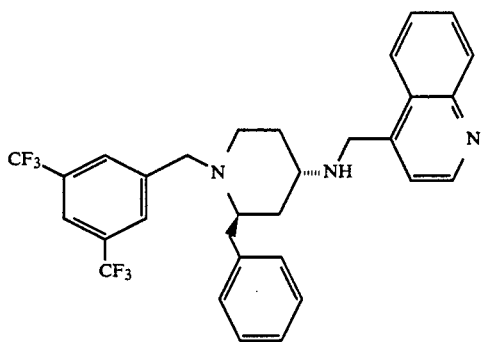

is obtained as white foam. TLC: methylene chloride/methanol/conc. ammonia (I 000:50:1) R$_f$=0.35, FD-MS: M+ =557.

The starting compound for this is prepared as follows:

(2R*,4S *)-2-Benzyl-1-(3,5-bis-(trifluoromethyl)benzyl)-$N-(4-quinolylmethyl)-N-trifluoroacetyl-4-piperidinamine A mixture of 129 μl (0.702 mmol) of 3,5-bis-(trifluoromethyl)benzyl bromide, 194 mg (1.40 mmol) of potassium carbonate and 300 mg (0.702 mmol) of (2R*,4S *)-2-benzyl-N-(4-quinolylmethyl)-N-trifluoroacetyl-4-piperidinamine in 3 ml of N,N-dimethylformamide is stirred at 60° for 17 hours. The suspension is then filtered, washed thoroughly with acetone, and the filtrate is concentrated in a rotary evaporator. The residue is taken up in methylene chloride and washed successively with 10% aqueous citric acid, 1N sodium hydrocarbonate solution, water and brine, and dried over magnesium sulfate. The yellow oil is chromatographed on silica gel with methylene chloride/methanol/conc. ammonia (3000:50:1). The title compound is obtained as yellow oil. TLC: methylene chloride/methanol/conc. ammonia (3000:50:1) R$_f$=0.36, FD-MS: M+ =653.

EXAMPLE 26

(2S*,4R*)-2-benzyl-1-[2-(5-chloro-1H-1,2,4-triazol-1-yl)phenoxyethyl]-N-(4-quinolylmethyl)-4-piperidinamine 100 mg (0.54 mmol) of (2R*,4S*)-2-benzyl-1-[2-(5-chlor-1H-1,2,4-triazol-1-yl)phenoxyethyl]-N-(4-quinolylmethyl)-N-trifluoroacetyl-4-piperidinamine are reacted with 23 mg (0.62 mmol) of sodium borohydride in analogy to Example 2. The title compound

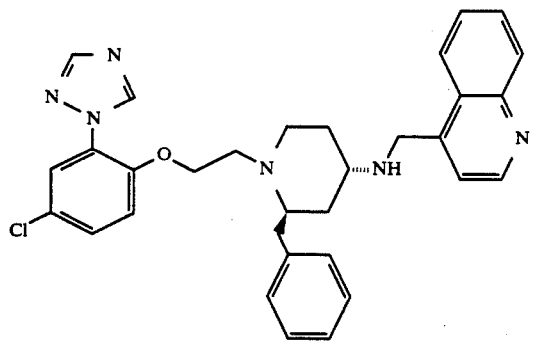

is obtained as white foam. TLC: methylene chloride/methanol/conc. ammonia (1000:50:1) $R_f=0.23$, FD-MS: $M^+=553$.

The starting compound for this is prepared as follows:

(2R*,4S*)-2-Benzyl-1-[2-(5-chlor-1H-1,2,4-triazol-1-yl)phenoxyethyl]-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 24 with 141 mg (0.468 mmol) of 2-(5-chloro-(1H-1,2,4-triazol-1-yl)phenoxy)ethyl bromide and 129 mg (0.936 mmol) of potassium carbonate. The title compound is obtained as white foam. TLC: methylene chloride/methanol/conc. ammonia (1000:50:1) $R_f=0.23$, FD-MS: $M^+=649$.

EXAMPLE 27

(2R*,4S*)-2-benzyl-1-((S)-phenylalanyl)-N-(4-quinolylmethyl)-4-piperidinamine 112 mg (0.195 mmol) of diastereomer A of (2R*,4S*)-2-benzyl-1-((S)-phenylalanyl)-N-(4-quinolylmethyl)-N-trifluoroacetyl-4-piperidinamine are reacted with 30 mg (0.801 mmol) of sodium borohydride in analogy to Example 2. The title compound

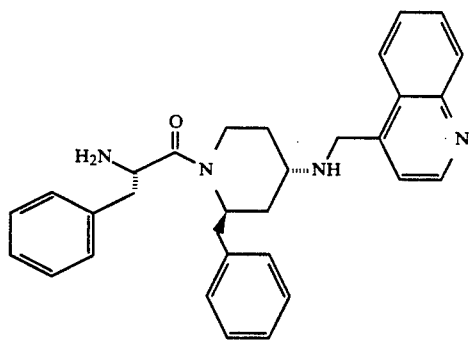

is obtained as white foam. TLC: methylene chloride/methanol/conc. ammonia (700:50:1) $R_f=0.21$, FD-MS: $M^+=478$.

The starting compounds for this are prepared as follows:

a) (2R*,4S*)-2-Benzyl-1-((S)-N-tert.-butyloxycarbonyl-phenylalanyl)-N-(4-quinolylmethyl)-N-trifluoroacetyl-4-piperidinamine 300 mg (0.702 mmol) of (2R*,4S*)-2-benzyl-N-(4-quinolylmethyl)-N-trifluoroacetyl-4-piperidinamine are reacted in analogy to Example 4 with 223 mg (0.842 mmol) of (S)-N-tert.-butyloxycarbonyl-phenylalanine, 214 mg (0.842 mmol) of bis-(2-oxo-3-oxazolidinyl)phosphinic chloride and 215 μl (1.54 mmol) of triethylamine. The title compound is obtained as mixture of diastereomers in the form of a yellow oil. TLC: methylene chloride/methanol/conc. ammonia (2000:50:1) $R_f=0.37$, FD-MS: $M^+=674$.

b) Diastereomers of (2R*,4S*)-2-benzyl-1-((S)-phenylalanyl)-N-(4-guinolylmethyl)-N-trifluoroacetyl-4-piperidinamine 3.1 ml (4.09 mmol) of trifluoroacetic acid are added to 920 mg (1.36 mmol) of (2R*,4S*)-2-benzyl-1-((S)-N-tert.-butyloxycarbonyl-phenylalanyl)-N-(4-quinolylmethyl)-N-trifluoroacetyl-4-piperidinamine, and the reaction mixture is stirred at room temperature for 2 hours. It is then concentrated in a rotary evaporator, the residue is taken up in water, basified with 1N sodium bicarbonate solution at 0° C. and extracted with methylene chloride. The organic phases are washed with brine, dried over magnesium sulfate and evaporated to dryness. The residue is chromatographed on silica gel with methylene chloride/methanol/conc. ammonia (2500:50:1) to separate the diastereomers. TLC: methylene chloride/methanol/conc. ammonia (1000:50:1)

Diastereomer A: $R_f=0.24$, FD-MS: $M^+=574$,
Diastereomer B: $R_f=0.22$, FD-MS: $M^+=574$.

The mixed fractions of diastereomer A and B were not fractionated further.

EXAMPLE 28

Diastereomer B of (2R*,4S*)-2-benzyl-1-((S)-phenylalanyl)-N-(4-quinolylmethyl)-4-piperidinamine 115 mg (0.200 mmol) of diastereomer B of (2R*,4S*)-2-benzyl-1-((S)-phenylalanyl)-N-(4-quinolylmethyl)-N-trifluoroacetyl-4-piperidinamine are reacted with 30 mg (0.801 mmol) of sodium borohydride in analogy to Example 2. The title compound

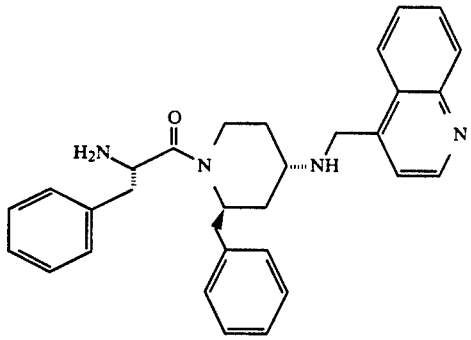

is obtained as white foam. TLC: methylene chloride/methanol/conc. ammonia (700:50:1) $R_f=0.20$, FD-MS: $M^+=478$.

See Example 27a for the starting compound for this.

EXAMPLE 29

Diastereom A of (2R*,4S*)-2-benzyl-1-((R)-phenylalanyl)-N-(4-quinolylmethyl)-4-piperidinamine 174 mg (0.303 mmol) of diastereomer A of (2R*,4S*)-2-benzyl-1-((R)-phenylalanyl)-N-(4-quinolylmethyl)-N-trifluoroacetyl-4-piperidinamine are reacted with 46 mg (1.211 mmol) of sodium borohydride in analogy to Example 2. The title compound

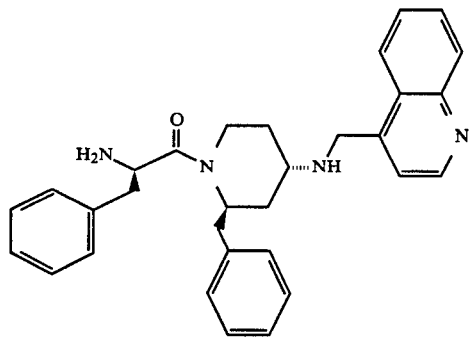

is obtained as white foam. TLC: methylene chloride/methanol/conc. ammonia (700:50:1) $R_f=0.28$, FD-MS: $M^+=478$.

The starting compounds for this are prepared as follows:

Diastereomers of (2R*,4S*)-2-benzyl-1-((R)-phenylalanyl)-N-(4-quinolylmethyl)-N-trifluoroacetyl-4-piperidinamine 1.10 g (1.63 mmol) of (2R*,4S*)-2-benzyl-1-((R)-N-tert.-butyloxycarbonyl-phenylalanyl)-N-(4-quinolylmethyl)-N-trifluoroacetyl- 4-piperidinamine are treated with 3.8 ml (48.8 mmol) of trifluoroacetic acid in analogy to Example 27b. The diastereomers of the title compound are obtained. TLC: methylene chloride/methanol/conc. ammonia (1000:50:1)

Diastereomer A: $R_f=0.52$, FD-MS: $M^+=574$,
Diastereomer B: $R_f=0.50$, FD-MS: $M^+=574$.

The mixed fractions of diastereomer A and B are not fractionated further.

EXAMPLE 30

Diastereomer B of (2R*,4S*)-2-benzyl-1-((R)-phenylalanyl)-N-(4-guinolylmethyl)-4-piperidinamine 92 mg (0. 160 mmol) of diastereomer B of (2R*,4S*)-2-benzyl- 1 -((R)-phenylalanyl)-N-(4-quinolylmethyl)-N-trifluoroacetyl-4-piperidinamine are reacted with 25 mg (0.640 mmol) of sodium borohydride in analogy to Example 2. The title compound

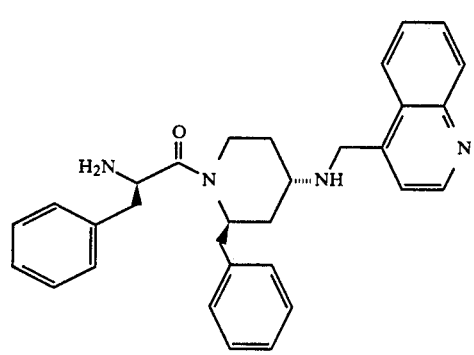

is obtained as white foam. TLC: methylene chloride/methanol/conc. ammonia (350:50:1) $R_f=0.49$, FD-MS: $M^+=478$.

See Example 27a for the starting compound for this.

EXAMPLE 31

(2R*,4S*)-2-benzyl-1-((S)-N-acetyl-phenylalanyl)-N-(4-quinolylmethyl)-4-piperidinamine 160 mg (0.259 mmol) of the mixture of (2R*,4S*)-2-benzyl-1-((S)-N-acetyl-phenylalanyl)N-(4-quinolylmethyl)-N-trifluoroacetyl-4-piperidinamine diastereomers are reacted with 39 mg (1.04 mmol) of sodium borohydride in analogy to Example 2. The title compound

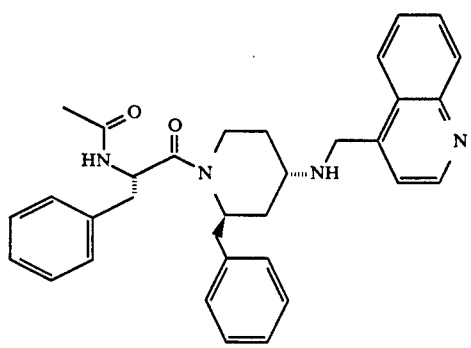

is obtained as mixture of diastereomers as white foam. TLC: methylene chloride/methanol/conc. ammonia (1000:50:1) $R_f=0.22$, FD-MS: $M^+=520$.

The starting compound for this are prepared as follows:

(2R*,4S*)-2-Benzyl-1-((S)-N-acetyl-phenylalanyl)N-(4-guinolylmethyl)-N-trifluoroacetyl-4-piperidinamine 35 μl (0.376 mmol) of acetic anhydride are added to a solution of 180 mg (0.313 mmol) of the mixture of (2R*,4S*)-2-benzyl-1-((S)-phenylalanyl)-N-(4-quinolylmethyl)-N-trifluoroacetyl-4-piperidinamine diastereomers in 2 ml pyridine at 0°, and the mixture is stirred at 0° for 2.5 hours. The oily residue after evaporation in a rotary evaporator is taken up in methylene chloride, washed with 5% aqueous citric acid and with 1N sodium bicarbonate solution. The organic phases are dried over magnesium sulfate and evaporated to dryness. The title compound is obtained as white foam. TLC: methylene chloride/methanol/conc. ammonia (1000:50:1) $R_f=0.39$, FD-MS: $M^+=616$.

EXAMPLE 32

(2R*,4S*)-2-benzyl-1-((R)-N-acetyl-phenylalanyl)-N-(4-quinolylmethyl)-4-piperidinamine 185 mg (0.411 mmol) of the mixture of (2R*,4S *)-2-benzyl-1-((R)-N-acetyl-phenylalanyl)N-(4-quinolylmethyl)-N-trifluoroacetyl-4-piperidinamine diastereomers are reacted with 62 mg (1.64 mmol) of sodium borohydride in analogy to Example 2. The title compound

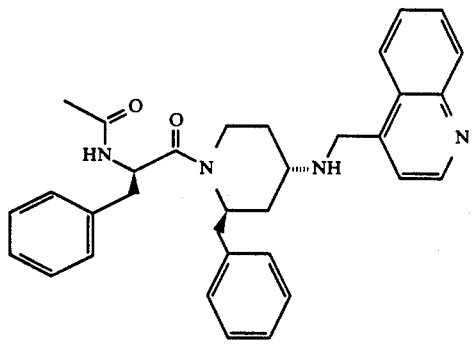

is obtained as mixture of diastereomers (white foam). TLC: methylene chloride/methanol/conc. ammonia (700:50:1) R$_f$=0.42, FD-MS: M+ =520.

The starting compound for this is prepared as follows:

(2R*,4S*)-2-Benzyl-1-((R)-N-acetyl-phenylalanyl)N-(4-guinolylmethyl)-N-trifluoroacetyl-4-piperidinamine 920

200 mg 0.348 mmol) of the mixture of (2R*,4S*)-2-benzyl-1-((R)-phenylalanyl)-N-(4-quinolylmethyl)-N-trifluoroacetyl-4-piperidinamine diastereomers are reacted with 39 μl (0.417 mmol) of acetic anhydride in analogy to Example 31. The title compound is obtained as mixture of diastereomers (white foam). TLC: methylene chloride/methanol/conc. ammonia (1000:50:1) R$_f$=0.28, FD-MS: M+ =616.

EXAMPLE 33

(2R*,4S*)-2-benzyl-1-((S)-N-(4-carboxamido-butyroyl)phenylalanyl)-N-(4-guinolylmethyl)-4-piperidinamine 152 mg (0.221 mmol) of the mixture of (2R*,4S*)-2-benzyl-1-((S)-N-(4-carboxamidobutyroyl)-phenylalanyl)N-(4-quinolylmethyl)-N-trifluoroacetyl-4-piperidinamine are reacted with 34 mg (0.88 mmol) of sodium borohydride in analogy to Example 2. The title compound

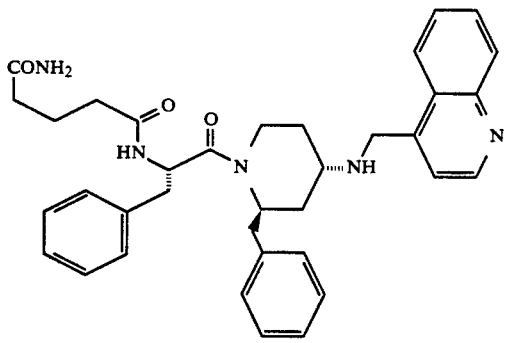

is obtained as mixture of diastereomers as white foam. TLC: methylene chloride/methanol/conc. ammonia (350:50:1) R$_f$=0.50, FD-MS: M+ =591.

The starting compound for this is prepared as follows:

(2R*,4S*)-2-Benzyl-1-((S)-N-(4-carboxamido-butyroyl)phenylalanyl)-N-(4-quinolylmethyl)-N-trifluoroacetyl-4-piperidinamine 179 μl (1.04 mmol) of diisopropylethylamine and 108 mg (0.348 mmol) of glutamic acid mono-2,4,5-trichlorophenyl ester amide are added to a solution of 200 mg (0.348 mmol) of the mixture of (2R*,4S*)-2-benzyl-1-((S)-phenylalanyl)-N-(4-quinolylmethyl)-N-trifluoroacetyl-4-piperidinamine diastereomers in 2 ml of methylene chloride at 0°, and the white suspension is stirred at 0° for 2 hours and at room temperature for 16 hours. The solution, which is now colourless, is concentrated in a rotary evaporator, and the oily residue is then taken up in methylene chloride, washed with 5% aqueous citric acid and with 1N sodium bicarbonate solution. The organic phases are dried over magnesium sulfate and evaporated to dryness. The title compound is obtained as white foam. TLC: methylene chloride/methanol/conc. ammonia (1 000:50:1) Rf=0.13, FD-MS: M+ =687.

EXAMPLE 34

(2R*,4S*)-2-benzyl-1-((R)-N-(4-carboxamido-butyroyl)phenylalanyl)-N-(4-guinolylmethyl)-4-piperidinamine 210 mg (0.305 mmol) of the mixture of (2R*,4S*)-2-benzyl-1-((R)-N-(4-carboxamidobutyroyl)-phenylalanyl)N-(4-quinolylmethyl)-N-trifluoroacetyl-4-piperidinamine are reacted with 46 mg (1.22 mmol) of sodium borohydride in analogy to Example 2. The title compound

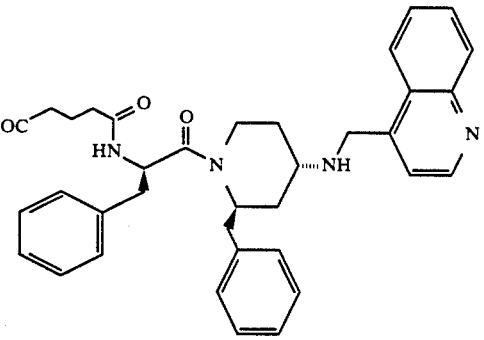

is obtained as mixture of diastereomers as white foam. TLC: methylene chloride/methanol/conc. ammonia (350:50:1) R$_f$=0.56, FD-MS: M+ =591.

The starting compound for this is prepared as follows:

(2R*,4S*)-2-Benzyl-1-[(R)-N-(4-carboxamido-butyroyl)phenylalanyl]-N-(4-guinolylmethyl)-N-trifluoroacetyl-4-piperidinamine 222 mg (0.386 mmol) of the mixture of (2R*,4S*)-2-benzyl-1-[(R)-phenylalanyl)-N-(4-quinolylmethyl]-N-trifluoroacetyl-4-piperidinamine diastereomers are reacted in analogy to Example 33 with 198 μl (1. 16 mmol) of diisopropylethylamine and 120 mg (0.386 mmol) of glutamic acid mono-2,4,5-trichlorophenyl ester amide. The title compound is obtained as mixture of diastereomers as white foam. TLC: methylene chloride/methanol/conc. ammonia (700:50:1) R$_f$=0.38, FD-MS: M+ =687.

EXAMPLE 35

(2R*,4S*)-2-benzyl-1-benzoyl-N-(4-quinolylmethyl)-4-piperidinamine 234 mg (0.440 mmol) of (2R*,4S*)-2-benzyl-1-benzoyl-N-(4-quinolylmethyl)-N-trifluoroacetyl-4-piperidinamine are reacted with 67 mg (1.76 mmol) of sodium borohydride in analogy to Example 2. The title compound

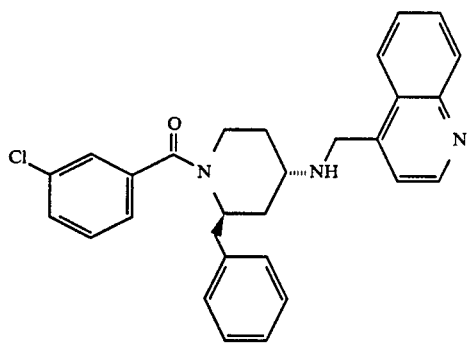

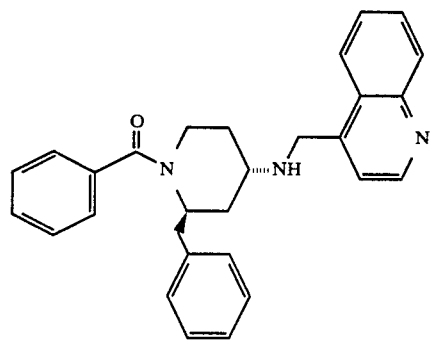

is obtained as white foam. TLC: methylene chloride/methanol/conc. ammonia (700:50:1) R$_f$=0.33, FD-MS: M+ =435.

The starting compound for this is prepared as follows:

(2R*,4S*)-2-Benzyl-1-benzoyl-N-(4-quinolylmethyl)-N-trifluoroacetyl-4-piperidinamine 72 μl (0.515 mmol) of triethylamine and 54 μl (0.468 mmol) of benzoyl chloride are added to a solution of 200 mg (0.468 mmol) of (2R*,4S*)-2-benzyl-N-(4-quinolylmethyl)-N-trifluoroacetyl-4-piperidinamine in 4 ml of methylene chloride. The reaction mixture is stirred at 0° for 3 hours, water is added, extraction with methylene chloride is carried out. The organic phases are dried over magnesium sulfate and evaporated to dryness. The yellow oil is chromatographed on silica gel with methylene chloride/methanol/conc. ammonia (1000:50:1). The title compound is obtained as white foam. TLC: methylene chloride/methanol/conc. ammonia (700:50:1) R$_f$=0.72, FD-MS: M+ =531.

EXAMPLE 36

(2R*,4S*)-2-benzyl-1-(3-chlorobenzoyl)-N-(4-guinolylmethyl-4-piperidinamine 254 mg (0.449 mmol) of (2R*,4S*)-2-benzyl-1-(3-chlorobenzoyl)-N-(4-quinolylmethyl)-N-trifluoroacetyl-4-piperidinamine are reacted with 68 mg (1.80 mmol) of sodium borohydride in analogy to Example 2. The title compound is obtained as white foam. TLC: methylene chloride/methanol/conc. ammonia (700:50:1) R$_f$=0.29, FD-MS: M+ =470.

The starting compound for this is prepared as follows:

(2R*,4S*)-2-Benzyl-1-(4-chlorobenzoyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinaniine are reacted in analogy to Example 35 with 72 μl (0.515 mmol) of triethylamine and 60 μl (0.468 mmol) of 3-chlorobenzoyl chloride to give the product. TLC: methylene chloride/methanol/conc. ammonia (700:50:1) R$_f$=0.71, FD-MS: M+ =566.

EXAMPLE 37

(2R*,4S*)-2-benzyl-1-(3,5-dichlorobenzoyl)-N-(4-guinolylmethyl)-N-(3-carboxamidopropionyl)-4-piperidinamine 92 mg (0.99 mmol) of 1-hydroxybenzotriazole and 138 mg (0.899 mmol) of N,N'-dicyclohexylcarbodiimide are added to a solution of 181 mg (0.299 mmol) of (2R*,4S*)-2-benzyl-1-(3,5-dichlorobenzoyl)-N-(4-quinolylmethyl)-N-(3-carboxypropionyl)-4-piperidinamine in 2 ml of tetrahydrofuran. Stirring at room temperature for half an hour is followed by addition of 2.1 n-d (15 mmol) of a 7 M solution of ammonia in ethanol and stirring at room temperature for 36 hours. The residue from evaporation in a rotary evaporator is suspended in methylene chloride/ether (1:1), and the white suspension is filtered. The filtrate is concentrated in a rotary evaporator, and the yellow oil is chromatographed on silica gel with methylene chloride/methanol/conc. ammonia (1000:50:1). The title compound

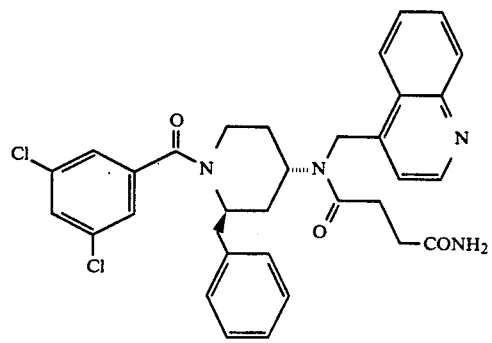

is obtained as white solid substance. TLC: methylene chloride/methanol/conc. ammonia (700:50:1) $R_f=0.23$, FD-MS: M+ =602, 604. (2R*,4S*)-2-Benzyl-1-(3,5-dichlorobenzoyl)-N-(4-quinolylmethyl)-N-(3-N-cyclohexylcarbamidopropionyl)-4-piperidinamine is obtained as by product from the chromatography. TLC: methylene chloride/methanol/conc. ammonia (700:50:1) $R_f=0.40$, FD-MS: M+ =684,686.

EXAMPLE 38

(2R,4S)-2-benzyl-1(3,5-bis-(trifluoromethyl)benzoyl)-N-(4-quinolylmethyl)-4-piperidinamine 3.35 g (7.78 mmol) of (2R,4S)-2-benzyl-1-(3,5-bis-(trifluoromethyl)benzoyl)-4-piperidinamine are reacted in analogy to Example 2 g with 1.34 g (8.56 mmol) of quinoline-4-carboxaldehyde and 1.3 g of magnesium sulfate in 30 ml of toluene, and subsequently reduced with 324 mg (8.56 mmol) of sodium borohydride in 25 ml of methanol. The title compound

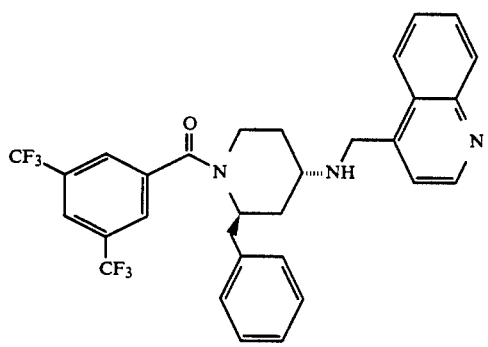

is obtained (3.5 g, 79%) as white foam. TLC: methylene chloride/methanol/conc. ammonia (1000:50:1) $R_f=0.21$, FD-MS: M+ =571, $[\alpha]_D=+0.7$ (c=1, MeOH), IR: 1635 cm$^{-1}$.

The starting compound for this is prepared as follows:

a) (2R,4R)-2-Benzyl-1-t-butyloxycarbonyl-4-hydroxypiperidine 24 g (111 mmol) of (−)-camphanic chloride are added to a solution of 26.9 g (92.3 mmol) of (2R*,4R*)-2-benzyl-1-t-butyloxycarbonyl-4-hydroxypiperidine in 200 ml of pyridine at 0° C., and the mixture, which becomes heterogeneous, is stirred at 0° C. for 2 hours and subsequently at RT for 16 hours. After concentration in a rotary evaporator, the reaction mixture is taken up in methylene chloride, washed twice with 10% citric acid, once with water and once with brine, dried over magnesium sulfate and evaporated in a rotary evaporator. 47.8 g of the diastereomeric mixture of the camphanic esters are obtained as orange oil. Diastereomer A: $R_f=0.52$; Diastereomer B: $R_f=0.47$. The latter is chromatographed on silica gel with toluene/ethyl acetate (9:1), and the diastereomeric esters are crystallised from hexane. Diastereomer A is obtained as white crystals (14.2 g, 33%); melting point: 114°-115° C. and diastereomer B as white crystals (15.3 g, 35%); melting point: 138°-139° C.

130 ml of 0.5N sodium hydroxide solution are added to a solution of diastereomer B in 300 ml of methanol, and the reaction mixture is stirred at RT for 18 hours. After concentration in a rotary evaporator, the reaction mixture is taken up in methylene chloride, washed with water and brine, dried over magnesium sulfate and evaporated in a rotary evaporator. The title compound is obtained as yellow oil (9.3 g, 98%). TLC: toluene-/ethyl acetate (7:3) $R_f=0.34$, FD-MS: M+291, $[\alpha]_D=+32°$ (c=1, Methanol).

b) (2R,4R)-2-Benzyl-1-t-butyloxycarbonyl-4-(O-methylsulfonyl)-hydroxypiperidine 9.3 g (32 mmol) of (2R,4R)-2-benzyl-1-t-butyloxycarbonyl-4-hydroxypiperidine are reacted with 5 ml (63.8 mmol) of methanesulfonyl chloride in 10 ml of pyridine in analogy to Example 2d. The title compound (11 g, 93%) is obtained as colourless needles. Melting point: 137° C, TLC: toluene/ethyl acetate (4:1) $R_f=0.42$, $[\alpha]_D=+21°$ (c=1, MeOH).

c) (2R,4S)-2-Benzyl-1-t-butyloxycarbonyl-4-piperidine azide 10.9 g (29.6 mmol) of (2R,4R)-2-benzyl-1-t-butyloxycarbonyl-4-(O-methylsulfonyl)hydroxypiperidine are reacted with 1.6 g (32.6 mmol) of lithium azide in 60 ml of N,N-Dimethylformamide in analogy to Example 2e. The title compound is obtained mixed with 2-benzyl-N-t-butyloxycarbonyl-1,2,5,6-tetrahydropylidine (9.2 g, ratio by weight according to NMR: 4.7:1), which is not fractionated further. TLC: toluene/ethyl acetate (9:1) $R_f=0.59$.

d) (2R,4S)-2-Benzyl-4-piperidine azide

A mixture from Example 38c (calculated content of (2R,4S)-2-benzyl-1-t-butyloxycarbonyl-4-piperidine azide: 7.58 g (80%)) is mixed with 36 ml of trifluoroacetic acid and stirred at RT for 90 minutes. It is then concentrated in a rotary evaporator, the residue is taken up in methylene chloride and washed with 2N sodium hydroxide solution. The organic phases are dried over magnesium sulfate and evaporated to dryness. The residue is chromatographed on silica gel with methylene chloride/methanol/conc. ammonia (1000:50:1). The title compound (4.7 g, 92%) is obtained as yellow oil. TLC: methylene chloride/methanol/conc. ammonia (350:50:1) $R_f=0.63$, IR: 2100 cm$^{-1}$, $[\alpha]_D=-28.8°$ (c=1, Methanol).

e) (2R,4S)-2-Benzyl-1-(3,5-bis-(trifluoromethyl)benzoyl)-4-piperidine azide 2.2 g (10.2 mmol) of (2R,4S)-2-benzyl-4-piperidine azide are reacted in analogy to Example 4a with 2.5 g (12.2 mmol) of 3,5-bis-(trifluoromethyl)benzoic acid, 3.1 g (12.2 mmol) of bis(2-oxo-3-oxazolidinyl)phosphinic chloride and 3.1 ml (22.4 mmol) of triethylamine. The title compound (4.16 g, 90%) is obtained as yellow oil. TLC: toluene/ethyl acetate (9:1) $R_f=0.45$, FD-MS: M+ =456, $[\alpha]_D=+5.1°$ (c=1, Methanol).

f) (2R,4S)-2-Benzyl-1-(3,5bis-(trifluoromethyl)benzoyl)-4-piperidinamine 4.1 g (9.0 mmol) of (2R,4S)-2-benzyl-1-(3,5-bis-(trifluoromethyl)benzoyl)-4-piperidine azide are hydrogenated with 10% Pd/C in analogy to Example 2f. The title compound (3.38 g, 87%) is obtained as oil. TLC: methylene chloride/methanol/conc. ammonia (350:50:1) $R_f=0.47$, FD-MS: M+ =430, $[\alpha]_D=-3.0°$ (c=1, Methanol).

EXAMPLE 39

(2R,4S)-2-benzyl-1-(3,5-dichlorobenzoyl)-N-(4-guinolylmethyl)-4-piperidinamine 1.95 g (5.37 mmol) of (2R,4S)-2-benzyl-1-(3,5-dichlorobenzoyl)-4-piperidinamine are reacted in analogy to Example 2g with 0.93 g (5.90 mmol) of quinoline-4-carboxaldehyde and 0.9 g of magnesium sulfate in 18 ml of toluene and subsequently reduced with 223 mg (5.90 mmol) of sodium borohydride in 18 ml of methanol. The title compound

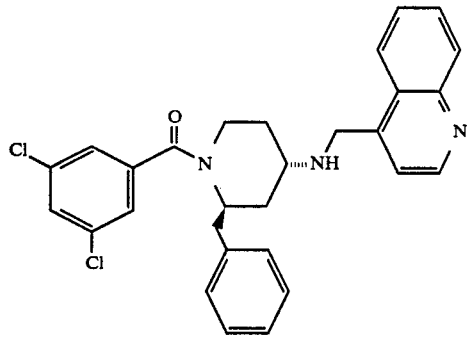

is obtained (2.2 g, 82%) as white foam. TLC: methylene chloride/methanol/conc. ammonia (700:50:1) $R_f$=0.35, FD-MS: M+ =503, 505, $[\alpha]_D$= −19.3 (c=1, MEOH), IR: 1635, 1595, 1565 cm$^{-1}$.

The starting compound for this is prepared as follows:

a) (2R,4S)-2-Benzyl-1-(3,5-dichlorobenzoyl)-4-piperidine azide

A solution of 2.8 g (13.3 mmol) of 3,5-dichlorobenzoyl chloride is added dropwise to a solution of 2.4 g (11.1 mmol) of (2R,4S)-2-benzyl-4-piperidine azide and 2.2 ml (15.5 mmol) of triethylamine in 35 ml of methylene chloride at 0° C. Sniffing at 0° C. for 18 hours is followed by concentration in a rotary evaporator, and the yellow oil is partitioned between methylene chloride and water. The organic phases are washed with brine, dried over magnesium sulfate and evaporated to dryness. The resulting oil is chromatographed on silica gel with toluene/ethyl acetate (9:1). The title compound (4.04 g, 94%) is obtained as semicrystalline mass. TLC: toluene/ethyl acetate (9:1) $R_f$=0.51; FD-MS: M+ =388, 390; $[\alpha]_d$= +33.40 (c=1, MeOH).

b) (2R,4S)-2-Benzyl-1-(3,5-dichlorobenzoyl)-4-piperidinamine 4.02 g (10.3 mmol) of (2R,4S)-2-benzyl-1-(3,5-dichlorobenzoyl)-4-piperidine azide are hydrogenated with 10% Pd/C in analogy to Example 2f. The title compound (1.97 g, 52%) is obtained as oil. TLC: methylene chloride/methanol/conc. ammonia (350:50:1) $R_f$=0.40, FD-MS: M+ =362, 364; IR: 3660, 3360, 1630 cm$^{-1}$; $[\alpha]_D$= +22.70 (c=1, Methanol).

EXAMPLE 40

(2R*,4S*)-2-benzyl-1-(2,4-dichlorobenzoyl)-N-(4-guinolylmethyl)-4-piperidinamine A solution of 195 mg (0.325 mmol) of (2R*,4S*)-2-benzyl-1-(2,4-dichlorobenzoyl)-N-(4-quinolylmethyl)-N-trifluoroacetyl-4-piperidinamine and 26 mg (0.649 mmol) of sodium hydroxide in 2 ml of methanol and 2 ml of tetrahydrofuran is left to stir at 0° C. for 18 hours. The reaction mixture is then concentrated, taken up in methylene chloride and washed with water and brine. The organic phases are dried over magnesium sulfate and evaporated to dryness. The yellow oil is chromatographed on silica gel with methylene chloride/methanol/conc. ammonia (800:50:1). The title compound

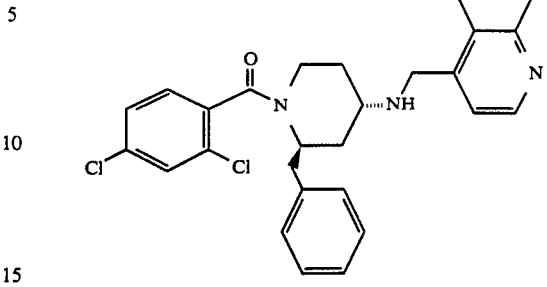

is obtained (157 mg, 96%) as white foam. TLC:methylene chloride/methanol/conc. ammonia (700:50:1) $R_f$=0.45, FD-MS: M+ =503.505.

The starting compound for this is prepared as follows:

(2R*,4S*)-2-Benzyl-1(2,4-dichlorobenzoyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 35a with 91 μl (0.655 mmol) of triethylamine and 78 μl (0.561 mmol) of 2,4-dichlorobenzoyl chloride to give the title compound (240 mg, 86%). TLC: methylene chloride/methanol/conc. ammonia (700:50:1) $R_f$=0.57, FD-MS: M+ =599,601.

EXAMPLE 41

(2R*,4S*)-2-benzyl-1-(phenylacetyl)-N-(4-quinolylmethyl)-4-piperidinamine 192 mg (0.352 mmol) of (2R*,4S*)-2-benzyl-1-(2-phenylacetyl)-N-(4-quinolylmethyl)-N-trifluoroacetyl-4-piperidinamine are reacted in analogy to Example 40 with 141 μl (0.704 mmol) of 5N sodium hydroxide solution in 1 ml of tetrahydrofuran and 1 ml of methanol. The title compound

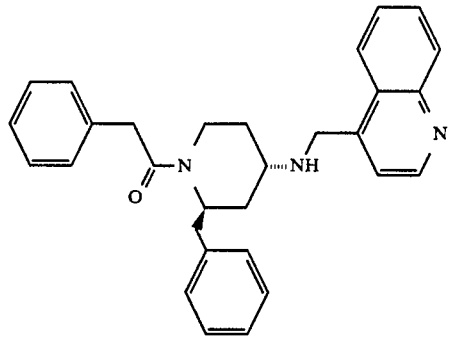

is obtained (73 mg, 46%) as white foam. TLC: methylene chloride/methanol/conc. ammonia (700:50:1) $R_f$=0.43, FD-MS: M+ =449.

The starting compound for this is prepared as follows:

(2R*,4S*)-2-Benzyl-1-(phenylacetyl)-N-(4-quinolylmethyl)-N-trifluoracetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 35a with 72 μl (0.515 mmol) of triethylamine and 62 μl (0.468 mmol) of phenylacetyl chloride to give the title compound (208 mg, 81%)] TLC: methylene chloride/methanol/conc. ammonia (700:50:1) $R_f=0.54$, FD-MS: M+ =545.

EXAMPLE 42

(2R*,4S*)-2-benzyl-1-(2,6-dichlorobenzoyl)-N-(4-quinolymethyl)-4-piperidinamine 138 mg (0.230 mmol) of 2R*,4S*)-2-benzyl-1-(2,6-dichlorobenzyl)-N-(4-quinolylmethyl)-N-trifluoroacetyl)-4-piperpidinamine are reacted in analogy to Example 40 and 18.4 mg (0.460 mmol) of sodium hydroxide in 1.5 ml of tetrahydrofuran and 1.5 ml of methanol. The title compound

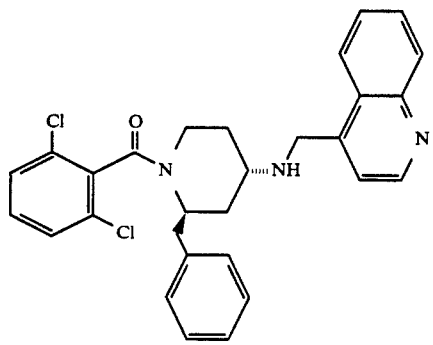

is obtained (56 mg, 48%) as white foam. TLC: methylene chloride/methanol/conc. ammonia (700:50:1) $R_f=0.50$, FD-MS: M+ =503, 505.

The starting compound for this is prepared as follows:

(2R*,4S*)-2-Benzyl-1-(2,6-dichlorobenzoyl)-N-(4-quinolylmethyl)-N-trifluoroacetyl-4-piperidinamine 200 mg (0.468 mmol) of (2R*,4S*)-2-benzyl-N-(4-quinolylmethyl)-N-trifluoroacetyl-4-piperidinamine are reacted in analogy to Example 35a with 91 μl (0.655 mmol) of triethylamine and 80 μl (0.561 mmol) of 2,6-dichlorobenzoyl chloride to give the title compound (158 mg, 56%). TLC: methylene chloride/methanol/conc. ammonia (700:50:1) $R_f=0.62$, FD-MS: M+ =599, 601.

EXAMPLE 43

(2R*,4S*)-2-Benzyl-1-(3,5-dibromobenzoyl)-N-(4-quinolylmethyl)-4-piperidinamine.

0.166 g (0.241 mmol) of (2R*,4S*)-2-benzyl-1-(3,5-dibromobenzoyl)-N-(4-quinolylmethyl)-N-trifluoroacetyl-4-piperidinamine is reacted with 0.037 g (0.96 mmol) of sodium borohydride in analogy to Example 2. The title compound

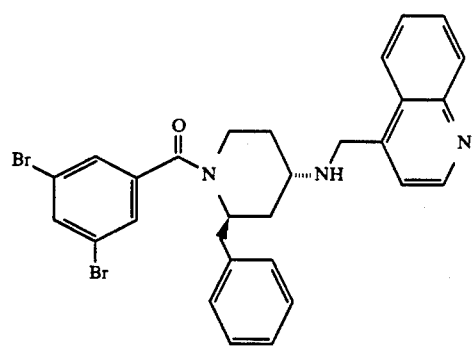

is obtained (0.094 g, 66%) as white foam. TLC: methylene chloride/methanol/conc. ammonia (700:50:1) $R_f=0.23$, FD-MS: M+ =591, 593, 595.

The starting compound for this is prepared as follows:

(2R*,4S*)-2-Benzyl-1-(3,5-dibromobenzoyl)-N-(4-quinolylmethyl)-N-trifluoroacetyl-4-piperidinamine 197 mg (0.70 mmol) of 3,5-dibromobenzoic acid (prepared according to J. Organometallic Chem. 215, 281 (198 1)) are reacted in analogy to Example 2a first with 2 ml (27 mmol) of thionyl chloride and subsequently with 200 mg (0.468 mmol) of (2R*,4S*)-2-benzyl-N-(4-quinolylmethyl)-N-trifluoroacetyl-4-piperidinamine and 130 μl (0.936 mmol) of triethylamine to give the title compound (168 mg, 52%). TLC: methylene chloride/methanol/conc. ammonia (700:50:1) $R_f=0.60$, FD-MS: M+ =687, 689, 691.

EXAMPLE 44

(2R*,4S*)-2-benzyl-1-(9-fluorenovl)-N-(4-quinolyl-methyl-4-piperidinamine.

0.238 g (0.384 mmol) of (2R*,4S*)-2-benzyl-1-(9-fluorenoyl)-N-(4-quinolylmethyl)-N-trifluoroacetyl-4-piperidinamine is reacted with 0.066 g (1.54 mmol) of sodium borohydride in analogy to Example 2. The title compound

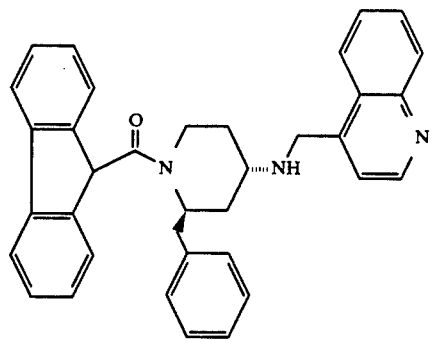

is obtained (0.155 g,79%) as white foam. TLC: methylene chloride/methanol/conc. ammonia (700:50:1) $R_f=0.36$, FD-MS: M+ =523.

The starting compound for this is prepared as follows: (2R*,4S*)-2-Benzyl-1-(9-fluorenoyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted in analogy to Example 4a with 78 mg (0.562 mmol) of 9-fluorene carboxylic acid, 143 mg (0.561 mmol) of bis-(2-oxo-3-oxazolidinyl)phosphinic chloride and 144 μ(1.03 mmol) of triethylamine. The title compound (241 mg, 82%) is obtained as oil. TLC: methylene chloride/methanol/conc. ammonia (1000:50:1) R/=0.58, FD-MS: M+ =619.

EXAMPLE 45

(2R*,4S*)-2-benzyl-1-(3-toluoyl)-N-(4-quinolylmethyl)-4-piperidinamine 0.251 g (0.460 mmol) of (2R*,4S*)-2-benzyl-1-(3-toluoyl)-N-(4-quinolylmethyl)-N-trifluoroacetyl-4-piperidinamine is reacted with 0.070 g (1.84 mmol) of sodium borohydride in analogy to Example 2. The title compound

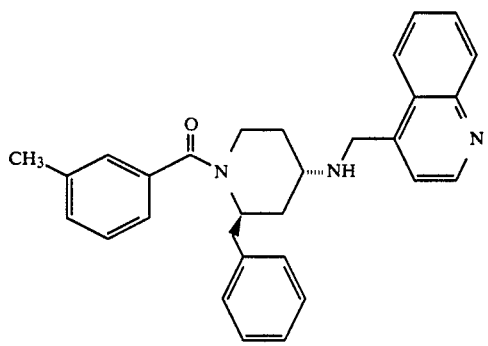

is obtained (0.172 g, 83%) as white foam. TLC: methylene chloride/methanol/conc. ammonia (700:50:1) R/=0.27, FD-MS: M+ =449.

The starting compound for this is prepared as follows:

(2R*,4S*)-2-Benzyl-1-(3-toluoyl)-N-(4-quinolylmethyl)-N-trifluoroacetyl-4-piperidinamine 96 mg (0.70 mmol) m-toluic acid are reacted in analogy to Example 2 a first with 2 ml (27 mmol) of thionyl chloride and subsequently with 200 mg (0.468 mmol) of (2R*,4S*)-2-benzyl-N-(4-quinolylmethyl)-N-trifluoroacetyl-4-piperidinamine and 118 μl (0.842 mmol) of triethylamine to give the title compound (251 mg, 98%). TLC: methylene chloride/methanol/conc. ammonia (700:50:1) R/=0.51, FD-MS: M+ =545.

EXAMPLE 46

(2R*,4S*)-2-benzyl-1-(3-bromobenzoyl)-N-(4-quinolylmethyl)-4-piperidinamine 0.271 g (0.444 mmol) of (2R*,4S*)-2-benzyl-1-(3-bromobenzoyl)-N-(4-quinolylmethyl)-N-trifluoroacetyl-4-piperidinamine is reacted with 0.067 g (1.78 mol) of sodium borohydride in analogy to Example 2. The title compound

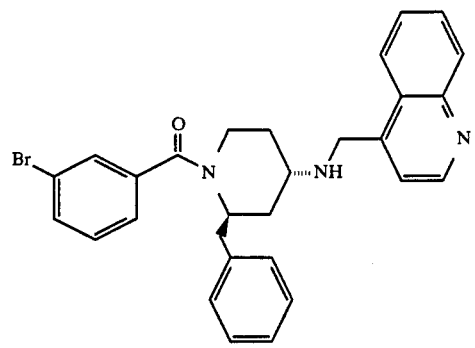

is obtained (0.212 g, 93%) as oil. TLC: methylene chloride/methanol/conc. ammonia (700:50:1) R/=0.29, FD-MS: M+ =513, 515.

The starting compound for this is prepared as follows:

(2R*,4S*)-2-Benzyl-1-(3-bromobenzoyl)-N-(4-quinolylmethyl)-N-trifluoroacetyl-4-piperidinamine 141 mg (0.70 mmol) of m-bromobenzoic acid are reacted in analogy to Example 2a first with 2 ml (27 mmol) of thionyl chloride and subsequently with 200 mg (0.468 mmol) of (2R*,4S*)-2-benzyl-N-(4-quinolylmethyl)-N-trifluoroacetyl-4-piperidinamine and 118 μl (0.842 mmol) of triethylamine to give the title compound (271 mg, 95%). TLC: methylene chloride/methanol/conc. ammonia (700:50:1) R/=0.71, FD-MS: M+ =609, 611.

EXAMPLE 47

(2R*,4S*)-2-benzyl-1-(3,5-dihydroxybenzoyl)-N-(4-quinolylmethyl)-4-piperidinamine 0.097 g (0.172 mmol) of (2R*,4S*)-2-benzyl-1-(3,5-dihydroxybenzoyl)-N-(4-quinolylmethyl)-N-trifluoroacetyl-4-piperidinamine is reacted with 0.026 g (0.688 mmol) of sodium borohydride in analogy to Example 2. The title compound

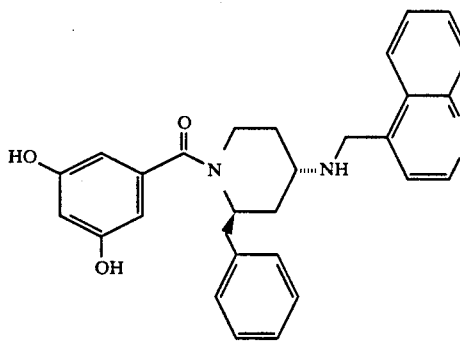

is obtained (0.023 g, 29%) as white foam. TLC: methylene chloride/methanol/conc. ammonia (350:50:1) R/=0.57, FD-MS: M+ =467.

The starting compound for this is prepared as follows:

(2R*,4S*)-2-Benzyl-1-(3,5-dihydroxybenzoyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted in analogy to Example 4a with 87 mg (0.562 mmol) of 3,5-dihydroxybenzoic acid, 143 mg (0.561 mmol) of bis-(2-oxo-3-oxazolidinyl)phosphinic chloride and 144 μl (1.03 mmol) of triethylamine. The title compound (99 mg, 38%) is obtained as white foam. TLC: methylene chloride/methanol/conc. ammonia (700:50:1) R/=0.41, FD-MS: M+=563.

EXAMPLE 48

(2R*,4S*)-2-benzyl-1-(3-cyanobenzoyl)-N-(4-quinolylmethyl)-4-piperidinamine 0.248 g (0.446 mmol) of (2R*,4S*)-2-benzyl-1-(3-cyanobenzoyl)-N-(4-quinolylmethyl)-N-trifluoroacetyl-4-piperidinamine is reacted with 0.068 g (1.78 mmol) of sodium borohydride in analogy to Example 2. The title compound

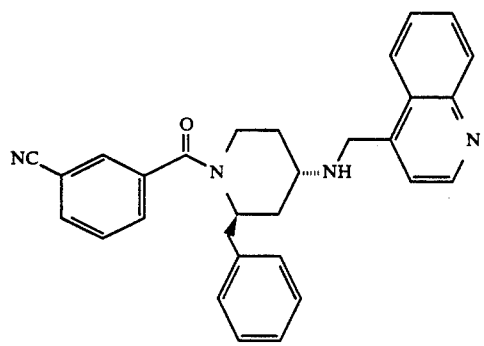

is obtained (0.157 g, 62%) as white foam. TLC: methylene chloride/methanol/conc. ammonia (700:50:1) R/=0.51, FD-MS: M+=460.

The starting compound for this is prepared as follows:

(2R*,4S*)-2-Benzyl-1-(3-cyanobenzoyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted in analogy to Example 4a with 69 mg (0.514 mmol) of 3-cyanobenzoic acid, 143 mg (0.561 mmol) of bis-(2-oxo-3-oxazolidinyl)phosphinic chloride and 144 μl (1.03 mmol) of triethylamine. The title compound (250 mg, 96%) is obtained as white foam. TLC: methylene chloride/methanol/conc. ammonia (700:50:1) R/=0.53, FD-MS: M+=556.

EXAMPLE 49

(2R*,4S*)-2-benzyl-1-(2-chlorobenzoyl)-N-(4-quinolylmethyl)-4-piperidinamine 0.165 g (0.291 mmol) of (2R*,4S*)-2-benzyl-1-(2-chlorobenzoyl)-N-(4-quinolylmethyl)-N-trifluoroacetyl-4-piperidinamine is reacted with 0.044 g (1.16 mmol) of sodium borohydride in analogy to Example 2. The title compound

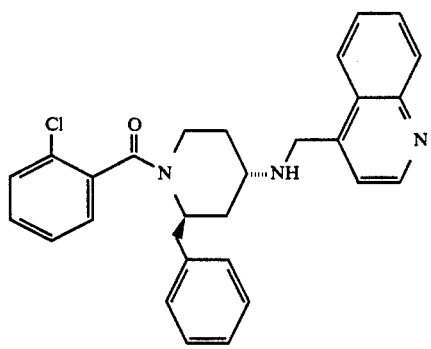

is obtained (0.109 g, 80%) as white foam. TLC: methylene chloride/methanol/conc. ammonia (1000:50:1) R/=0.33, MS: M+=469, 471; IR: 3680, 1640, 1605, 1580 cm$^{-1}$.

The starting compound for this is prepared as follows:

(2R*,4S*)-2-Benzyl-1-(2-chlorobenzoyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-4-piperidinamine are reacted in analogy to Example 4a with 88 mg (0.560 mmol) of 2-chlorobenzoic acid, 143 mg (0.561 mmol) of bis-(2-oxo-3-oxazolidinyl)phosphinic chloride and 144 μl (1.03 mmol) of triethylamine. The title compound (179 mg, 68%) is obtained as white foam. TLC: methylene chloride/methanol/conc. ammonia (2000:50:1) R/=0.42, FD-MS: M+=565, 567.

EXAMPLE 50

(2R*,4S*)-2-benzyl-1-(4-chlorobenzoyl)-N-(4-quinolylmethyl)-4-piperidinamine 0.202 g (0.291 mmol) of (2R*,4S*)-2-benzyl-1-(4-chlorobenzoyl)-N-(4-quinolylmethyl)-N-trifluoroacetyl-4-piperidinamine is reacted with 0.054 g (1.43 mmol) of sodium borohydride in analogy to Example 2. The title compound

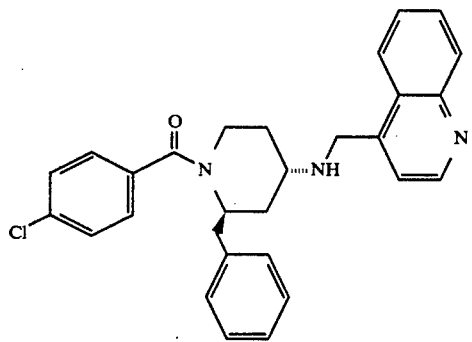

is obtained (0.136 g, 81%) as white foam. TLC: methylene chloride/methanol/conc. ammonia (1000:50:1) R/=0.17, FD-MS: M+=469, 471; IR: 3675, 1625, 1595, 1570 cm$^{-1}$.

The starting compound for this is prepared as follows:

(2R*,4S*)-2-Benzyl-1-(4-chlorobenzoyl)-N-(4-quinolyl-
methyl)-N-trifluoroacetyl-4-piperidinamine 200 mg (0.467 mmol) of (2R*,4S*)-2-benzyl-N-(4-
quinolylmethyl)-N-trifluoroacetyl-4-piperidinaniine are
reacted in analogy to Example 4a with 88 mg (0.560
mmol) of 4-chlorobenzoic acid, 143 mg (0.561 mmol)
bis(2-oxo-3-oxazolidinyl)phosphinic chloride and 144 μl
(1.03 mmol) of triethylamine. The title compound (210
mg, 80%) is obtained as white foam. TLC: methylene
chloride/methanol/conc. ammonia (1000:50:1)
$R_f$=0.44, FD-MS: M+ =565, 567.

EXAMPLE 51

(2R*,4S*)-2-benzyl-1-(9-fluorenyl)-N-(4-quinolylme-
thyl)-4-piperidinamine 130 mg (0.219 mmol) (2R*,4S*)-2-benzyl-1-(9-
fluorenyl)-N-(4-quinolylmethyl)-N-trifluoroacetyl-4-
piperidinamine are reacted in analogy to Example 40
with 500 μl (0.500 mmol) of 1N sodium hydroxide solu-
tion in 1 ml of tetrahydrofuran and 1 ml of methanol.
The title compound

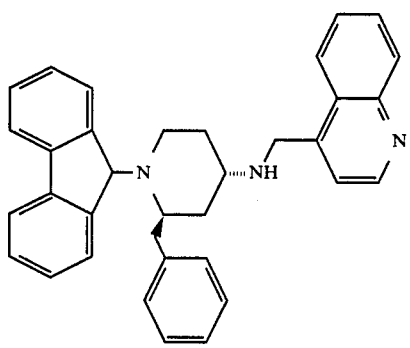

is obtained (49 mg, 45%) as white foam. TLC: toluene-
/ethyl acetate (1:1) $R_f$=0.26; FD-MS: M+ =495.

The starting compound for this is prepared as fol-
lows:

(2R*,4S*)-2-Benzyl-1-(9-fluorenyl)-N-(4-quinolylme-
thyl)-N-trifluoroacetyl-4-piperidinamine 200 mg (0.467 mmol) of (2R*,4S*)-2-benzyl-N-(4-
quinolylmethyl)-N-trifluoroacetyl-4-piperidinamine are
reacted in analogy to Example 25a with 138 mg (0.561
mmol) of 9-bromofluorene and 155 mg (1.12 mmol) of
potassium carbonate in 2.5 ml of acetone. The title com-
pound (131 mg, 47%) is obtained as oil. TLC: toluene-
/ethyl acetate (1:1) $R_f$=0.43; FD-MS: M+ =591.

EXAMPLE 52

(2R*,4S*)-2-benzyl-1-(3,5-dichlorobenzoyl)-N-(4-
quinolylmethyl)-N-methyl-4-piperidinamine 13.4 mg (0.446 mmol) of an 80% strength suspension
of sodium hydride in mineral oil (suspended in hexane
and decanted) are added in one portion to a solution of
150 mg (0.297 mmol) of (2S*,4R*)-2-benzyl-1-(3,5-
dichlorobenzoyl)-N-(4-quinolylmethyl)-4-piperidina-
mine in 2 ml of 1,2-dimethoxyethane at 0° C. After 10
minutes at 0° C., the mixture is left to stir at RT for 30
minutes, again cooled to 0° C., and 22 μl (0.357 mmol)
of methyl iodide are added. The mixture is then stirred
at RT for 96 hours. The solvent is stripped off in a
rotary evaporator, and the residue is chromatographed
on silica gel with toluene/ethyl acetate (1:1). The title
compound

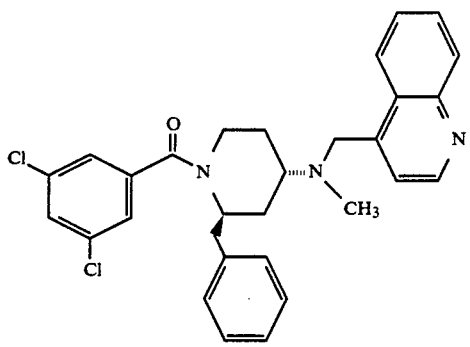

is obtained (20 mg, 13%) as white foam. TLC: toluene-
/ethyl acetate (1:1) $R_f$=0.45; FD-MS: M+ =517, 519.

EXAMPLE 53

(2R*,4S*)-2-benzyl-1-(3,5-dichlorobenzoyl)-N-(4-
quinolylmethyl)-N-cyclohexylcarbamoy-4-piperidina-
mine 200 mg (0.396 mmol) of (2S*,4R*)-2-benzyl-1-(3,5-
dichlorobenzoyl)-N-(4-quinolylmethyl)-4-piperidina-
mine are reacted with 66 μl (0.515 mmol) of cyclohexyl
isocyanate in analogy to Example 16a. The title com-
pound

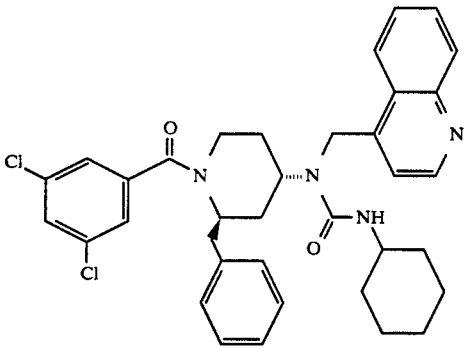

is obtained as white crystals (165 mg, 66%) of melting
point 229° C. (decomposition). TLC: methylene chlori-
de/methanol/conc. ammonia (700:50:1) $R_f$=0.44, FD-
MS: M+ =628, 630.

EXAMPLE 54

(2R*,4S*)-2-benzyl-1-(3,5-dichlorobenzoyl)-N-(4-
quinolylmethyl)-N-phenylcarbamoy-4-piperidinamine 200 mg (0.396 mmol) of (2S*,4R*)-2-benzyl-1-(3,5-
dichlorobenzoyl)-N-(4-quinolylmethyl)-4-piperidina-
mine are reacted with 45 mg (0.377 mmol) of phenyl
isocyanate in analogy to Example 16a. The title com-
pound

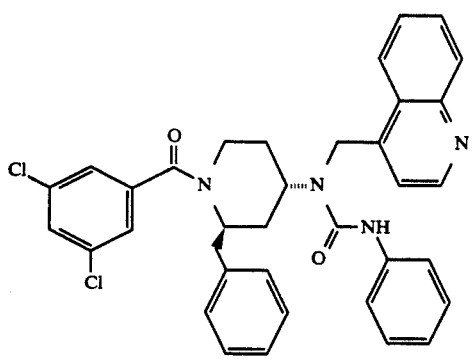

is obtained as solid residue (129 mg, 52%). TLC: methylene chloride/methanol/conc. ammonia (700:50:1) $R_f=0.42$, FD-MS: M+622, 624.

EXAMPLE 55

(2R*,4S*)-2-benzyl-1-(3,5-dichlorobenzoyl)-N-(2-phenylethyl)-4-piperidinamine 0.130 g (0.231 mmol) of (2R*,4S*)-2-benzyl-1-(3,5-dichlorobenzoyl)-N-(2-phenylethyl)-N-trifluoroacetyl-4-piperidinamine is reacted with 0.035 g (0.923 mmol) of sodium borohydride in analogy to Example 2. The title compound

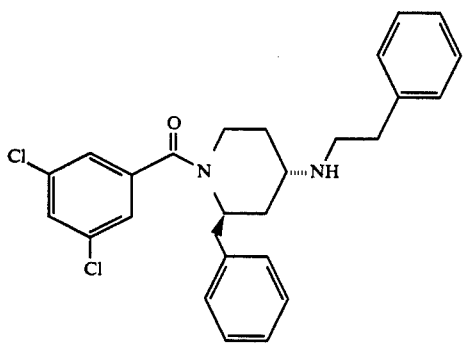

is obtained (0.101 g, 94%) as oil. TLC: methylene chloride/methanol/conc. ammonia (700:50:1) $R_f=0.34$, FD-MS: M+ =466, 468.

The starting compound for this is prepared as follows:

a) (2R*,4S*)-2-Benzyl-1-t-butyloxycarbonyl-N-(2-phenylethyl)-4-piperidinamine 1 g (3.44 mmol) of (2R*,4S*)-2-benzyl-1-t-butyloxycarbonyl-4-piperidinamine is reacted in analogy to Example 11a with 1 ml (4.48 mmol) of phenylacetaldehyde, 0.433 g (6.89 mmol) of sodium cyanoborohydride, 0.791 g (9.64 mmol) of sodium acetate and 434 µl of acetic acid to give the title compound (805 mg, 60%). TLC: methylene chloride/methanol/conc. ammonia (700:50:1) $R_f=0.35$, FD-MS: M+ =394.

b) (2R*,4S*)-2-Benzyl-1-t-butyloxycarbonyl-N-(2-phenylethyl)-N-trifluoroacetyl-4-piperidinamine 618 mg (1.57 mmol) of (2R*,4S*)-2-benzyl-1-t-butyloxycarbonyl-N-(4-quinolylmethyl)-4-piperidinamine are reacted in analogy to Example 2h with 240 µl (1.72 mmol) of trifluoroacetic anhydride and 284 µl (2.04 mmol) of triethylamine. The title compound is obtained as white foam (572 mg, 75%). TLC: toluene/ethyl acetate (9:1) $R_f=0.47$, FD-MS: (M+H)+ =491.

c) (2R*,4S*)-2-Benzyl-N-(2-phenylethyl)-N-trifluoroacetyl-4-piperidinamine 615 mg (1.25 mmol) of (2R*,4S*)-2-benzyl-1-t-butyloxycarbonyl-N-(2-phenylethyl)-N-trifluoroacetyl-4-piperidinamine are reacted with 1.9 ml (25 mmol) of trifluoroacetic acid in analogy to Example 38d. The title compound is obtained as oil (308 mg, 63%). TLC: methylene chloride/methanol/conc. ammonia (700:50:1) $R_f=0.63$, FD-MS: M+ =390.

d) (2R*,4S*)-2-Benzyl-1-(3,5-dichlorobenzoyl)-N-(2-phenylethyl)-N-trifluoroacetyl-4-piperidinamine 189 mg (0.992 mmol) of 3,5-dichlorobenzoic acid are reacted in analogy to Example 2a first with 0.108 ml (1.49 mmol) of thionyl chloride and subsequently with 155 mg (0.397 mmol) of (2R*,4S*)-2-benzyl-N-(2-phenylethyl)-N-trifluoroacetyl-4-piperidinamine and 166 µl (1.19 mmol) of triethylamine to give the title compound (135 mg, 60%). TLC: methylene chloride/methanol/conc. ammonia (1000:50:1) $R_f=0.70$, FD-MS: M+ =562, 564.

EXAMPLE 56

(2R*,4S*)-2-benzyl-1-(3,5-bis(trifluoromethyl)benzoyl)-N-(2-phenylethyl)-4-piperidinamine 0.190 g (0.301 mmol) of (2R*,4S*)-2-benzyl-1-(3,5-bis(trifluoromethyl)benzoyl)-N-(2-phenylethyl)-N-trifluoroacetyl-4-piperidinamine is reacted with 0.046 g (1.21 mmol) of sodium borohydride in analogy to Example 2. The title compound

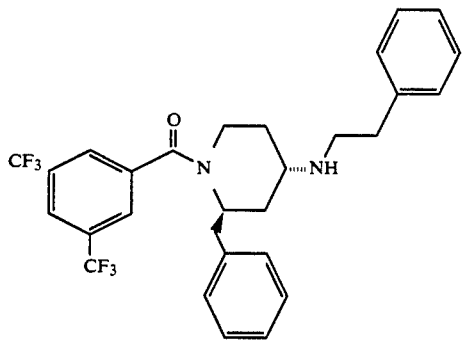

is obtained (0.123 g, 76%) as oil. TLC: methylene chloride/methanol/conc. ammonia (1000:50:1) $R_f=0.22$, FD-MS: M+ =534, IR: 1630 cm$^{-1}$.

The starting compound for this is prepared as follows:

(2R*,4S*)-2-Benzyl-1-(3,5-bis(trifluoromethyl)benzoyl)-N-(2-phenylethyl)-N-trifluoroacetyl-4-piperidinamine 150 mg (0.384 mmol) of (2R*,4S*)-2-benzyl-N-(2-phenylethyl)-N-trifluoroacetyl-4-piperidinamine are reacted in analogy to Example 4a with 93 mg (0.461 mmol) of 3,5-bis(trifluoromethyl)benzoic acid, 117 mg (0.461 mmol) of bis(2-oxo-3-oxazolidinyl)phosphinic chloride and 118 µl (0.845 mmol) of triethylamine. The title compound (191 mg, 79%) is obtained as oil. TLC: methylene chloride/methanol/conc. ammonia (2000:50:1) $R_f=0.79$, FD-MS: M+ =630.

EXAMPLE 57

(2R*,4S*)-2-benzyl-1-(3,5-dichlorobenzoyl)-N-(2-naphthoyl)-4-piperidinamine 142 mg (0.825 mmol) of 2-naphthoic acid are reacted in analogy to Example 2a first with 2 ml (27 mmol) of thionyl chloride and subsequently with 200 mg. (0.550 mmol) of (2R*,4S*)-2-benzyl-1-(3,5-dichlorobenzoyl)-4-piperidinamine and 138 μl (0.991 mmol) of triethylamine to give the title compound (272 mg, 96%).

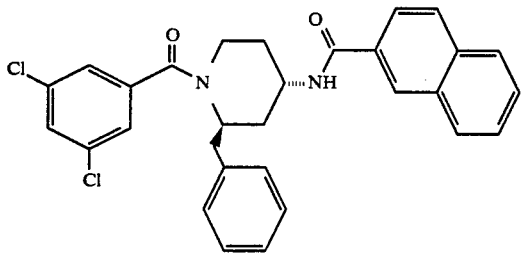

TLC: methylene chloride/methanol/conc. ammonia (1000:50:1) $R_f=0.73$, FD-MS: $(M+H)^+=516$, 518, 520, IR: 3420, 1625 cm$^{-1}$.

The starting compound for this is prepared as follows:

a) (2R*,4S*)-2-Benzyl-4-piperidine azide 15 g (38.3 mmol) of the mixture from Example 2e are reacted with 70 ml of trifluoroacetic acid in analogy to Example 38d. The title compound (7.15 g, 87%) is obtained as oil. TLC: methylene chloride/methanol/conc. ammonia (350:50:1) $R_f=0.57$, FD-MS: $M^+=216$.

b) (2R*,4S*)-2-Benzyl-1-(3,5-dichlorobenzoyl)-4-piperidine azide 6.62 g (34.7 mmol) of 3,5-dichlorobenzoic acid are reacted in analogy to Example 2a first with 3.78 ml (52.0 mmol) of thionyl chloride and subsequently with 3.0 g (13.9 mmol) of (2R*,4S*)-2-benzyl-4-piperidine azide and 5.8 ml (41.6 mmol) of triethylamine to give the title compound (5.18 g, 96%). TLC: methylene chloride/methanol/conc. ammonia (2000:50:1) $R_f=0.77$, DCI-MS: $(M+H)^+=389$, 391.

c) (2R*,4S*)-2-Benzyl-1-(3,5-dichlorobenzoyl)-4-piperidinamine 11.0 g (28.3 mmol) of (2R*,4S*)-2-benzyl-1-(3,5-dichlorobenzoyl)-4-piperidine azide are hydrogenated with 10% Pd/C in analogy to Example 2f. The title compound (8.76 g, 85%) is obtained as oil. TLC: methylene chloride/methanol/conc. ammonia (350:50:1) $R_f=0.40$, FD-MS: $M^+=362$, 364.

EXAMPLE 58

(2R*,4S*)-2-Benzyl-1-(3,5-dichlorobenzoyl)-N-(3,5-dimethylbenzoyl)-4-piperidinamine 124 mg (0.825 mmol) of 3,5-dimethylbenzoic acid are reacted in analogy to Example 2a first with 2 ml (27 mmol) of thionyl chloride and subsequently with 200 mg (0.550 mmol) of (2R*,4S*)-2-benzyl-1-(3,5-dichlorobenzoyl)-4-piperidinamine and 138 μl (0.991 mmol) of triethylamine to give the product (200 mg, 73%).

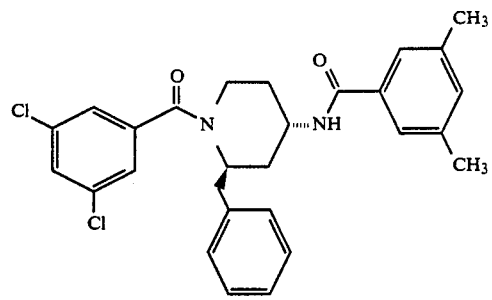

TLC: methylene chloride/methanol/conc. ammonia (2000:50:1) $R_f=0.61$, FD-MS: $(M+H)^+=494$, 496; IR: 3420, 1625 cm$^{-1}$.

EXAMPLE 59

(2R*,4S*)-2-benzyl-1-(3,5-dichlorobenzoyl)-N-(4-quinolycarbonyl)-4-piperidinamine 200 mg (0.550 mmol) of (2R*,4S*)-2-benzyl-1-(3,5-dichlorobenzoyl)-4-piperidinamine are reacted in analogy to Example 4a with 105 mg (0.660 mmol) of quinoline-4-carboxylic acid, 168 mg (0.661 mmol) of bis(2-oxo-3-oxazolidinyl)phosphinic chloride and 169 μl (1.21 mmol) of triethylamine. The title compound

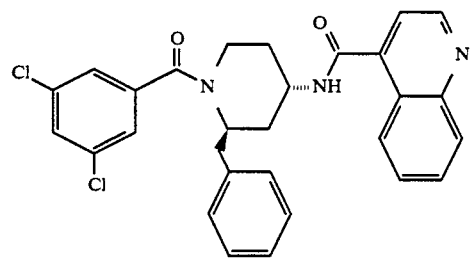

is obtained (278 mg, 97%) as oil. TLC: methylene chloride/methanol/conc. ammonia (700:50:1) $R_f=0.45$, FD-MS: $M^+=517$, 519; IR: 3395, 1755, 1620 cm$^{-1}$.

EXAMPLE 60

(2R*,4S*)-2-benzyl-1-(3,5-dichlorobenzoyl)-N-(3-indolylcarbonyl)-4-piperidinamine 200 mg (0.550 mmol) of (2R*,4S*)-2-benzyl-1-(3,5-dichlorobenzoyl)-4-piperidinamine are reacted in analogy to Example 4a with 106 mg (0.661 mmol) of indole-3-carboxylic acid, 168 mg (0.661 mmol) of bis(2-oxo-3-oxazolidinyl)phosphinic chloride and 169 μl (1.21 mmol) of triethylamine. The title compound

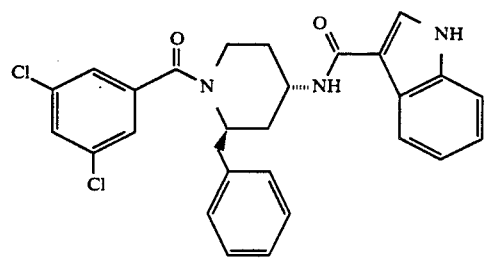

is obtained (92 mg, 33%) as oil. TLC: methylene chloride/methanol/conc. ammonia (350:50:1) R$_f$=0.61, FD-MS: M+=505, 507; IR: 3450, 3260, 1770, 1635 cm$^{-1}$.

EXAMPLE 61

(2R*,4S*)-2-benzyl-1-(3,5-dichlorobenzoyl)-N-(2-indolylcarbonyl)-4-piperidinamine 200 mg (0.550 mmol) of (2R*,4S*)-2-benzyl-1-(3,5-dichlorobenzoyl)-4-piperidinamine are reacted in analogy to Example 4a with 106 mg (0.661 mmol) of indole-2-carboxylic acid, 168 mg (0.661 mmol) of bis(2-oxo-3-oxazolidinyl)phosphinic chloride and 169 μl (1.21 mmol) of triethylamine. The title compound

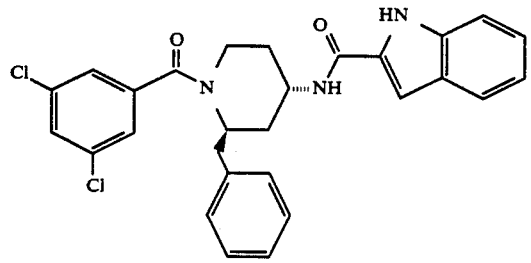

is obtained (89 mg, 32%) as white crystals with melting point 254° C. TLC: methylene chloride/methanol/conc. ammonia (2000:50:1) R$_f$=0.56, FD-MS: M+=505, 507; IR: 3430, 3290, 1625 cm$^{-1}$.

EXAMPLE 62

(2R*,4S*)-2-benzyl-1-(3,5-dichlorobenzoyl)-N-(5-methoxy-2-indolylcarbonyl)-4-piperidinamine 200 mg (0.550 mmol) of (2R*,4S*)-2-benzyl-1-(3,5-dichlorobenzoyl)-4-piperidinamine are reacted in analogy to Example 4a with 126 mg (0.661 mmol) of 5-methoxyindole-2-carboxylic acid, 168 mg (0.661 mmol) of bis(2-oxo-3-oxazolidinyl)phosphinic chloride and 169 μl (1.21 mmol) of triethylamine. The title compound

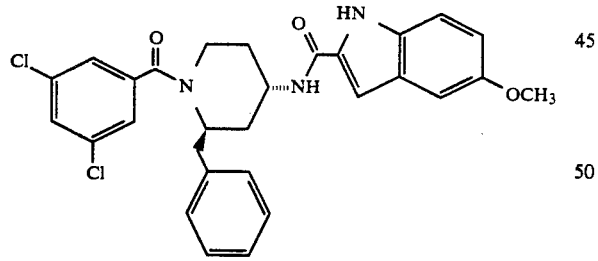

is obtained (118 mg, 41%) as white crystals of melting point 251° C. TLC: methylene chloride/methanol/conc. ammonia (2000:50:1) R$_f$=0.81, FD-MS: M+=535, 537; IR: 3440, 3280, 1625 cm$^{-1}$.

EXAMPLE 63

(2R*,4S*)-2-benzyl-1-(3,5-dichlorobenzoyl)-N-(1-naphthoyl)-4-piperidinamine 150 mg (0.431 mmol) of (2R*,4S*)-2-benzyl-1-(3,5-dichlorobenzoyl)-4-piperidinamine are reacted in analogy to Example 39a with 75 μl (0.495 mmol) of 1-naphthoyl chloride and 81 μl (0.578 mmol) of triethylamine. The title compound

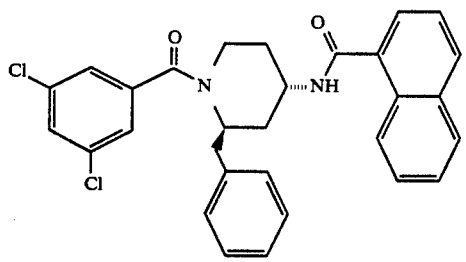

is obtained (208 mg, 97%) as oil. TLC: methylene chloride/methanol/conc. ammonia (1000:50:1) R$_f$=0.85, FD-MS: M+=516, 518; IR: 3680, 3400, 1620 cm$^{-1}$.

EXAMPLE 64

(2R*,4S*)-2-benzyl-1-(3,5-dichlorobenzoyl)-N-(phenylacetyl)-4-piperidinamine 200 mg (0.551 mmol) of (2R*,4S*)-2-benzyl-1-(3,5-dichlorobenzoyl)-4-piperidinamine are reacted in analogy to Example 39a with 88 μl (0.661 mmol) of phenylacetyl chloride and 108 μl (0.771 mmol) of triethylamine. The title compound

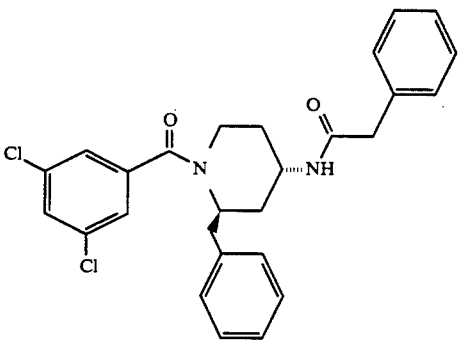

is obtained (127 mg, 48%) as white foam. TLC: methylene chloride/methanol/conc. ammonia (1000:50:1) R$_f$=0.56, FD-MS: M+=480, 482; IR: 3660, 3405, 1665, 1630 cm$^{-1}$.

EXAMPLE 65

(2R*,4S*)-2-benzyl-1-(3,5-dichlorobenzoyl)-N-(2-methoxybenzyl)-4-piperidinamine 200 mg (0.551 mmol) of (2R*,4S*)-2-benzyl-1-(3,5-dichlorobenzoyl)-4-piperidinamine are reacted in analogy to Example 2g with 75 mg (0.551 mmol) of 2-methoxybenzaldehyde and 90 mg magnesium sulfate in 2 ml of toluene and subsequently reduced with 22 mg (0.584 mmol) of sodium borohydride in 2 ml of methanol. The title compound

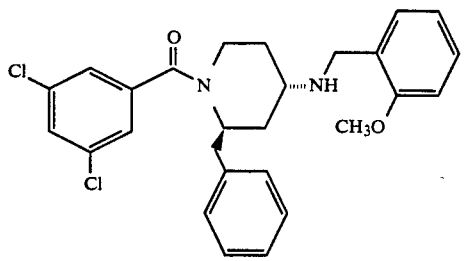

is obtained (170 mg, 64%) as white foam. TLC: methylene chloride/methanol/conc. ammonia (700:50:1) $R_f=0.66$, FD-MS: M+ =482, 482. IR: 1620 cm$^{-1}$.

EXAMPLE 66

(2R*,4S*)-2-benzyl-1-(3,5-dichlorobenzoyl)-N-(3-(N-acetyl)indolylmethyl)-4-piperidinamine 200 mg (0.551 mmol) of (2R*,4S*)-2-benzyl-1-(3,5-dichlorobenzoyl)-4-piperidinamine are reacted in analogy to Example 2g with 113 mg (0.606 mmol) of N-acetylindole-3-carboxaldehyde and 90 mg of magnesium sulfate in 2 ml of toluene and subsequently reduced with 31 mg (0.826 mmol) of sodium borohydride in 3 ml of methanol. The title compound

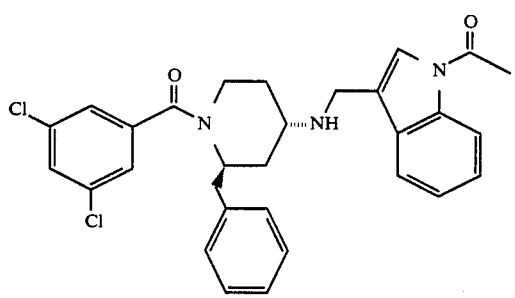

is obtained (30 mg, 10%) as oil. TLC: methylene chloride/methanol/conc. ammonia (1000:50:1) $R_f=0.57$, FD-MS: M+ =533, 535. IR: 1720, 1680, 1635 cm$^{-1}$.

EXAMPLE 67

(2R*,4S*)-2-benzyl-1-(3,5-dichlorobenzoyl)-N-(2-benzo[b]furanylmethyl)-4-piperidinamine 200 mg (0.551 mmol) of (2R*,4S*)-2-benzyl-1-(3,5-dichlorobenzoyl)-4-piperidinamine are reacted in analogy to Example 2g with 97 mg (0.661 mmol) of benzofuran-2-carboxaldehyde and 90 mg of magnesium sulfate in 2 ml of toluene and subsequently reduced with 22 mg (0.584 mmol) of sodium borohydride in 2 ml of methanol. The title compound

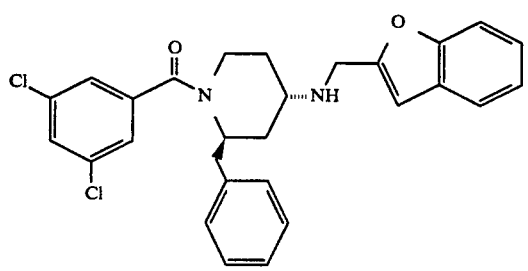

is obtained (150 mg, 55%) as oil. TLC: methylene chloride/methanol/conc. ammonia (2000:50:1) $R_f=0.18$, FD-MS: M+ =492, 494. IR: 1630 cm$^{-1}$.

EXAMPLE 68

(2R*,4S*)-2-benzyl-1-(3,5-dichlorobenzoyl)-N-[(3-methylbenzo[b]-thiophen-2-ylmethyl]-4-piperidinamine 200 mg (0.551 mmol) of (2R*,4S*)-2-benzyl-1-(3,5-dichlorobenzoyl)-4-piperidinamine are reacted in analogy to Example 2g with 116 mg (0.661 mmol) of 3-methylbenzo[b]thiophene-2-carboxaldehyde and 90 mg of magnesium sulfate in 2 ml of toluene and subsequently reduced with 22 mg (0.584 mmol) of sodium borohydride in 2 ml of methanol. The title compound

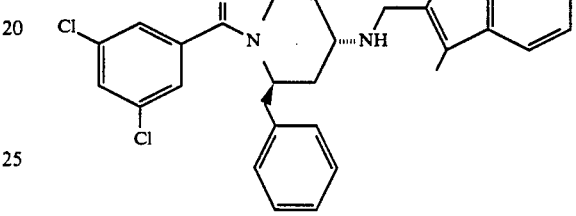

is obtained (75 mg, 25%) as white foam. TLC: methylene chloride/methanol/conc. ammonia (2000:50:1) $R_f=0.38$, FD-MS: M+ =522, 524. IR: 1630 cm$^{-1}$.

EXAMPLE 69

(2R*,4S*)-2-benzyl-1-(3,5-dichlorobenzoyl)-N-(5-methoxyindol-3-ylmethyl-4-piperidinamine 200 mg (0.551 mmol) of (2R*,4S*)-2-benzyl-1-(3,5-dichlorobenzoyl)-4-piperidinamine are reacted in analogy to Example 2g with 116 mg (0.661 mmol) of 5-methoxyindole-3-carboxaldehyde and 90 mg of magnesium sulfate in 2 ml of toluene and subsequently reduced with 22 mg (0.584 mmol) of sodium borohydride in 2 ml of methanol. The title compound

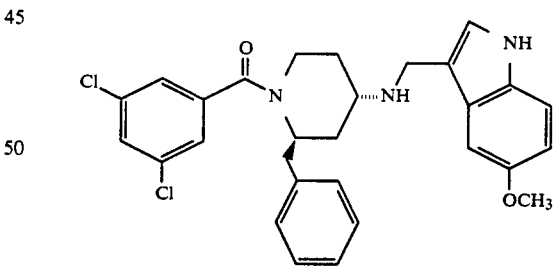

is obtained (98 mg, 34%) as white foam. TLC: methylene chloride/methanol/conc. ammonia (1000:50:1) $R_f=0.42$, FD-MS: M+ =521, 523. IR: 3460, 1630 cm$^{-1}$.

EXAMPLE 70

(2R*,4S*)-2-benzyl-1-(3,5-dichlorobenzoyl)-N-(3-indolylmethyl)-4-piperidinamine 200 mg (0.551 mmol) of (2R*,4S*)-2-benzyl-1-(3,5-dichlorobenzoyl)-4-piperidinamine are reacted in analogy to Example 2g with 80 mg (0.551 mmol) of indole-3-carboxaldehyde and 90 mg of magnesium sulfate in 2 ml of toluene and subsequently reduced with 22 mg (0.584 mmol) of sodium borohydride in 2 ml of methanol. The title compound

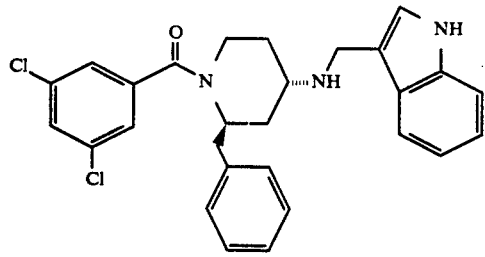

is obtained (75 mg, 28%) as white foam. TLC: methylene chloride/methanol/conc. ammonia (400:50:1) $R_f=0.49$, FD-MS: M+ =491, 493. IR: 3460, 1630 cm$^{-1}$.

EXAMPLE 71

(2R*,4S*)-2-benzyl-1-(3,5-dichlorobenzoyl)-N-phenylcarbamoyl-4-piperidinamine 200 mg (0.551 mmol) of (2R*,4S*)-2-benzyl-1-(3,5-dichlorobenzoyl)-4-piperidinamine are reacted with 85 mg (0.716 mmol) of phenyl isocyanate in analogy to Example 16a. The title compound

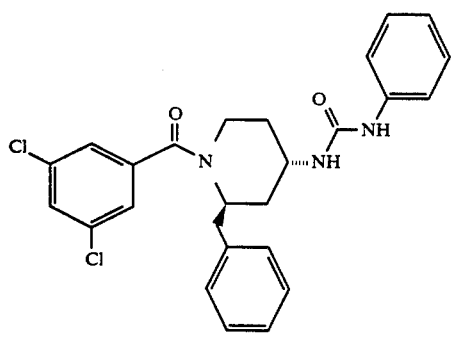

is obtained as white foam (160 mg, 60%). TLC: toluene/ethyl acetate (1:1) $R_f=0.40$, FD-MS: M+ =481, 483; IR: 1600–1690 cm$^{-1}$.

EXAMPLE 72

(2R*,4S*)-2-benzyl-1-(3,5-dichlorobenzoyl)-N-diphenylmethyl-4-piperidinarmine

A solution of 200 mg (0.551 mmol) of (2R*,4S*)-2-benzyl-1-(3,5-dichlorobenzoyl)-4-piperidinamine and 110 mg (0. 606 mmol) of benzophenone in 5 ml of toluene are kept at reflux for 18 hours. The reaction mixture is then concentrated in a rotary evaporator and dissolved in 3 ml of methanol, and 69 mg (1.10 mmol) of sodium cyanoborohydride are added at RT. The reaction mixture is adjusted to pH=5 with 80 μl of acetic acid and stirred at RT for 68 hours. The title compound

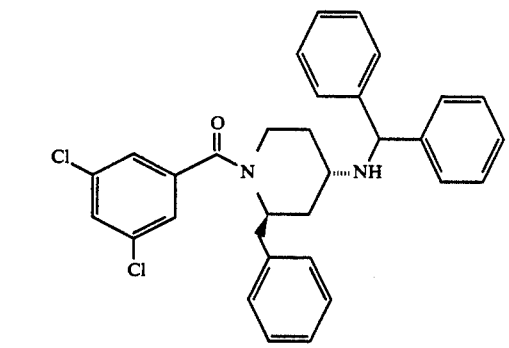

is obtained as white foam (120 mg, 41%). TLC: toluene/ethyl acetate (7:3) $R_f=0.79$, FD-MS: M+ =528, 530; IR: 1630 cm$^{-1}$.

EXAMPLE 73

(2R*,4S*)-2-benzyl-1-(3,5-dichlorobenzoyl)-N-(3,4-dihydro-2H-1-benzopylan-2-carbonyl)-4-piperidinamine 125 mg (0.606 mmol) of N,N'-dicyclohexylcarbodiimide are added to a solution of 108 mg (0.606 mmol) of 3,4-dihydro-2H-1-benzopyran-2-carboxylic acid in 3 ml of tetrahydrofuran at 0° C., and the reaction mixture is stirred for one hour and 177 μl (1.27 mmol) of triethylamine and 200 mg (0.551 mmol) of (2R*,4S*)-2-benzyl-1-(3,5-dichlorobenzoyl)-4-piperidinamine are added. The mixture is allowed to warm to RT and is sirred at this temperature for 16 hours. It is concentrated in a rotary evaporator, the residue is suspended in methylene chloride/ether (1:1), and the white suspension is filtered. After concentration in a rotary evaporator the reaction mixture is taken up in methylene chloride, washed twice with 10% citric acid, once with water, once with 2N sodium hydroxide solution and once with brine, dried over magnesium sulfate and evaporated in a rotary evaporator. The yellow oil is chromatogaphed on silica gel with toluene/ethyl acetate (7:3). The mixture of diastereomers of the title compound

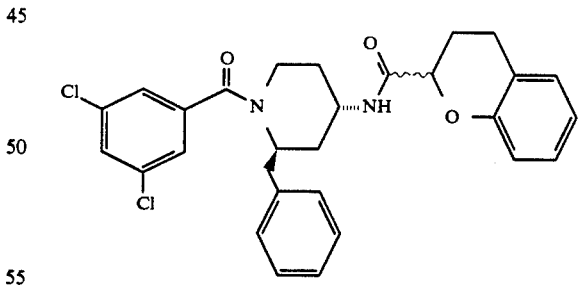

is obtained as white foam (69 mg, 24%). TLC: toluene/ethyl acetate (1:1) $R_f=0.56$, FD-MS: M+ =522, 524; IR: 3410, 1675, 1630 cm$^{-1}$.

EXAMPLE 74

(2R*,4S*)-2-benzyl-1-(4-methoxybenzoyl)-N-(4-quinolylmethyl)-4-piperidinamine 0.175 g (0.321 mmol) of (2R*,4S*)-2-benzyl-1-(4-methoxybenzoyl)-N-(4-quinolylmethyl)-N-trifluoroacetyl-4-piperidinamine is reacted with 0.047 g (1.25 mmol) of sodium borohydride in analogy to Example 2. The title compound

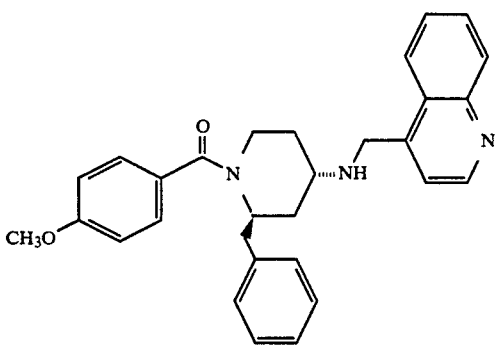

is obtained (0.100 g, 69%) as white foam. TLC: methylene chloride/methanol/conc. ammonia (1000:50:1) $R_f=0.21$, FD-MS: M+ =465; IR: 1620 cm$^{-1}$.

The starting comopund is prepared as follows:

(2R*,4S*)-2-Benzyl-1-(4-methoxybenzoyl)-N-(4-quinolylmethyl)-N-trifluoroacetyl-4-piperidinamine 200 mg (0.467 mmol) of (2R*,4S*)-2-benzyl-N-(4-quinolylmethyl)-N-trifluoroacetyl-1-piperidinamine are reacted in analogy to Example 4a with 85 mg (0.562 mmol) of p-anissic acid, 143 mg (0.561 mmol) of bis(2-oxo-3-oxazolidinyl)phosphinic chloride and 91 μl (0.655 mmol) of triethylamine. The title compound (170 mg, 65%) is obtained as white foam. TLC: methylene chloride/methanol/conc. ammonia (1000:50:1) $R_f=0.37$, FD-MS: M+ =561.

EXAMPLE 75

The following can furthemore be prepared in an analogous manner as in Examples 1 to 74

(2R*,4S*)-2-Benzyl-1-(3,5-dimethylbenzoyl)-N-benzyl-N-carbamoyl-4-piperidinamine;
(2R,4S)-2-Benzyl-1-(3,5-dimethylbenzoyl)-N-(3-phenylpropyl)-4-piperidinamine;
(2S,4S)-2-Benzyl-1-(3,5-dimethylbenzoyl)-N-(3-phenylpropyl)-4-piperidinamine;
(2R,4S)-2-Benzyl-1-(3,5-dimethylbenzoyl)-N-(2-methoxybenzyl)-4-piperidinamine;
(2S,4S)-2-Benzyl-1-(3,5-dimethylbenzoyl)-N-(2-methoxybenzyl)-4-piperidinamine;
(2R,4S)-2-Benzyl-1-(3,5-dimethylbenzoyl)-N-[2-(2-methoxyphenyl)ethyl]-4-piperidinamine;
(2S,4S)-2-Benzyl-1-(3,5-dimethylbenzoyl)-N-[2-(2-methoxyphenyl)ethyl]-4-piperidinamine;
(2R,4S)-2-Benzyl-1-(3,5-dimethylbenzoyl)-N-[3-(2-methoxyphenyl)propyl]-4-piperidinamine;
(2S,4S)-2-Benzyl-1-(3,5-dimethylbenzoyl)-N-[3-(2-methoxyphenyl)propyl]-4-piperidinamine;
(2R,4S)-2-Benzyl-1-(3,5-dimethylbenzoyl)-N-(2-trifluoromethylbenzyl)-4-piperidinamine;
(2S,4S)-2-Benzyl-1-(3,5-dimethylbenzoyl)-N-(2-trifluoromethylbenzyl)-4-piperidinamine;
(2R,4S)-2-Benzyl-1-(3,5-dimethylbenzoyl)-N-[2-(2-trifluoromethylphenyl)ethyl]-4-piperidinamine;
(2S,4S)-2-Benzyl-1-(3,5-dimethylbenzoyl)-N-[2-(2-trifluoromethylphenyl)ethyl]-4-piperidinamine;
(2R,4S)-2-Benzyl-1-(3,5-dimethylbenzoyl)-N-[3-(2-trifluoromethylphenyl)propyl]-4-piperidinamine;
(2S,4S)-2-Benzyl-1-(3,5-dimethylbenzoyl)-N-[3-(2-trifluoromethylphenyl)propyl]-4-piperidinamine;
(2R,4S)-2-Benzyl-1-(3,5-dimethylbenzoyl)-N-(3-trifluoromethylbenzyl)-4-piperidinamine;
(2S,4S)-2-Benzyl-1-(3,5-dimethylbenzoyl)-N-(3-trifluoromethylbenzyl)-4-piperidinamine;
(2R,4S)-2-Benzyl-1-(3,5-dimethylbenzoyl)-N-[2-(3-trifluoromethylphenyl)ethyl]-4-piperidinamine;
(2S,4S)-2-Benzyl-1-(3,5-dimethylbenzoyl)-N-[2-(3-trifluoromethylphenyl)ethyl]-4-piperidinamine;
(2R,4S)-2-Benzyl-1-(3,5-dimethylbenzoyl)-N-[3-(3-trifluoromethylphenyl)propyl]-4-piperidinamine;
(2S,4S)-2-Benzyl-1-(3,5-dimethylbenzoyl)-N-[3-(3-trifluoromethylphenyl)propyl]-4-piperidinamine;
(2R,4S)-2-Benzyl-1-(3,5-dimethylbenzoyl)-N-(4-trifluoromethylbenzyl)-4-piperidinamine;
(2S,4S)-2-Benzyl-1-(3,5-dimethylbenzoyl)-N-(4-trifluoromethylbenzyl)-4-piperidinamine;
(2R,4S)-2-Benzyl-1-(3,5-dimethylbenzoyl)-N-[2-(4-trifluoromethylphenyl)ethyl]-4-piperidinamine;
(2S,4S)-2-Benzyl-1-(3,5-dimethylbenzoyl)-N-[2-(4-trifluoromethylphenyl)ethyl]-4-piperidinamine;
(2R,4S)-2-Benzyl-1-(3,5-dimethylbenzoyl)-N-[3-(4-trifluoromethylphenyl)propyl]-4-piperidinamine;
(2S,4S)-2-Benzyl-1-(3,5-dimethylbenzoyl)-N-[3-(4-trifluoromethylphenyl)propyl]-4-piperidinamine;
(2R,4S)-2-Benzyl-1-(3,5-dimethylbenzoyl)-N-(2,3-dimethoxybenzyl)-4-piperidinamine;
(2S,4S)-2-Benzyl-1-(3,5-dimethylbenzoyl)-N-(2,3-dimethoxybenzyl)-4-piperidinamine;
(2R,4S)-2-Benzyl-1-(3,5-dimethylbenzoyl)-N-[2-(2,3-dimethoxyphenyl)ethyl]-4-piperidinamine;
(2S,4S)-2-Benzyl-1-(3,5-dimethylbenzoyl)-N-[2-(2,3-dimethoxyphenyl)ethyl]-4-piperidinamine;
(2R,4S)-2-Benzyl-1-(3,5-dimethylbenzoyl)-N-[3-(2,3-dimethoxyphenyl)propyl]-4-piperidinamine;
(2S,4S)-2-Benzyl-1-(3,5-dimethylbenzoyl)-N-[3-(2,3-dimethoxyphenyl)propyl]-4-piperidinamine;
(2R,4S)-2-Benzyl-1-(3,5-dimethylbenzoyl)-N-(2,4-dimethoxybenzyl)-4-piperidinamine;
(2S,4S)-2-Benzyl-1-(3,5-dimethylbenzoyl)-N-(2,4-dimethoxybenzyl)-4-piperidinamine;
(2R,4S)-2-Benzyl-1-(3,5-dimethylbenzoyl)-N-[2-(2,4-dimethoxyphenyl)ethyl]-4-piperidinamine;
(2S,4S)-2-Benzyl-1-(3,5-dimethylbenzoyl)-N-[2-(2,4-dimethoxyphenyl)ethyl]-4-piperidinamine;
(2R,4S)-2-Benzyl-1-(3,5-dimethylbenzoyl)-N-[3-(2,4-dimethoxyphenyl)propyl]-4-piperidinamine;
(2S,4S)-2-Benzyl-1-(3,5-dimethylbenzoyl)-N-[3-(2,4-dimethoxyphenyl)propyl]-4-piperidinamine;
(2R,4S)-2-Benzyl-1-(3,5-dimethylbenzoyl)-N-(2,5-dimethoxybenzyl)-4-piperidinamine;
(2S,4S)-2-Benzyl-1-(3,5-dimethylbenzoyl)-N-(2,5-dimethoxybenzyl)-4-piperidinamine;
(2R,4S)-2-Benzyl-1-(3,5-dimethylbenzoyl)-N-[2-(2,5-dimethoxyphenyl)ethyl]-4-piperidinamine;
(2S,4S)-2-Benzyl-1-(3,5-dimethylbenzoyl)-N-[2-(2,5-dimethoxyphenyl)ethyl]-4-piperidinamine;
(2R,4S)-2-Benzyl-1-(3,5-dimethylbenzoyl)-N-[3-(2,5-dimethoxyphenyl)propyl]-4-piperidinamine;
(2S,4S)-2-Benzyl-1-(3,5-dimethylbenzoyl)-N-[3-(2,5-dimethoxyphenyl)propyl]-4-piperidinamine;
(2R,4S)-2-Benzyl-1-(3,5-dimethylbenzoyl)-N-(2,6-dimethoxybenzyl)-4-piperidinamine;
(2S,4S)-2-Benzyl-1-(3,5-dimethylbenzoyl)-N-(2,6-dimethoxybenzyl)-4-piperidinamine;
(2R,4S)-2-Benzyl-1-(3,5-dimethylbenzoyl)-N-[2-(2,6-dimethoxyphenyl)ethyl]-4-piperidinamine;
(2S,4S)-2-Benzyl-1-(3,5-dimethylbenzoyl)-N-[2-(2,6-dimethoxyphenyl)ethyl]-4-piperidinamine;

(2R,4S)-2-Benzyl-1-(3,5-dimethylbenzoyl)-N-[3-(2,6-dimethoxyphenyl)propyl]-4-piperidinamine;
(2S,4S)-2-Benzyl-1-(3,5-dimethylbenzoyl)-N-[3-(2,6-dimethoxyphenyl)propyl]-4-piperidinamine;
(2R,4S)-2-Benzyl-1-(3,5-dimethylbenzoyl)-N-(2,3-methylenedioxybenzyl)-4-piperidinamine;
(2S,4S)-2-Benzyl-1-(3,5-dimethylbenzoyl)-N-(2,3-methylenedioxybenzyl)-4-piperidinamine;
(2R,4S)-2-Benzyl-1-(3,5-dimethylbenzoyl)-N-[2-(2,3-methylenedioxyphenyl)ethyl]-4-piperidinamine;
(2S,4S)-2-Benzyl-1-(3,5-dimethylbenzoyl)-N-[2-(2,3-methylenedioxyphenyl)ethyl]-4-piperidinamine;
(2R,4S)-2-Benzyl-1-(3,5-dimethylbenzoyl)-N-[3-(2,3-methylenedioxyphenyl)propyl]-4-piperidinamine;
(2S,4S)-2-Benzyl-1-(3,5-dimethylbenzoyl)-N-[3-(2,3-methylenedioxyphenyl)propyl]-4-piperidinamine;
(2R,4S)-2-Benzyl-1-(3,5-dimethylbenzoyl)-N-(2,4-methylenedioxybenzyl)-4-piperidinamine;
(2S,4S)-2-Benzyl-1-(3,5-dimethylbenzoyl)-N-(2,4-methylenedioxybenzyl)-4-piperidinamine;
(2R,4S)-2-Benzyl-1-(3,5-dimethylbenzoyl)-N-[2-(2,4-methylenedioxyphenyl)ethyl]-4-piperidinamine;
(2S,4S)-2-Benzyl-1-(3,5-dimethylbenzoyl)-N-[2-(2,4-methylenedioxyphenyl)ethyl]-4-piperidinamine;
(2R,4S)-2-Benzyl-1-(3,5-dimethylbenzoyl)-N-[3-(2,4-methylenedioxyphenyl)propyl]-4-piperidinamine;
(2S,4S)-2-Benzyl-1-(3,5-dimethylbenzoyl)-N-[3-(2,4-methylenedioxyphenyl)propyl]-4-piperidinamine;
(2R,4S)-2-Benzyl-1-(3,5-dimethylbenzoyl)-N-(indol-2-ylmethyl)-4-piperidinamine;
(2S,4S)-2-Benzyl-1-(3,5-dimethylbenzoyl)-N-(indol-2-ylmethyl)-4-piperidinamine;
(2R,4S)-2-Benzyl-1-(3,5-dimethylbenzoyl)-N-(indol-3-ylmethyl)-4-piperidinamine;
(2S,4S)-2-Benzyl-1-(3,5-dimethylbenzoyl)-N-(indol-3-yhnethyl)-4-piperidinamine;
(2S,4S)-2-Benzyl-1-(3,5-dimethylbenzoyl)-N-(quinolin-2-ylmethyl)-4-piperidinamine;
(2S,4S)-2-Benzyl-1-(3,5-dimethylbenzoyl)-N-(quinolin-3-ylmethyl)-4-piperidinamine;
(2R,4S)-2-Benzyl-1-(3,5-dimethylbenzoyl)-N-(2-chlorobenzyl)-4-piperidinamine;
(2S,4S)-2-Benzyl-1-(3,5-dimethylbenzoyl)-N-(2-chlorobenzyl)-4-piperidinamine;
(2R,4S)-2-Benzyl-1-(3,5-dimethylbenzoyl)-N-[2-(2-chlorophenyl)ethyl]-4-piperidinamine;
(2S,4S)-2-Benzyl-1-(3,5-dimethylbenzoyl)-N-[2-(2-chlorophenyl)ethyl]-4-piperidinamine;
(2R,4S)-2-Benzyl-1-(3,5-dimethylbenzoyl)-N-[3-(2-chlorophenyl)propyl]-4-piperidinamine;
(2S,4S)-2-Benzyl-1-(3,5-dimethylbenzoyl)-N-[3-(2-chlorophenyl)propyl]-4-piperidinamine;
(2R,4S)-2-Benzyl-1-(3,5-dimethylbenzoyl)-N-(3-chlorobenzyl)-4-piperidinamine;
(2S,4S)-2-Benzyl-1-(3,5-dimethylbenzoyl)-N-(3-chlorobenzyl)-4-piperidinamine;
(2R,4S)-2-Benzyl-1-(3,5-dimethylbenzoyl)-N-[2-(3-chlorophenyl)ethyl]-4-piperidinamine;
(2S,4S)-2-Benzyl-1-(3,5-dimethylbenzoyl)-N-[2-(3-chlorophenyl)ethyl]-4-piperidinamine;
(2R,4S)-2-Benzyl-1-(3,5-dimethylbenzoyl)-N-[3-(3-chlorophenyl)propyl]-4-piperidinamine;
(2S,4S)-2-Benzyl-1-(3,5-dimethylbenzoyl)-N-[3-(3-chlorophenyl)propyl]-4-piperidinamine;
(2R,4S)-2-Benzyl-1-(3,5-dimethylbenzoyl)-N-(4-chlorobenzyl)-4-piperidinamine;
(2S,4S)-2-Benzyl-1-(3,5-dimethylbenzoyl)-N-(4-chlorobenzyl)-4-piperidinamine;
(2R,4S)-2-Benzyl-1-(3,5-dimethylbenzoyl)-N-[2-(4-chlorophenyl)ethyl]-4-piperidinamine;
(2S,4S)-2-Benzyl-1-(3,5-dimethylbenzoyl)-N-[2-(4-chlorophenyl)ethyl]-4-piperidinamine;
(2R,4S)-2-Benzyl-1-(3,5-dimethylbenzoyl)-N-[3-(4-chlorophenyl)propyl]-4-piperidinamine;
(2S,4S)-2-Benzyl-1-(3,5-dimethylbenzoyl)-N-[3-(4-chlorophenyl)propyl]-4-piperidinamine;
(2R,4S)-2-Benzyl-1-(3,5-dimethylbenzoyl)-N-(4-methoxynaphth-1-ylmethyl)-4-piperidinamine;
(2S,4S)-2-Benzyl-1-(3,5-dimethylbenzoyl)-N-(4-methoxynaphth-1-ylmethyl)-4-piperidinamine;
(2R,4S)-2-Benzyl-1-(3,5-dimethylbenzoyl)-N-(3,4-ethylenedioxybenzyl)-4-piperidinamine;
(2S,4S)-2-Benzyl-1-(3,5-dimethylbenzoyl)-N-(3,4-ethylenedioxybenzyl)-4-piperidinamine;
(2R,4S)-2-Benzyl-1-(3,5-dimethylbenzoyl)-N-(indol-2-ylmethyl)-4-piperidinamine;
(2S,4S)-2-Benzyl-1-(3,5-dimethylbenzoyl)-N-(indol-2-ylmethyl)-4-piperidinamine;
(2R,4S)-2-Benzyl-1-(3,5-dimethylbenzoyl)-N-(indol-3-ylmethyl)-4-piperidinamine;
(2S,4S)-2-Benzyl-1-(3,5-dimethylbenzoyl)-N-(indol-3-ylmethyl)-4-piperidinamine;
(2R,4S)-2-Benzyl-1-(3,5-dimethylbenzoyl)-N-(quinolin-2-ylmethyl)-4-piperidinamine;
(2S,4S)-2-Benzyl-1-(3,5-dimethylbenzoyl)-N-(quinolin-2-ylmethyl)-4-piperidinamine;
(2R,4S)-2-Benzyl-1-(3,5-dimethylbenzoyl)-N-(quinolin-3-ylmethyl)-4-piperidinamine;
(2S,4S)-2-Benzyl-1-(3,5-dimethylbenzoyl)-N-(quinolin-3-ylmethyl)-4-piperidinamine;
(2R,4S)-2-Benzyl-1-(3,5-dimethylbenzoyl)-N-(2-chlorobenzyl)-4-piperidinamine;
(2S,4S)-2-Benzyl-1-(3,5-dimethylbenzoyl)-N-(2-chlorobenzyl)-4-piperidinamine;
(2R,4S)-2-Benzyl-1-(3,5-dimethylbenzoyl)-N-[2-(2-chlorophenyl)ethyl]-4-piperidinamine;
(2S,4S)-2-Benzyl-1-(3,5-dimethylbenzoyl)-N-[2-(2-chlorophenyl)ethyl]-4-piperidinamine;
(2R,4S)-2-Benzyl-1-(3,5-dimethylbenzoyl)-N-[3-(2-chlorophenyl)propyl]-4-piperidinamine;
(2S,4S)-2-Benzyl-1-(3,5-dimethylbenzoyl)-N-[3-(2-chlorophenyl)propyl]-4-piperidinamine;
(2R,4S)-2-Benzyl-1-(3,5-dimethylbenzoyl)-N-(3-chlorobenzyl)-4-piperidinamine;
(2S,4S)-2-Benzyl-1-(3,5-dimethylbenzoyl)-N-(3-chlorobenzyl)-4-piperidinamine;
(2R,4S)-2-Benzyl-1-(3,5-dimethylbenzoyl)-N-[2-(3-chlorophenyl)ethyl]-4-piperidinamine;
(2S,4S)-2-Benzyl-1-(3,5-dimethylbenzoyl)-N-[2-(3-chlorophenyl)ethyl]-4-piperidinamine;
(2R,4S)-2-Benzyl-1-(3,5-dimethylbenzoyl)-N-[3-(3-chlorophenyl)propyl]-4-piperidinamine;
(2S,4S)-2-Benzyl-1-(3,5-dimethylbenzoyl)-N-[3-(3-chlorophenyl)propyl]-4-piperidinamine;
(2R,4S)-2-Benzyl-1-(3,5-dimethylbenzoyl)-N-(4-chlorobenzyl)-4-piperidinamine;
(2S,4S)-2-Benzyl-1-(3,5-dimethylbenzoyl)-N-(4-chlorobenzyl)-4-piperidinamine;
(2R,4S)-2-Benzyl-1-(3,5-dimethylbenzoyl)-N-[2-(4-chlorophenyl)ethyl]-4-piperidinamine;
(2S,4S)-2-Benzyl-1-(3,5-dimethylbenzoyl)-N-[2-(4-chlorophenyl)ethyl]-4-piperidinarnine;
(2R,4S)-2-Benzyl-1-(3,5-dimethylbenzoyl)-N-[3-(4-chlorophenyl)propyl]-4-piperidinamine;
(2S,4S)-2-Benzyl-1-(3,5-dimethylbenzoyl)-N-[3-(4-chlorophenyl)propyl]-4-piperidinamine;

(2R,4S)-2-Benzyl-1-(3,5-dimethylbenzoyl)-N-(4-methoxynaphth-1-ylmethyl)-4-piperidinamine;
(2S,4S)-2-Benzyl-1-(3,5-dimethylbenzoyl)-N-(4-methoxynaphth-1-ylmethyl)-4-piperidinamine;
(2R,4S)-2-Benzyl-1-(3,5-dimethylbenzoyl)-N-(3,4-ethylenedioxybenzyl)-4-piperidinamine;
(2S,4S)-2-Benzyl-1-(3,5-dimethylbenzoyl)-N-(3,4-ethylenedioxybenzyl)-4-piperidinamine;
(2R,4S)-2-Benzyl-1-(3,5-dimethylbenzoyl)-N-(indol-2-ylmethyl)-4-piperidinamine;
(2S,4S)-2-Benzyl-1-(3,5-dimethylbenzoyl)-N-(indol-2-ylmethyl)-4-piperidinamine;
(2R,4S)-2-Benzyl-1-(3,5-dimethylbenzoyl)-N-(indol-3-ylmethyl)-4-piperidinamine;
(2S,4S)-2-Benzyl-1-(3,5-dimethylbenzoyl)-N-(indol-3-ylmethyl)-4-piperidinamine;
(2R,4S)-2-Benzyl-1-(3,5-dimethylbenzoyl)-N-(quinolin-2-ylmethyl)-4-piperidinamine;
(2R,4S)-2-Benzyl-1-(3,5-dimethylbenzoyl)-N-(quinolin-3-ylmethyl)-4-piperidinamine;
(2S,4S)-2-Benzyl-1-(3,5-dimethylbenzoyl)-N-(quinolin-3-ylmethyl)-4-piperidinamine;
(2R,4S)-2-Benzyl-1-(3,5-dimethylbenzoyl)-N-(2-chlorobenzyl)-4-piperidinamine;
(2S,4S)-2-Benzyl-1-(3,5-dimethylbenzoyl)-N-(2-chlorobenzyl)-4-piperidinamine;
(2R,4S)-2-Benzyl-1-(3,5-dimethylbenzoyl)-N-[2-(2-chlorophenyl)ethyl]-4-piperidinamine;
(2S,4S)-2-Benzyl-1-(3,5-dimethylbenzoyl)-N-[2-(2-chlorophenyl)ethyl]-4-piperidinamine;
(2R,4S)-2-Benzyl-1-(3,5-dimethylbenzoyl)-N-[3-(2-chlorophenyl)propyl]-4-piperidinamine;
(2S,4S)-2-Benzyl-1-(3,5-dimethylbenzoyl)-N-[3-(2-chlorophenyl)propyl]-4-piperidinamine;
(2R,4S)-2-Benzyl-1-(3,5-dimethylbenzoyl)-N-(3-chlorobenzyl)-4-piperidinamine;
(2S,4S)-2-Benzyl-1-(3,5-dimethylbenzoyl)-N-(3-chlorobenzyl)-4-piperidinamine;
(2R,4S)-2-Benzyl-1-(3,5-dimethylbenzoyl)-N-[2-(3-chlorophenyl)ethyl]-4-piperidinamine;
(2S,4S)-2-Benzyl-1-(3,5-dimethylbenzoyl)-N-[2-(3-chlorophenyl)ethyl]-4-piperidinamine;
(2R,4S)-2-Benzyl-1-(3,5-dimethylbenzoyl)-N-[3-(3-chlorophenyl)propyl]-4-piperidinamine;
(2S,4S)-2-Benzyl-1-(3,5-dimethylbenzoyl)-N-[3-(3-chlorophenyl)propyl]-4-piperidinamine;
(2R,4S)-2-Benzyl-1-(3,5-dimethylbenzoyl)-N-(4-chlorobenzyl)-4-piperidinamine;
(2S,4S)-2-Benzyl-1-(3,5-dimethylbenzoyl)-N-(4-chlorobenzyl)-4-piperidinamine;
(2R,4S)-2-Benzyl-1-(3,5-dimethylbenzoyl)-N-[2-(4-chlorophenyl)ethyl]-4-piperidinamine;
(2S,4S)-2-Benzyl-1-(3,5-dimethylbenzoyl)-N-[2-(4-chlorophenyl)ethyl]-4-piperidinanamine;
(2R,4S)-2-Benzyl-1-(3,5-dimethylbenzoyl)-N-[3-(4-chlorophenyl)propyl]-4-piperidinamine;
(2S,4S)-2-Benzyl-1-(3,5-dimethylbenzoyl)-N-[3-(4-chlorophenyl)propyl]-4-piperidinamine;
(2R,4S)-2-Benzyl-1-(3,5-dimethylbenzoyl)-N-(4-methoxynaphth-1-ylmethyl)-4-piperidinamine;
(2S,4S)-2-Benzyl-1-(3,5-dimethylbenzoyl)-N-(4-methoxynaphth-1-ylmethyl)-4-piperidinamine;
(2R,4S)-2-Benzyl-1-(3,5-dimethylbenzoyl)-N-(3,4-ethylenedioxybenzyl)-4-piperidinamine;
(2S,4S)-2-Benzyl-1-(3,5-dimethylbenzoyl)-N-(3,4-ethylenedioxybenzyl)-4-piperidinamine;
(2R,4S)-2-Benzyl-1-(3,5-ditrifluoromethylbenzoyl)-N-(indol-2-ylmethyl)-4-piperidinamine;
(2S,4S)-2-Benzyl-1-(3,5-ditrifluoromethylbenzoyl)-N-(indol-2-ylmethyl)-4-piperidinamine;
(2R,4S)-2-Benzyl-1-(3,5-ditrifluoromethylbenzoyl)-N-(indol-3-ylmethyl)-4-piperidinamine;
(2S,4S)-2-Benzyl-1-(3,5-ditrifluoromethylbenzoyl)-N-(indol-3-ylmethyl)-4-piperidinamine;
(2R,4S)-2-Benzyl-1-(3,5-ditrifluoromethylbenzoyl)-N-(quinolin-2-ylmethyl)-4-piperidinamine;
(2S,4S)-2-Benzyl-1-(3,5-ditrifluoromethylbenzoyl)-N-(quinolin-2-ylmethyl)-4-piperidinamine;
(2R,4S)-2-Benzyl-1-(3,5-ditrifluoromethylbenzoyl)-N-(quinolin-3-ylmethyl)-4-piperidinamine;
(2S,4S)-2-Benzyl-1-(3,5-ditrifluoromethylbenzoyl)-N-(quinolin-3-ylmethyl)-4-piperidinamine;
(2R,4S)-2-Benzyl-1-(3,5-ditrifluoromethylbenzoyl)-N-(2-chlorobenzyl)-4-piperidinamine;
(2S,4S)-2-Benzyl-1-(3,5-ditrifluoromethylbenzoyl)-N-(2-chlorobenzyl)-4-piperidinamine;
(2R,4S)-2-Benzyl-1-(3,5-ditrifluoromethylbenzoyl)-N-[2-(2-chlorophenyl)ethyl]-4-piperidinamine;
(2S,4S)-2-Benzyl-1-(3,5-ditrifluoromethylbenzoyl)-N-[2-(2-chlorophenyl)ethyl]-4-piperidinamine;
(2R,4S)-2-Benzyl-1-(3,5-ditrifluoromethylbenzoyl)-N-[3-(2-chlorophenyl)propyl]-4-piperidinamine;
(2S,4S)-2-Benzyl-1-(3,5-ditrifluoromethylbenzoyl)-N-[3-(2-chlorophenyl)propyl]-4-piperidinamine;
(2R,4S)-2-Benzyl-1-(3,5-ditrifluoromethylbenzoyl)-N-(3-chlorobenzyl)-4-piperidinamine;
(2S,4S)-2-Benzyl-1-(3,5-ditrifluoromethylbenzoyl)-N-(3-chlorobenzyl)-4-piperidinamine;
(2R,4S)-2-Benzyl-1-(3,5-ditrifluoromethylbenzoyl)-N-[2-(3-chlorophenyl)ethyl]-4-piperidinamine;
(2S,4S)-2-Benzyl-1-(3,5-ditrifluoromethylbenzoyl)-N-[2-(3-chlorophenyl)ethyl]-4-piperidinamine;
(2R,4S)-2-Benzyl-1-(3,5-ditrifluoromethylbenzoyl)-N-[3-(3-chlorophenyl)propyl]-4-piperidinamine;
(2S,4S)-2-Benzyl-1-(3,5-ditrifluoromethylbenzoyl)-N-[3-(3-chlorophenyl)propyl]-4-piperidinamine;
(2R,4S)-2-Benzyl-1-(3,5-ditrifluoromethylbenzoyl)-N-(4-chlorobenzyl)-4-piperidinamine;
(2S,4S)-2-Benzyl-1-(3,5-ditrifluoromethylbenzoyl)-N-(4-chlorobenzyl)-4-piperidinamine;
(2R,4S)-2-Benzyl-1-(3,5-ditrifluoromethylbenzoyl)-N-[2-(4-chlorophenyl)ethyl]-4-piperidinamine;
(2S,4S)-2-Benzyl-1-(3,5-ditrifluoromethylbenzoyl)-N-[2-(4-chlorophenyl)ethyl]-4-piperidinamine;
(2R,4S)-2-Benzyl-1-(3,5-ditrifluoromethylbenzoyl)-N-[3-(4-chlorophenyl)propyl]-4-piperidinamine;
(2S,4S)-2-Benzyl-1-(3,5-ditrifluoromethylbenzoyl)-N-[3-(4-chlorophenyl)propyl]-4-piperidinamine;
(2R,4S)-2-Benzyl-1-(3,5-ditrifluoromethylbenzoyl)-N-(4-methoxynaphth-1-ylmethyl)-4-piperidinamine;
(2S,4S)-2-Benzyl-1-(3,5-ditrifluoromethylbenzoyl)-N-(4-methoxynaphth-1-ylmethyl)-4-piperidinamine;
(2R,4S)-2-Benzyl-1-(3,5-ditrifluoromethylbenzoyl)-N-(3,4-ethylenedioxybenzyl)-4-piperidinamine;
(2S,4S)-2-Benzyl-1-(3,5-ditrifluoromethylbenzoyl)-N-(3,4-ethylenedioxybenzyl)-4-piperidinamine;
(2R,4S)-2-Benzyl-1-(3,5-dichlorobenzoyl)-N-(indol-2-ylmethyl)-4-piperidinamine;
(2S,4S)-2-Benzyl-1-(3,5-dichlorobenzoyl)-N-(indol-2-ylmethyl)-4-piperidinamine;
(2R,4S)-2-Benzyl-1-(3,5-dichlorobenzoyl)-N-(indol-3-ylmethyl)-4-piperidinamine;
(2S,4S)-2-Benzyl-1-(3,5-dichlorobenzoyl)-N-(indol-3-ylmethyl)-4-piperidinamine;
(2R,4S)-2-Benzyl-1-(3,5-dichlorobenzoyl)-N-(quinolin-2-ylmethyl)-4-piperidinamine;

(2S,4S)-2-Benzyl-1-(3,5-dichlorobenzoyl)-N-(quinolin-2-ylmethyl)-4-piperidinamine;
(2R,4S)-2-Benzyl-1-(3,5-dichlorobenzoyl)-N-(quinolin-3-ylmethyl)-4-piperidinamine;
(2S,4S)-2-Benzyl-1-(3,5-dichlorobenzoyl)-N-(quinolin-3-ylmethyl)-4-piperidinamine;
(2R,4S)-2-Benzyl-1-(3,5-dichlorobenzoyl)-N-(2-chlorobenzyl)-4-piperidinamine;
(2S,4S)-2-Benzyl-1-(3,5-dichlorobenzoyl)-N-(2-chlorobenzyl)-4-piperidinamine;
(2R,4S)-2-Benzyl-1-(3,5-dichlorobenzoyl)-N-[2-(2-chlorophenyl)ethyl]-4-piperidinamine;
(2S,4S)-2-Benzyl-1-(3,5-dichlorobenzoyl)-N-[2-(2-chlorophenyl)ethyl]-4-piperidinamine;
(2R,4S)-2-Benzyl-1-(3,5-dichlorobenzoyl)-N-[3-(2-chlorophenyl)propyl]-4-piperidinamine;
(2S,4S)-2-Benzyl-1-(3,5-dichlorobenzoyl)-N-[3-(2-chlorophenyl)propyl]-4-piperidinamine;
(2R,4S)-2-Benzyl-1-(3,5-dichlorobenzoyl)-N-(3-chlorobenzyl)-4-piperidinamine;
(2S,4S)-2-Benzyl-1-(3,5-dichlorobenzoyl)-N-(3-chlorobenzyl)-4-piperidinamine;
(2R,4S)-2-Benzyl-1-(3,5-dichlorobenzoyl)-N-[2-(3-chlorophenyl)ethyl]-4-piperidinamine;
(2S,4S)-2-Benzyl-1-(3,5-dichlorobenzoyl)-N-[2-(3-chlorophenyl)ethyl]-4-piperidinamine;
(2R,4S)-2-Benzyl-1-(3,5-dichlorobenzoyl)-N-[3-(3-chlorophenyl)propyl]-4-piperidinamine;
(2S,4S)-2-Benzyl-1-(3,5-dichlorobenzoyl)-N-[3-(3-chlorophenyl)propyl]-4-piperidinamine;
(2R,4S)-2-Benzyl-1-(3,5-dichlorobenzoyl)-N-(4-chlorobenzyl)-4-piperidinamine;
(2S,4S)-2-Benzyl-1-(3,5-dichlorobenzoyl)-N-(4-chlorobenzyl)-4-piperidinamine;
(2R,4S)-2-Benzyl-1-(3,5-dichlorobenzoyl)-N-[2-(4-chlorophenyl)ethyl]-4-piperidinamine;
(2S,4S)-2-Benzyl-1-(3,5-dichlorobenzoyl)-N-[2-(4-chlorophenyl)ethyl]-4-piperidinamine;
(2R,4S)-2-Benzyl-1-(3,5-dichlorobenzoyl)-N-[3-(4-chlorophenyl)propyl]-4-piperidinamine;
(2S,4S)-2-Benzyl-1-(3,5-dichlorobenzoyl)-N-[3-(4-chlorophenyl)propyl]-4-piperidinamine;
(2R,4S)-2-Benzyl-1-(3,5-dichlorobenzoyl)-N-(4-methoxynaphth-1-ylmethyl)-4-piperidinamine;
(2S,4S)-2-Benzyl-1-(3,5-dichlorobenzoyl)-N-(4-methoxynaphth-1-ylmethyl)-4-piperidinamine;
(2R,4S)-2-Benzyl-1-(3,5-dichlorobenzoyl)-N-(3,4-ethylenedioxybenzyl)-4-piperidinamine;
(2S,4S)-2-Benzyl-1-(3,5-dichlorobenzoyl)-N-(3,4-ethylenedioxybenzyl)-4-piperidinamine;
(2R,4S)-2-Benzyl-1-(3,5-dimethoxybenzoyl)-N-(indol-2-ylmethyl)-4-piperidinamine;
(2S,4S)-2-Benzyl-1-(3,5-dimethoxybenzoyl)-N-(indol-2-ylmethyl)-4-piperidinamine;
(2R,4S)-2-Benzyl-1-(3,5-dimethoxybenzoyl)-N-(indol-3-ylmethyl)-4-piperidinamine;
(2S,4S)-2-Benzyl-1-(3,5-dimethoxybenzoyl)-N-(indol-3-ylmethyl)-4-piperidinamine;
(2R,4S)-2-Benzyl-1-(3,5-dimethoxybenzoyl)-N-(quinolin-2-ylmethyl)-4-piperidinanidne;
(2S,4S)-2-Benzyl-1-(3,5-dimethoxybenzoyl)-N-(quinolin-2-ylmethyl)-4-piperidinamine;
(2R,4S)-2-Benzyl-1-(3,5-dimethoxybenzoyl)-N-(quinolin-3-ylmethyl)-4-piperidinamine;
(2S,4S)-2-Benzyl-1-(3,5-dimethoxybenzoyl)-N-(quinolin-3-ylmethyl)-4-piperidinamine;
(2R,4S)-2-Benzyl-1-(3,5-dimethoxybenzoyl)-N-(2-chlorobenzyl)-4-piperidinamine;
(2S,4S)-2-Benzyl-1-(3,5-dimethoxybenzoyl)-N-(2-chlorobenzyl)-4-piperidinamine;
(2R,4S)-2-Benzyl-1-(3,5-dimethoxybenzoyl)-N-[2-(2-chlorophenyl)ethyl]-4-piperidinamine;
(2S,4S)-2-Benzyl-1-(3,5-dimethoxybenzoyl)-N-[2-(2-chlorophenyl)ethyl]-4-piperidinamine;
(2R,4S)-2-Benzyl-1-(3,5-dimethoxybenzoyl)-N-[3-(2-chlorophenyl)propyl]-4-piperidinamine;
(2S,4S)-2-Benzyl-1-(3,5-dimethoxybenzoyl)-N-[3-(2-chlorophenyl)propyl]-4-piperidinamine;
(2R,4S)-2-Benzyl-1-(3,5-dimethoxybenzoyl)-N-(3-chlorobenzyl)-4-piperidinamine;
(2S,4S)-2-Benzyl-1-(3,5-dimethoxybenzoyl)-N-(3-chlorobenzyl)-4-piperidinamine;
(2R,4S)-2-Benzyl-1-(3,5-dimethoxybenzoyl)-N-[2-(3-chlorophenyl)ethyl]-4-piperidinamine;
(2S,4S)-2-Benzyl-1-(3,5-dimethoxybenzoyl)-N-[2-(3-chlorophenyl)ethyl]-4-piperidinamine;
(2R,4S)-2-Benzyl-1-(3,5-dimethoxybenzoyl)-N-[3-(3-chlorophenyl)propyl]-4-piperidinamine;
(2S,4S)-2-Benzyl-1-(3,5-dimethoxybenzoyl)-N-[3-(3-chlorophenyl)propyl]-4-piperidinamine;
(2R,4S)-2-Benzyl-1-(3,5-dimethoxybenzoyl)-N-(4-chlorobenzyl)-4-piperidinamine;
(2S,4S)-2-Benzyl-1-(3,5-dimethoxybenzoyl)-N-(4-chlorobenzyl)-4-piperidinamine;
(2R,4S)-2-Benzyl-1-(3,5-dimethoxybenzoyl)-N-[2-(4-chlorophenyl)ethyl]-4-piperidinamine;
(2S,4S)-2-Benzyl-1-(3,5-dimethoxybenzoyl)-N-[2-(4-chlorophenyl)ethyl]-4-piperidinamine;
(2R,4S)-2-Benzyl-1-(3,5-dimethoxybenzoyl)-N-[3-(4-chlorophenyl)propyl]-4-piperidinamine;
(2S,4S)-2-Benzyl-1-(3,5-dimethoxybenzoyl)-N-[3-(4-chlorophenyl)propyl]-4-piperidinamine;
(2R,4S)-2-Benzyl-1-(3,5-dimethoxybenzoyl)-N-(4-methoxynaphth-1-ylmethyl)-4-piperidinamine;
(2S,4S)-2-Benzyl-1-(3,5-dimethoxybenzoyl)-N-(4-methoxynaphth-1-ylmethyl)-4-piperidinamine;
(2R,4S)-2-Benzyl-1-(3,5-dimethoxybenzoyl)-N-(3,4-ethylenedioxybenzyl)-4-piperidinamine and
(2S,4S)-2-Benzyl-1-(3,5-dimethoxybenzoyl)-N-(3,4-ethylenedioxybenzyl)-4-piperidinamine.

EXAMPLE 76

(2R,4S)- and (2R,4R)2-benzyl-1-(3,5-dimethylbenzoyl)-N-(4-quinolylmethyl)-4-piperidinamine dihydrochloride A mixture of the hydrochlorides of the two diastereomeric title compounds is obtained in analogy to Example 1 starting from 1.26 g (3.9 mmol) of (2R,4R/S)-2-benzyl-1-(3,5-dimethylbenzoyl)-4-piperidinamine, obtained as mixture of about 70% of (2R,4R)- and about 30% of (2R,4S)-diastereomers by reduction with borane/dimethyl sulfide according to Example e1b, and using a total of 2.26 g (14.4 mmol) of quinoline-4-carboxaldehyde.

Diasteromer A

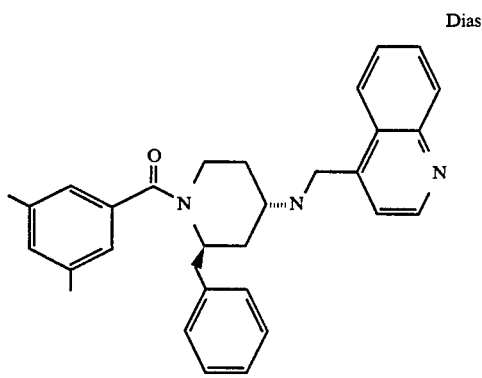

Diastereomer B

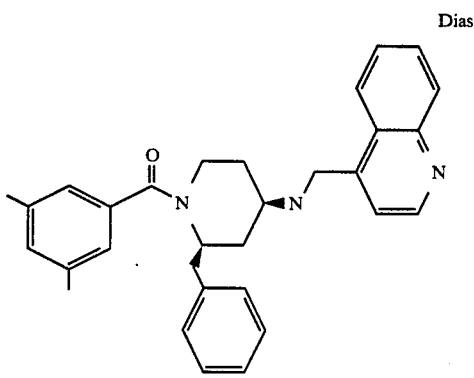

TLC: methylene chloride/methanol/conc. ammonia (90:9:1)

Diastereomer A (2R,4R): $R_f$=0.5, MS: M+ =463

Diastereomer B (2S,4S): $R_f$=0.45, MS: M+ =463, melting point 144°–145°, $[\alpha]_D$= +25° (c=0.94 in ethanol)

These are treated, dissolved in ethyl acetate, with ethereal HCl solution, resulting in the dihydrochloride of the title compound.

TLC: methylene chloride/methanol/conc. ammonia (90:9:1)

Diastereomer A (2R,4R): $R_f$=0.5, melting point 172°–174°, $[\alpha]_D$= −55.7° (c=1, ethanol)

Diastereomer B (2S,4S): $R_f$=0.45, melting point 174°–176°, $[\alpha]_D$= +18° (c=1, ethanol)

EXAMPLE 77

(2S,4R) and (2S,4S)-2-benzyl-1-(3,5-dimethylbenzoyl)-N-(2-phenethyl)-4-piperidinamine hydrochloride The hydrochlorides of the two diastereomeric title compounds are obtained in analogy to Example 1 starting from 1.87 g (5.8 mmol) of (2S,4R/S)-2-benzyl-1-(3,5-dimethylbenzoyl)-4-piperidinamine, obtained as mixture of about 70% of (2S,4S)- and about 30% of (2S,4R)- diastereomers by reduction using borane/dimethyl sulfide according to Example e1b, and using phenylacetaldehyde. TLC: methylene chloride/methanol (98:2)

Diastereomer A (2S,4S): $R_f$=0.16, melting point 250°–251° C., $[\alpha]_D$= +56.2° (c=0.980, methanol), MS: M+ =426 (free base).

Diastereomer B (2S,4R): $R_f$=0.06, melting point 250° C. (decomposition), $[\alpha]_D$= −29.7° (c=0.768, methanol), MS: M+ =426 (free base).

EXAMPLE 78

(2R,4S)-2-benzyl-1-(3,5-dimethylbenzoyl)-N-(3-quinolylmethyl)-4-piperidinamine

The title compound is obtained in the form of colourless crystals in analogy to Example 1 starting from 511 mg (1.59 mmol) of (2R,4RS)-2-benzyl-1-(3,5-dimethylbenzoyl)-4-piperidinamine using quinoline-3-carbaldehyde and by crystallisation from hexane/ethyl acetate (1:1).

TLC: methylene chloride/methanol/conc. ammonia (90:9:1)

$R_f$=0.5, melting point 91°–93° C., MS: M+ =463 (free base), $[\alpha]_D$= +0.70 (c=1.09, methanol)

EXAMPLE 79

(2R,4S)-2-benzyl-1-(3,5-dimethylbenzoyl)-N-(2-quinolylmethyl)-4-piperidinamine dihydrochloride The dihydrochlorides of the title compound are obtained in analogy to Example 1 starting from 541 mg (1.68 mmol) of (2R,4RS)-2-benzyl-1-(3,5-dimethylbenzoyl)-4-piperidinamine using quinoline-2-carbaldehyde.

TLC: methylene chloride/methanol/conc. ammonia (90:9:1)

$R_f$=0.5, decomposition point: from 110° C., MS: M+ =463 (free base), $[\alpha]_D$= +4.80° (c=1.105, methanol)

EXAMPLE 80

(2R,4S)- and (2R,4R)-2-benzyl-1-(3,5-dimethylbenzoyl)-N-benzyl-4-piperidinamine hydrochloride The hydrochlorides of the two diastereomeric title compounds are obtained in analogy to Example 1 starting from 0.748 g (2.32mmol) of (2R,4R/S)-2-benzyl-1-(3,5-dimethylbenzoyl)-4-piperidinamine, obtained as mixture of about 70% of (2R,4R)- and about 30% of (2R,4S)- diastereomers by reduction using borane/dimethyl sulfide according to Example e1b, and using benzaldehyde.

TLC: methylene chloride/methanol/conc. ammonia (95:4.5:0.5)

Diastereomer A (2R,4R): $R_f$=0.45, melting point 244°–246° C., $[\alpha]_D$= −50.4° (c=0.979,chloroform), MS: M+ =412 (free base).

Diastereomer B (2R,4S): $R_f$=0.33, amorphous. $[\alpha]_D$= +7.9° (c=1.0,chloroform), MS: M+ =412 (free base).

EXAMPLE 81

(2S,4R)- and (2S,4S)-2-benzyl-1-(3,5-dimethylbenzoyl)-N-benzyl-4-piperidinamine hydrochloride The hydrochlorides of the two diastereomeric title compounds are obtained in analogy to Example 1 starting from 4.5 g (13.95mmol) of (2S,4R/S)-2-benzyl-1-(3,5-dimethylbenzoyl)-4-piperidinamine, obtained as mixture of about 70% of (2S,4S)- and about 30% of (2S,4R)- diastereomers by reduction using borane/dimethyl sulfide according to Example e1b, and using benzaldehyde.

TLC: methylene chloride/methanol/conc. ammonia (95:4.5:0.5)

Diastereomer A (2S,4S): $R_f$=0.45, melting point 246°–247° C., $[\alpha]_D$= +51.21 (c=0.672,chloroform), MS: M+ =412 (free base).

Diastereomer B (2S,4R): $R_f$=0.33, amorphous. $[α]_D$= −7.7° (c=0.784, chloroform), MS: M+ =412 (free base).

EXAMPLE 82

(2R,4S)- and (2R,4R)-2-benzyl-1-(3,5-dimethylbenzoyl)-N-(4-pyridylmethyl)-4-piperidinamine dihydrochloride The dihydrochlorides of the two diastereomeric title compounds are obtained in analogy to Example 1 starring from 100 mg (0.279 mmol) of (2R,4R/S)-2-benzyl-1-(3,5-dimethylbenzoyl)-4-piperidinamine, obtained as mixture of about 70% of (2R,4R)- and about 30% of (2R,4S)- diastereomers by reducing using borane-/dimethyl sulfide according to Example e1b, and using pyridine-4-carbaldehyde.

TLC: methylene chloride/methanol/conc. ammonia (9°:9:1)

Diastereomer A (2R,4R): $R_f$=0.68, from 142° C. decomposition, $[α]_D$= −57.3° (c=0,508, ethanol), MS: M+ =413 (free base).

Diastereomer B (2R,4S): $R_f$=0.44, from 145° C. decomposition, $[α]_D$= +23.0° (c=0.300, ethanol), MS: M+ =413 (free base).

EXAMPLE 83

(2R,4S)- and (2R,4R)-2-benzyl-1-(3,5-dimethylbenzoyl)-N-(3-pyridylmethyl)-4-piperidinamine dihydrochloride The dihydrochlorides of the two diastereomeric title compounds are obtained in analogy to Example 1 starting from 100 mg (0.279 mmol) of (2R,4R/S)-2-benzyl-1-(3,5-dimethylbenzoyl)-4-piperidinamine, obtained as mixture of about 70% of (2R,4R)- and about 30% of (2R,4S)- diastereomers by reducing using borane-/dimethyl sulfide according to Example e1b, and using pyridine-3-carbaldehyde.

TLC: methylene chloride/methanol/conc. ammonia (90:9:1)

Diastereomer A (2R,4R): $R_f$=0.68, from 105° C. decomposition, $[α]_D$= −52.6° (c=1.06, ethanol), MS: M+ =413 (free base).

Diastereomer B (2R,4S): $R_f$=0.44, from 105° C. decomposition, $[α]_D$= +22.6°) (c=1.03, ethanol), MS: M+ =413 (free base).

EXAMPLE 84

(2S,4R) and (2S,4S)-2-benzyl-1-(3,5-dimethylbenzoyl)-N-(4-quinolylmethyl)-4-piperidinamine The analogy to Example 1 starting from 12.1 g (37.5 mmol) of (2S,4RS)-2-benzyl-1-(3,5-dimethylbenzoyl)-4-piperidinamine, obtained as mixture of about 70% of (2S,4S)- and about 30% of (2S,4R)- diastereomers by reduction using borane/dimethyl sulfide according to Example e1b, and using quinoline-4-carbaldehyde.

TLC: methylene chloride/methanol/conc. ammonia (90:9:1)

Diastereomer A (2S,4R): $R_f$=0.59, melting point 144°–145° C. (free base) $[α]_D$= −25.1° (c=1.0, ethanol), MS: M+ =463 (free base)

EXAMPLE 85

(2R*,4S*,1′R*)-N-Benzyl-1-(3,5-dimethylbenzoyl)-2-(1′-hydroxy-1′-benzyl)-4-piperidin-amine (diastereomer A) and

(2R*,4R*,1′R*)-N-benzyl-1-(3,5-dimethylbenzoyl)-2-(1′-hydroxy-1′-phenyl-methyl)-4-piperidinamine (diastereomer B)

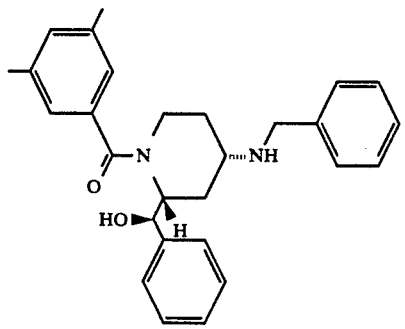

A

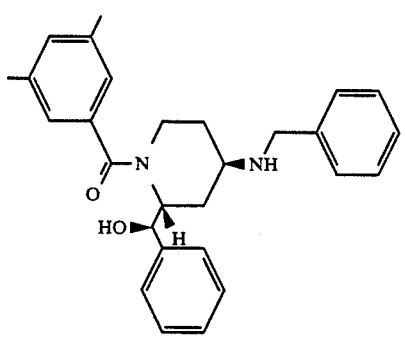

B

A solution of 400 mg (1.18 mmol) of (2R*,1′R*-1-(3,5-dimethylbenzoyl)-2-(1′-hydroxy-1′-phenyl-methyl)-4-piperidone and 139 mg (1.3 mmol) benzylamine in toluene/hexane is heated to reflux with azeotropic removal of water for 18 hours. The reaction mixture is concentrated under reduced pressure, and the remaining oil is taken off in methanol and, at 0° to 5°, 111 mg of sodium cyanoborohydride (85% in mineral oil) are added and stirred at 25° for 4 hours. The solvent is stripped off under reduced pressure, and the crude product is taken up in a mixture of ethyl acetate and 10% strength sodium carbonate solution. The organic phase is separated off, dried over sodium sulfate and evaporated under reduced pressure. Chromatography on silica gel with ethyl acetate as mobile phase yields the title compounds; TLC (ethyl acetate):

Diastereomer A: $R_f$=0.28; melting point 159°–160°
Diastereomer B: $R_f$=0.09; melting point 190°–192°.

The starting material can be prepared as follows:

a) 1-tert-Butoxycarbonyl-4-piperidone ethylene ketal 26.1 g of di-tertiary-butyl dicarbonate dissolved in 20 ml of toluene are slowly added to a stirred solution of 14.3 g of 4-piperidone ethylene ketal in 100 ml of toluene at 0° to 5°. The mixture is left to stir at room temperature for 2 hours and then evaporated under reduced pressure and distilled under reduced pressure. 22.2 g of the title compound are obtained, boiling point 83°–85° (0.2 Torr). TLC (ethyl acetate/hexane; 1:3): $R_f$=0.20.

b) (2R*, 1′R*)-1-tert-Butoxycarbonyl-2-1′-hydroxy-1′-phenyl-methyl)4-piperidone ethylene ketal (diastereomer A) and (2R*,1'S*)-1-tert-butoxycarbonyl-2-(1'-hydroxy-1'-phenyl-methyl)4-piperidone ethylene ketal (diastereomer B) 24.3 g (100 mmol) of 1-tert-butoxycarbonyl-4-piperidone ethylene ketal and 32.8 ml of tetramethylethylenediamine are dissolved in 100 ml of diethyl ether and cooled to −70°, and 87.5 ml (120 mmol) of a solution of secondary butyllithium (1.4 molar solution in cyclohexane/isopentane) are slowly added. The mixture is left to stir at −70° for 4 hours and then 12.72 g (120 mmol) of benzaldehyde are added all at once and the mixture is allowed to warm to 0°. Saturated ammonium chloride solution is added to the reaction mixture which is then extracted by shaking with ethyl acetate. The organic phase is separated off, washed with saturated sodium chloride solution, dried over sodium sulfate and evaporated under reduced pressure. Chromatography on silica gel with ethyl acetate as mobile phase yields 12.2 g of diastereomer A and 21.6 g of diastereomer B of the title compound. TLC (ethyl acetate/hexane; 1:1):

Diastereomer A (2R*,1'R*): $R_f$=0.43, melting point 133°–134°

Diastereomer B (2R*,1'S*): $R_f$=0.34, melting point 114°–116° c) 2-(1'-Hydroxy-1'-phenyl-methyl)-4-piperidone

A suspension of 2.6 g (7.44 mmol) of (2R*,1'R*)-1-tert-butoxycarbonyl-2-(1'-hydroxy-1'-phenyl-methyl)-4-piperidone ethylene ketal in 30 ml of 6N hydrochloric acid is heated at 60° for 1 hour and then cooled, neutralised with sodium carbonate and extracted by shaking with ethyl acetate. The organic phase is dried over sodium sulfate and evaporated under reduced pressure. The title compound of m.p. 124°–126° and $R_f$=0.26 (methylenechlorid/methanol/25% aqueous ammonia, 90:9.5:0.5) is thus obtained.

d) (2R*,1'R*)-1-(3,5-Dimethylbenzoyl)-2-(1'-hydroxy-1'-phenyl-methyl)-4-piperidone

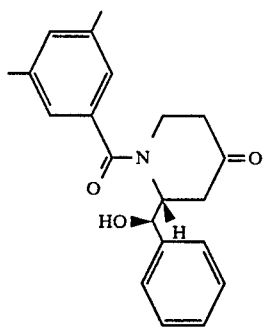

The crude 2-(1'-hydroxy-1'-phenyl-methyl)-4-piperidone obtained as described under c) hereinbefore is taken up in a mixture of 20 ml of dichloromethane and 20 ml of saturated sodium bicarbonate solution, cooled to 0°–5° with stirring and, over the course of 1.5 hours, 1.5 g (8.9 mmol) of 3,5-dimethylbenzoyl chloride are added dropwise. The mixture is left to stir for 1 hour, diluted with ethyl acetate, washed successively with 1N HCl and saturated sodium chloride solution, dried over sodium sulfate and evaporated to dryness under reduced pressure. The title compound can be purified by chromatography on silica gel with ethyl acetate/hexane (1:1) as mobile phase yields 1.71 g of the title compound. TLC (ethyl acetate/hexane; 1:1): $R_f$=0.19, FD-MS: M+ =338.

In an analogous manner as described hereinbefore under b), c) and d), also the following compounds can be prepared:

(2R*,1'R*)-1-(3,5-bistrifluoromethylbenzoyl)-2-{1'-hydroxy-1'-(4-chlorophenyl)methyl}-4-piperidone, TLC (ethyl acetate/hexane; 1:1): $R_f$=0.35; FD-MS: 479,481;

(2R*,1'R*)-1-(3,5-dimethylbenzoyl)-2-{1'-hydroxy-1'-(3,4-dichlorophenyl)methyl}-4-piperidone, TLC(ethyl acetate/hexan; 1:1): $R_f$=0.16, m.p. 222°–223°;

(2R*,1'S*)-1-(3,5-bistrifluoromethylbenzoyl)-2-{1'-hydroxy-1'-(4-chlorophenyl)methyl}-4-piperidone;

(2R*,1'R*)-1-(3,5-bistrifluoromethylbenzoyl)-2-{1'-hydroxy-1'-(3,4-dichlorophenyl)methyl}-4-piperidone;

(2R*, 1'R*)-1-(3,5-dimethylbenzoyl)-2-{1'-hydroxy-1'-(4-methoxyphenyl)methyl}-4-piperidone;

(2R*,1'S*)-1-(3,5-dimethylbenzoyl)-2-{1'-hydroxy-1'-(4-methoxyphenyl)methyl}-4-piperidone;

(2R*,1'R*)-1-(3,5-dimethylbenzoyl)-2-{1'-hydroxy-1'-(3-methoxyphenyl)methyl}-4-piperidone;

(2R*,1'S*)-1-(3,5-dimethylbenzoyl)-2-{1'-hydroxy-1'-(3-methoxyphenyl)methyl}-4-piperidone;

(2R*,1'R*)-1-(3,5-dimethylbenzoyl)-2-{1'-hydroxy-1'-(4-trifluormethylphenyl)methyl}-4-piperidone;

(2R*,1'S*)-1-(3,5-dimethylbenzoyl)-2-{1'-hydroxy-1'-(4-trifluoromethylphenyl)methyl}-4-piperidone;

(2R*,1'R*)-1-(3,5-dimethylbenzoyl)-2-{1'-hydroxy-1'-(4-chloro-3-trifluoromethylphenyl)methyl}-4-piperidone and (2R*,1'S*)-1-(3,5-dimethylbenzoyl)-2-{1'-hydroxy-1'-(4-chloro-3-trifluoromethylphenyl)-methyl}-4-piperidone.

EXAMPLE 86

(2R*,4S*,1'R*)-2-(1'-Hydroxy-1'-phenyl-methyl)1-(3,5-dimethylbenzoyl)-N-(4-quinolylmethyl)-4-piperidinamine (diastereomer A) and (2R*,4R*,1'R*)-1-(3,5-dimethylbenzoyl)-2-(1'-hydroxy-1'-phenyl-methyl)-N-(4-quinolylmethyl)-4-piperidinamine (diastereomer B)

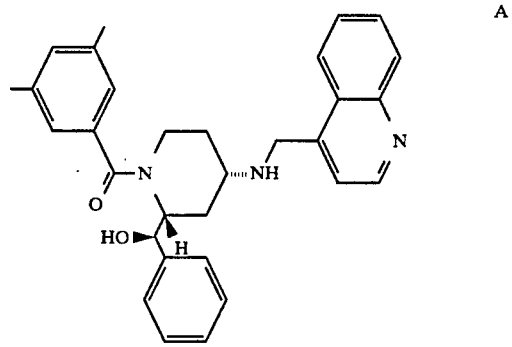

A

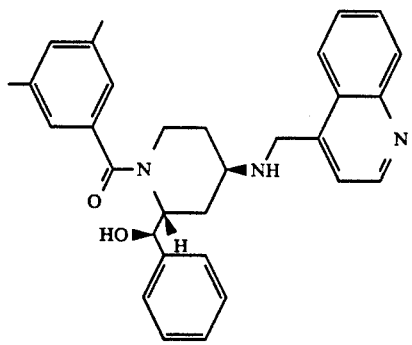

The title compound can be prepared in an analogous manner as described in Example 85 starting from 4-quinolinemethylamine. It is fractionated into the diastereomers and be purified by column chromatography on silica gel with ethyl acetate and ethyl acetate/methanol (50:1) as mobile phase. TLC (ethyl acetate):

Diastereomer A (2R*,4S*,1'R*): yield 180 mg; R$_f$=0.08, FD-MS: M+ =479

Diastereomer B (2R*,4R*,1'R*): yield 35 mg; R$_f$=0.01, FD-MS: M+ =479

EXAMPLE 87

(2R*,4S*,1'S*)-1-(3,5-Dimethylbenzoyl)-2-(1'-hydroxy-1'-phenyl-methyl)-N-(4-quinolylmethyl)4-piperidinamine (diastereomer A) and
(2R*,4R*,1'S*)-1-(3,5-dimethyl-benzoyl)-2-1'-hydroxy-1'-phenyl-methyl)-N-(4-quinolylmethyl)-4-piperidinamine (diastereomer B)

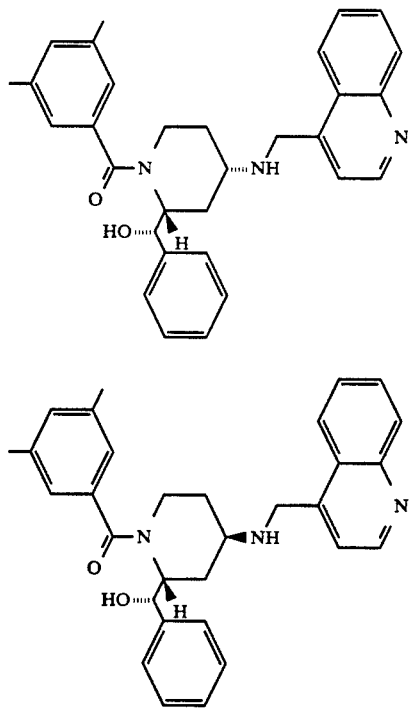

The title compound can be prepared in an analogous manner as described in Example 85 starting from 420 mg (1.24 mmol) of (2R*,1'S*)-1-(3,5-dimethylbenzoyl)-2-(1'-hydroxy-1'-phenyl-methyl)-4-quinolylmethylamine. It is fractionated into the diastereomers and be purified by column chromatography on silica gel with ethyl acetate and dichloromethane/methanol/35% strength ammonia solution (95:4.5:0.5) as mobile phase. TLC (ethyl acetate):

Diastereomer A (2R*,4S*,1'S*), yield 250 mg: R$_f$=0.08, FD-MS: M+ =479

Diastereomer B (2R*,4R*,1'S*), yield 170 mg: R$_f$=0.01, FD-MS: M+ =479

The starting material can be prepared, for example, as follows:

a) (2R*,1'S*)-1-(3,5-Dimethylbenzoyl)-2-(1'-hydroxy-1'-phenyl-methyl)-4-piperidone The title compound is prepared in an analogous manner as described in Example 1c from 860 mg (2.46 mmol) of (2R*,1'S*)-1-tert-butoxycarbonyl-2-(1'-hydroxy-1'-phenylmethyl)-4-piperidone ethylene ketal (Example 1b) and be prepared by column chromatography on silica gel with ethyl acetate/hexane (2:3) as mobile phase. Yield 400 mg; TLC (ethyl acetate/hexane; 1:1): R$_f$=0.24; FD-MS: M+ =337.

EXAMPLE 88

(2R*,4S*,1'R*)-2-{1'-Hydroxy-1'-(4-chlorophenyl)methyl}-1-(3,5-dimethylbenzoyl)-N-(4-quinolylmethyl)-4-piperidinamine (diastereomer A) and
(2R*,4R*,1'R*)-1-(3,5-dimethylbenzoyl)-2-{1'-hydroxy-1'-(4-chlorophenyl)methyl}-N-(4-quinolylmethyl)-4-piperidinamine (diastereomer B)

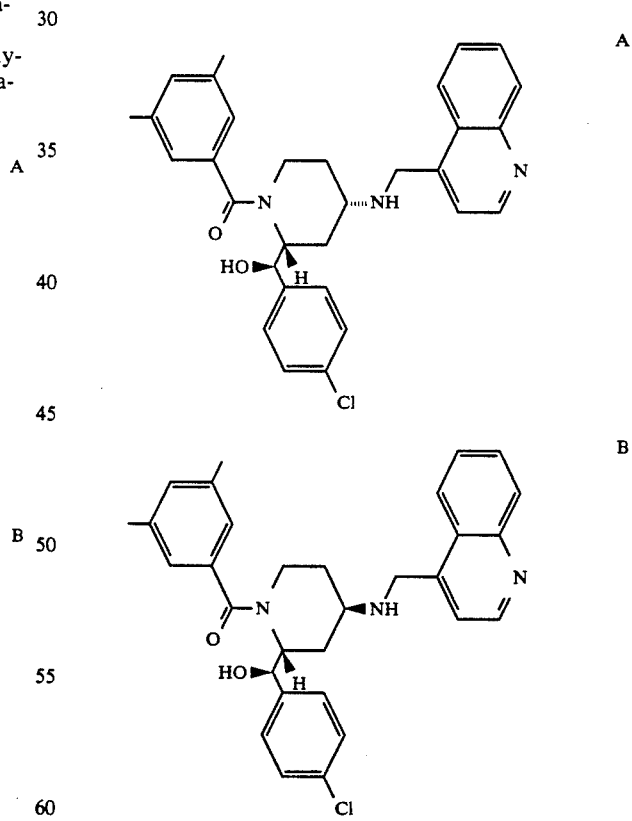

The title compound can be prepared in an analogous manner as described in Example 1 from 310 mg (0.833 mmol) of (2R*,1'R*)-1-(3,5-dimethylbenzoyl)2-{1'-hydroxy-1'-(4-chlorophenyl)methyl)4-piperidone and 145 mg (0.92 mmol) 4-quinolylmethylamine and be fractionated and purified by column chromatography on silica gel with ethyl acetate/isopropanol (95:5–90:10) as mobile phase. Diastereomer A: yield 225 mg. Diastereomer B: yield 80 mg. TLC (dichloromethane/methanol/25% strength ammonia solution (90:10:0.5)

Diastereomer A (2R*,4S*,1'R*): $R_f$=0.47, FD-MS: (M+1)+ =514

Diastereomer B (2R*,4R*,1'R*): $R_f$=0.35, FD-MS: M+ =513

The starting material can be prepared, for example, as follows:

a) (2R*,1'R*)-1-tert-Butoxycarbonyl-2-{1'-hydroxy-1'-(4-chlorophenyl)methyl}-4-piperidone ethylene ketal (diastereomer A) and (2R*,1'S*)-1-tert-butoxycarbonyl-2-{1'-hydroxy-1'-(4-chlorophenyl)methyl}-4-piperidone ethylene ketal (diastereomer B)

The title compound can be prepared in an analogous manner as described in Example 1b starting from 4-chlorobenzaldehyde, fractionated and purified by column chromatography on silica gel with ethyl acetate/hexane (1:3) as mobile phase, and be crystallised from ethyl acetate/hexane. TLC (ethyl acetate/hexane; 1:1):

Diastereomer A (2R*,1'R*): $R_f$=0.44, melting point 129°-130°

Diastereomer B (2R*,1'S*): $R_f$=0.35, melting point 160°-161° b) (2R*,1'R*)-1-(3;5-Dimethylbenzoyl)-2-{1'-hydroxy-1'(4-chlorophenyl)methyl}-4-piperidone The title compound can be prepared in an analogous manner as described in Example 1c and crystallises from ethyl acetate. Melting point 222°-225°; TLC (ethyl acetate/hexane; 1.1): $R_f$=0.17

EXAMPLE 89

(2R*,4S*,1'S*)-1-(3,5-Dimethylbenzoyl)-2-(1'-hydroxy-1'-(4-chlorophenyl)-methyl}-N-(4-quinolyl-methyl)-4-piperidinamine (diastereomer A) and (2R*,4R*,1'S*)-1-(3,5-dimethylbenzoyl)-2-{1'-hydroxy-1'-(4-chlorophenyl)methyl}-N-(4-quinolylmethyl)-4-piperidinamine (diastereomer B)

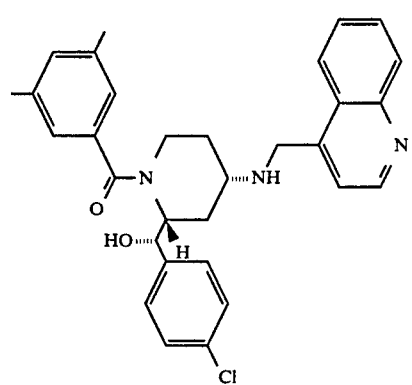

A

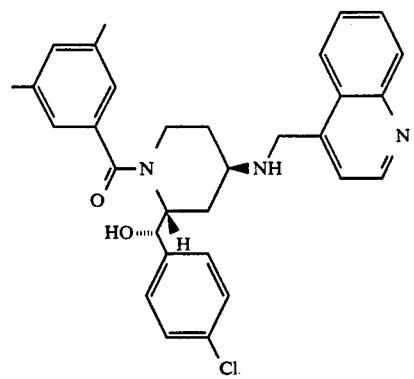

B

The title compound can be prepared in an analogous manner as described in Example 1 starting from (2R*,1'S*)-1-(3,5-dimethylbenzoyl)-2-{1'-hydroxy-1'-(4-chlorophenyl)methyl}-4-piperidone as starting material and be fractionated and purified by column chromatography on silica gel with dichloromethane/methanol/25% strength ammonia solution (95:4.5:0.5) as mobile phase. TLC (acetic acid):

Diastereomer A (2R*,4S*,1'S*): $R_f$=0.24, FD-MS: M+ =514

Diastereomer B (2R*,4R*,1'S*): $R_f$=0.06, FD-MS: M+ =514

The starting material can be prepared, for example, as follows:

a) (2R*,1'S*)1-(3,5-Dimethylbenzoyl)-2-{1'-hydroxy-1'-(4-chlorophenyl)methyl}-4-piperidone The title compound is prepared in an analogous manner as described in Example 1c starting from (2R*,1'S*)-1-tert-butoxycarbonyl-2-{1'-hydroxy-1'-(4-chlorophenyl)methyl}-4-piperidone ethylene ketal (Example 4a, diastereomer B). Melting point 195°-197°; TLC (ethyl acetate/hexane; 1:1): $R_f$=0.26

EXAMPLE 90

(2R*,4S*,1'S*)-1-(3,5-Dimethylbenzoyl)-2-{1'-hydroxy-1'-(3,4-dichlorophenyl)-methyl}-N-(4-quinolylmethyl)-4-piperidinamine (diastereomer A) and (2R*,4R*,1'S*)-1-(3,5-dimethylbenzoyl)-2-{1'-hydroxy-1'-(3,4-dichlorophenyl)methyl}-N-(4-quinolylmethyl)-4-piperidinamine (diastereomer B)

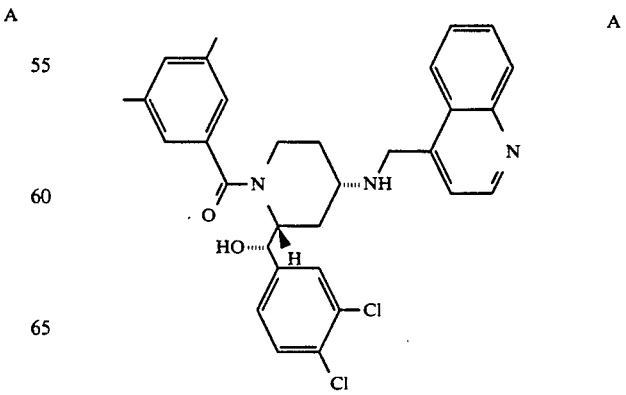

A

-continued

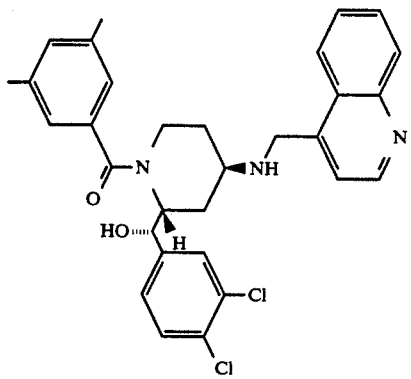

B

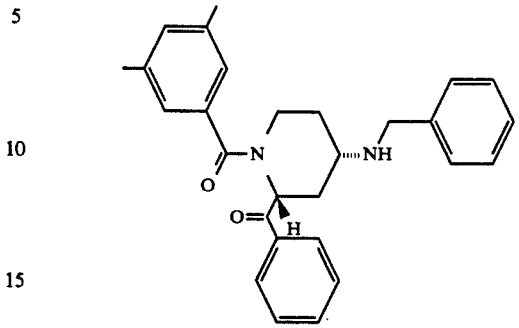

The title compound is prepared in an analogous manner as described in Example 1 starting from (2R*,1'S*)-1-(3,5-dimethylbenzoyl)-2-(1'-hydroxy-1'-(3,4-dichlorophenyl)methyl}-4-piperidone and fractionated by column chromatography on silica gel with dichloromethane/methanol/25% strength ammonia solution (93:6.5:0.5) as mobile phase. TLC (dichloromethane/methanol/25% strength ammonia solution; 90:9.5:0.5):

Diastereomer A (2R*,4S*,1'S*): $R_f$=0.38; melting point 138°-140°

Diastereomer B (2R*,4R*,1'S*): $R_f$=0.22; melting point 188°-190°

The starting material can be prepared, for example, as follows.

a) (2R*,1'R*)-1-tert-Butoxycarbonyl-2-{1'-hydroxy-1'-(3,4-dichlorophenyl)methyl}-4-piperidone ethylene ketal (diastereomer A) and (2R*,1'S*)-1-tert-butoxycarbonyl-2-{1'-hydroxy-1'-(3,4-dichlorophenyl)methyl}-4-piperidone ethylene ketal (diastereomer B)

The title compound is obtained in an analogous manner as described in Example 1b starting from 3,4-dichlorobenzaldehyde in place of benzaldehyde. The diastereomers are fractionated by column chromatography on silica gel with ethyl acetate/hexane (1:3) as mobile phase and crystallised from ethyl acetate/hexane. TLC (ethyl acetate/hexane; 1:1):

Diastereomer A (2R*,1'R*): $R_f$=0.57, IR spectrum ( CH2Cl2): 3700-3300, 1680 cm −1

Diastereomer B (2R*,1'S*): $R_f$=0.48, melting point 160°-162° b) (2R*,1'S*)-1-(3,5-Dimethylbenzoyl)-2-{1'-hydroxy-1'-(3,4-dichlorophenyl)methyl}-4-piperidone The title compound is prepared in an analogous manner as described in Example 1c from (2R*,1'S*)-1-tert-butoxycarbonyl-2-{1'-hydroxy-1'-(3,4-dichlorophenyl)-methyl}-4-piperidone ethylene ketal and crystallised from ethyl acetate/hexane; melting point 152°-152.5°; TLC (ethyl acetate/hexane; 1:1), $R_f$=0.24

EXAMPLE 91

(2R*,4S*)-N-Benzyl-1-(3,5-dimethylbenzoyl)-2-benzoyl-4-piperidinamine

A solution of 30 mg of (2R*,4R*,1'R*)-N-benzyl-N-trifluoroacetyl-1-(3,5-dimethylbenzoyl)-2-benzoyl-4-piperidinamine in 5 ml of methanol and 1 ml of 5N sodium hydroxide solution is heated at 60° for 10 minutes. It is allowed to cool to room temperature, diluted with 10% strength aqueous sodium bicarbonate solution and extracted by shaking twice with dichloromethane. The organic phases are combined, dried over sodium sulfate and evaporated to dryness under reduced pressure. The title compound of the formula is obtained by column chromatography on silica gel with ethyl acetate as mobile phase. TLC (ethyl acetate): $R_f$=0.17; IR spectrum (CH2Cl2): 1685, 1625, 1500 cm−1.

The starting material can be obtained, for example, as follows:

a) (2R*,4R*,1'R*)-N-Benzyl-N-trifluoroacetyl-1-(3,5-dimethylbenzoyl)-2-benzoyl-4-piperidinamine 0.167 ml of trifluoroacetic anhydride is added to a solution of 80 mg (0.19 mmol) of (2R*,4R*,1'R*)-N-benzyl-1-(3,5-dimethylbenzoyl)-2-(1'-hydroxy-1'-phenyl-methyl)-4-piperidinamine (Example 1, diastereomer B) in 1 ml pyridine at 0°, and the mixture is stirred at 0° for 2 hours. The reaction mixture is diluted with diethyl ether and water and separated into the phases. The organic phase is washed with 4N hydrochloric acid and saturated sodium chloride solution, dried over sodium sulfate and evaporated to dryness under reduced pressure. In order to remove doubly trifluoroacetylated by-products, the crude product is heated in 3 ml of ethanol and 0.5 ml of triethylamine at 55° and again evaporated under reduced pressure. The residue is taken up in 3 ml of dichloromethane containing 3Å molecular sieves, and 5 mg of tetrapropylammonium perruthenate and 100 mg of morpholine N-oxide are added. The mixture is left to stir for 16 hours, filtered, diluted with dichloromethane, washed successively with sodium bisulfate solution, saturated sodium chloride solution and 5% strength copper sulfate solution, dried over sodium sulfate, evaporated under reduced pressure and crystallised with diethyl ether/hexane; melting point 138°-139°; TLC (ethyl acetate/hexane; 1:1): $R_f$=0.71.

EXAMPLE 92

(2R*,4S*)-2-(4-Chlorobenzyl)-1-(3,5-dimethylbenzoyl)-N-(4-quinolinylmethyl)-4-piperidinamine A mixture of 550 mg (1.54 mmol) of (2R*,4S*)-2-(4-chlorobenzyl)-1-(3,5-dimethylbenzoyl)-4-piperidinamine and 242 mg (1.54 mmol) of 4-quinolinecarboxaldehyde are dissolved in 30 ml of toluene and evaporated to dryness under reduced pressure. This is repeated twice more. The residue is taken up in 10 ml of ethanol, 70 mg (1.85 mmol) of sodium boranate are added and the mixture is stirred at 25° for 3 hours. It is acidified with 1N hydrochloric acid and left to stir for 1 hour. The reaction mixture is poured into saturated aqueous sodium carbonate solution and extracted with ethyl acetate. The organic phase is washed with saturated sodium chloride solution, dried over sodium sulfate and evaporated to dryness under reduced pressure. The crude product is recrystallised twice from ethyl acetate and yields 320 mg of the title compound of the formula

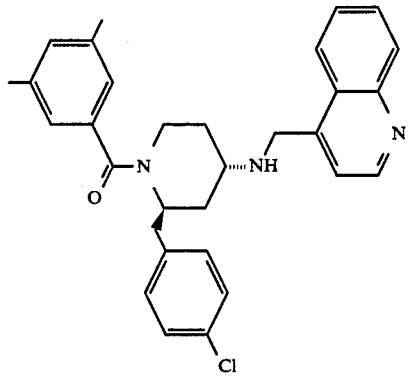

in the form of white crystals; melting point 148°-9°; MS: M+497.

The starting materials can be prepared, for example, as:

a) N-5-(4-Chlorophenyl)pent-1-en-4-yl-3.5-dimethylbenzamide 4.3 g (25.6 mmol) of 3,5-dimethylbenzoyl chloride are added over the course of 2 hours to a stirred solution of 5.0 g (25.6 mmol) of 2-{1-(4-chlorophenyl)}pent-4-enylamine and 5.33 ml (38.4 mol) of triethylamine in 100 ml of dichloromethane at 0°. The reaction mixture is stirred for a further 1 hour, 1N hydrochloric acid is added, and the mixture is extracted with dichloromethane. The organic phase is washed with saturated sodium chloride solution until neutral, dried over sodium sulfate and evaporated under reduced pressure. The crude product is crystallised from ethyl acetate/hexane and yields 7.36 g (88%) of white crystals; melting point 116°-118°; TLC (hexane/ethyl acetate; 3:1): $R_f=0.37$ b) N-{5-(4-Chlorophenyl)pent-1-en-4-yl}-N-ethoxymethyl-3,5-dimethylbenzamide 2.36 ml (25.2 mmol) of chloromethyl ethyl ether are added in small portions over the course of 2 hours to a vigorously stirred solution of 5.5 g (16.8 mmol) of N-{5-(4-chlorophenyl)pent-1-en-4-yl}-3.5-dimethylbenzamide and 100 mg of benzyltributylammonium chloride in 15 ml of 50% strength aqueous sodium hydroxide solution and 15 ml of dichloromethane at 0°-50°. The organic phase is taken up in dichloromethane and water, the organic phase is separated off, dried over sodium sulfate and evaporated to dryness under reduced pressure. The oily residue is purified by chromatography on silica gel with ethyl acetate/hexane (1:4) as mobile phase; TLC (ethyl acetate/hexane; 1:3): $R_f=0.50$;

1H-NMR (300 MHz, CDCl3): mixture of rotamers, δ=7.31-7.18 (m, 4H), 7.04-6.85 (m, 2.6H), 6.42 (br. s, 0.4H), 5.92-5.60 (m, 1H), 5.20-5.02 (m, 2H), 4.54-4.24 (m, 2H), 3.96-3.67 (m, 1H), 3.25-2.40 (m, 6H), 2.28 (s, ca 5H), 2.24 (s, ca 1H), 1.34-1.21 (m, ca 0.5H), 1.08 (t, J=7, ca 2.5 H).

c) (2R*,4S*)-2-(4-Chlorobenzyl)-1-(3,5-dimethylbenzoyl)-N-acetyl-4-piperidinamine 0.61 ml of tin tetrachloride and 0.24 ml of acetic anhydride are added successively to a solution of 1.0 g of N-{5-(4-chlorophenyl)pent-1-en-4-yl}-N-ethoxymethyl-3,5-dimethylbenzamide in acetonitrile cooled to −20°. The reaction mixture is then stirred at −20° for 2 hours and at 25° for 1 hour, poured into saturated aqueous sodium bicarbonate solution and extracted with ethyl acetate. The organic phase is separated off, dried over sodium sulfate and evaporated to dryness under reduced pressure. The crude title compound (orange oil) is purified by chromatography on silica gel with dichloromethane/methanol/25% strength ammonia solution (95:5:0.1) as mobile phase. TLC (dichloromethane/methanol/25% strength ammonia solution; 90:10:0.1): $R_f=0.45$; FD-MS: M+=398 d) (2R*,4S*)-2-(4-Chlorobenzyl)-1-(3,5-dimethylbenzoyl)-4-piperidinamine

A suspension of 730 mg (1.83 mmol) of (2R*,4S*)-2-(4-chlorobenzyl)-1-(3,5-dimethylbenzoyl)-N-acetyl-4-piperidinamine in 6N hydrochloric acid is heated at 100° for 16 hours, during which the starting material dissolves. The reaction mixture is basified with 10% strength aqueous sodium carbonate solution and extracted with ethyl acetate. The combined organic phases are dried over sodium sulfate and evaporated to dryness under reduced pressure. The crude title compound is purified by chromatography on silica gel with dichloromethane/methanol/25% strength ammonia solution (90:10:0.1) as mobile phase and is obtained as almost colourless resin. TLC (dichloromethane/methanol/25% strength ammonia solution; 90:10:0.1): $R_f=0.26$; FD-MS: (M+1)+=357

EXAMPLE 93

(2R*,4S*)-2-(3,4-Dichlorobenzyl)-1-(3,5-dimethylbenzoyl)-N-(4-quinolylmethyl)-4-piperidinamine The title compound of the formula

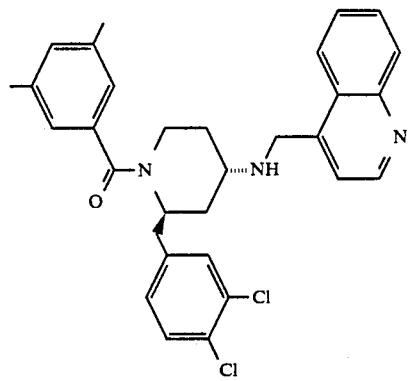

can be prepared in an analogous manner as in Example 8 starting from (2R*,4S*)-2-(3,4-dichlorobenzyl)-1-(3,5-dimethylbenzoyl)-4-piperidinamine as starting material: melting point 121°-124°; TLC (dichloromethane/methanol/25% strength ammonia solution; 90:9.5:0.5): $R_f=0.30$; FD-MS: M+=531/533

The starting material can be prepared as follows:

a) N-{5-(3,4-Dichlorophenyl)pent-1-ene-4-yl}-3,5-dimethylbenzamide

The title compound is obtained in 93% yield in an analogous manner as described in Example 8a; melting point 155°-157°; IR spectrum (KBr): 3230, 1625, 1595 cm-1; TLC (hexane/ethyl acetate; 2:1): $R_f=0.46$ b) N-{5-(3,4-Dichlorophenyl)pent-1-ene-4-yl}-N-ethoxymethyl-3,5-dimethylbenzamide The title compound is obtained in an analogous manner as described in Example 8b; IR spectrum (film):

1640, 1600 cm-1;) TLC (hexane/ethyl acetate; 2:1): R/=0.58 c) (2R*,4S*)-N-Acetyl-2-(3,4-dichlorobenzyl)-1-(3,5-dimethylbenzoyl)-4-piperidinamine The title compound is obtained in an analogous manner as described in Example 8c; IR spectrum (KBr): 3260, 1655, 1605, 1595, 1540 cm-1 (KBr); TLC (dichloromethane/methanol; 10:1); R/=0.32 d) (2R*,4S*)-2-(3,4-Dichlorobenzyl)-1-(3,5-dimethylbenzoyl)-4-piperidinamine

The title compound is obtained in an analogous manner as described in Example 8d; TLC (dichloromethane/methanol/25% strength ammonia solution; 300:25:3): R/=0.46

EXAMPLE 94

(2R*,4S*)-1-(3,5-Dimethylbenzoyl)-2-phenyl-N-(4-quinolylmethyl)-4-piperidinamine A suspension of 211 mg (0.60 mmol) of (2R*,4S*)-N-acetyl-1-(3,5-dimethylbenzoyl)-2-phenyl-4-piperidinamine in 8 ml of 6N hydrochloric acid is heated at 100°) under inert gas for 16 hours, during which the starting material dissolves completely. The mixture is allowed to cool to room temperature, and is neutralised with sodium carbonate solution and extracted with ethyl acetate. Column chromatography on silica gel with dichloromethane/methanol (95:5 to 90:10) as mobile phase yields 135 mg of amine which, without further purification, is reacted further with 60 mg (0.38 mmol) of quinoline-4-carboxaldehyde in toluene with azeotropic removal of water. An oil remains after the solvent has been stripped off. This oil is taken up in ethanol and, at 0°, 14 mg (0.38 mmol) of sodium borohydride are added. After 1.5 hours, the reaction mixture is treated with 1N hydrochloric acid, stirred at 250°for 1 hour and finally neutralised with 10% strength aqueous sodium carbonate solution. It is extracted by shaking with ethyl acetate, and the organic phase is separated off, dried over sodium sulfate and evaporated to dryness under reduced pressure. The title compound of the formula

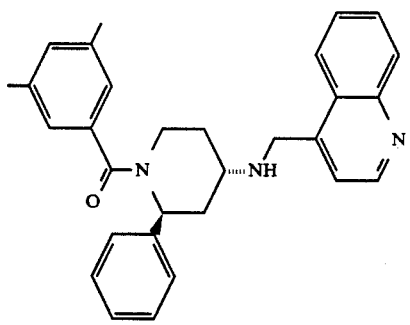

is isolated by column chromatography on silica gel with dichloromethane/isopropanol (9:1) as mobile phase; TLC (dichloromethane/isopropanol; 9:1): R/=0.51; FD-MS: M+ =449

The starting material can be prepared as follows:

a) (2R*,4S*)-N-Acetyl-1-benzyloxycarbonyl-2-phenyl-4-piperidinamine 1.41 ml (12.0 mmol) of tin tetrachloride are added to a solution of 2.03 g (9.90 mmol) of N-but-3-en-1-yl-O-benzylcarboxamide and 1.14 g (10.7 mmol) of benzaldehyde in 1 ml (810.6 mmol) of acetic anhydride and 20 ml of acetonitrile at −20°. The mixture is kept at −20 for 16 hours, then treated with 10% strength aqueous sodium bicarbonate solution and extracted with ethyl acetate. The organic phase is dried over sodium sulfate and evaporated to dryness under reduced pressure. The crude title compound is crystallised from ethyl acetate/hexane; melting point 139°-140°; CI-MS: (M+H)+ =353, (M+NH4)+ =370.

b) (2R*,4S*)-N-Acetyl-1-(3,5-dimethylbenzoyl)-2-phenyl-4-piperidinamine

A solution of 496 mg (1.41 mmol) of (2R*,4S*)-N-acetyl-1-benzyloxycarbonyl-2-phenyl-4-piperidinamine in 30 ml of ethanol and 8 ml of 1N hydrochloric acid is mixed with 50 mg of 10% Pd/C catalyst and stirred under a hydrogen atmosphere until no more hydrogen is taken up. The catalyst is removed by filtration through diatomaceous earth, and the filtrate is evaporated to dryness under reduced pressure. The residue is taken up in 5 ml of dichloromethane and 5 ml of 10% strength aqueous sodium bicarbonate solution and, while stirring at 0°, 285 mg (1.69 mmol) of 3,5-dimethylbenzoyl chloride are added slowly over the course of 1 hour. The reaction mixture is extracted with dichloromethane. The organic phase is separated off, dried over sodium sulfate and evaporated to dryness under reduced pressure. The title compound crystallises from ethyl acetate; melting point 201°-203°; CI-MS: (M+H)+ =351.

EXAMPLE 95

(2R*,4S*)-1-(3,5-Dichlorobenzoyl)-2-phenyl-N-(4-quinolinmmthyl)-4-piperidinamine The title compound of the formula

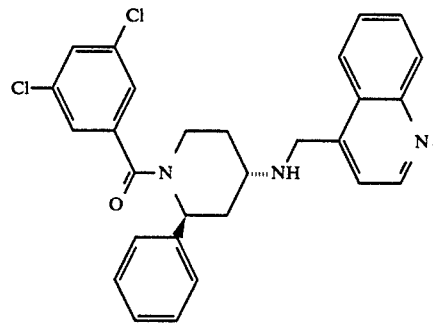

can be obtained in an analogous manner as described in Example 10; TLC (dichloromethane/methanol/25% strength ammonia solution; 90:9.5:0:5): R/=0.46; FD-MS: M+ =489.

The starting material can be prepared as follows:

a) (2R*,4S*)-N-Acetyl-1-(3,5-dichlorobenzoyl)-2-phenyl-4-piperidinamine

The title compound is obtained in an analogous manner as in Example 10b starting from 3,5-dichlorobenzoyl chloride; melting point 161°-163°; TLC (dichloromethane/methanol/25% strength ammonia solution; 90:9.5:0:5): R/=0.55.

EXAMPLE 96

(2R*,4S*)-1-(1-Naphthoyl)-2-phenyl-N-(4-quinolylmethyl)-4-piperidineamine

The title compound of the formula

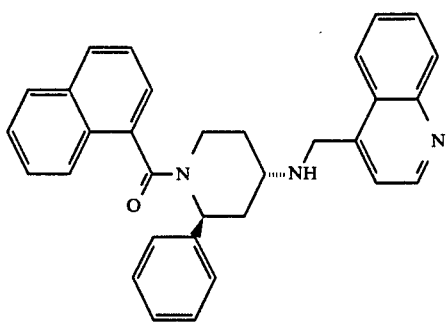

is obtained in an analogous example as described in Example 11; TLC (dichloromethane/methanol/25% strength ammonia solution, 90:9.5:0:5): $R_f$=0.41; FD-MS: M+ =471

The starting material is obtained as follows:

a) (2R*,4S*)-N-Acetyl-1-(l-naphthoyl)-2-phenyl-4-piperidinamine

The title compound is obtained in an analogous manner as described in Example 10b; TLC (dichloromethane/methanol/25% strength ammonia solution, 90:9.5:0:5): $R_f$=0.42.

EXAMPLE 97

(2R*,4S*)-1-(3,5-Dimethylbenzoyl)-2-(l-naphthyl)-N-(4-quinolylmethyl)-4-piperidinamine The title compound of the formula

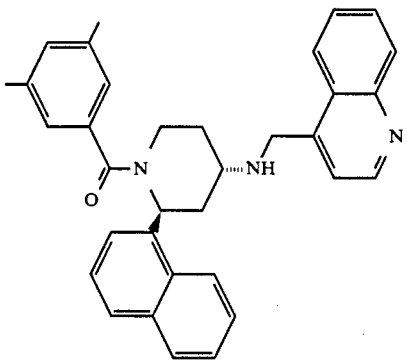

is obtained in an analogous manner as described in Example 10; TLC (dichloromethane/methanol25% strength ammonia solution, 90:9.5:0:5): $R_f$=0.50 FD-MS: M+ =499

The starting material is obtained as follows:

a) (2R*,4S*)-N-Acetyl-1-benzyloxycarbonyl-2-(l-naphthyl)-4-piperidinamine

The title compound is obtained in an analogous manner as described in Example 10a starting from naphthalene-1-carboxaldehyde in place of benzaldehyde; (dichloromethane/methanol/25% strength ammonia solution, 90:9.5:0:5): $R_f$=0.31 FD-MS: M+ =402.

b) (2R*,4S*)-(N)-Acetyl-1-(3,5-dimethylbenzoyl)-2-(l-naphthyl)-4-piperidinamine

The title compound is obtained in an analogous manner as described in Example 10b; TLC (dichloromethane/methanol/25% strength ammonia solution, 90:9.5:0:5): $R_f$=0.26 FD-MS: M+ =400.

EXAMPLE 98

The following compounds can also be prepared in an analogous manner as described in Examples 85 to 97:

(2R*,4S*)-1-(3,5-dimethylbenzoyl)-2-(2-naphthyl)-N-(4-quinolinylmethyl)-4-piperidinamine;

(2R*,4S*)-1-(3,5-dimethylbenzoyl)-2-(4-methoxyphenylmethyl)-N-(4-quinolinylmethyl)-4-piperidinamine;

(2R*,4S*)-1-(3,5-dimethylbenzoyl)-2-(3-methoxyphenylmethyl)-N-(4-quinolinylmethyl)-4-piperidinamine;

(2R*,4S*)-1-(3,5-dimethylbenzoyl)-2-(4-nitrobenzyl)-N-(4-quinolinylmethyl)-4-piperidinamine;

(2R*,4S*)-1-(3,5-dimethylbenzoyl)-2-(4-trifluoromethylphenylmethyl)-N-(4-quinolinylmethyl)-4-piperidinamine;

(2R*,4S*)-1-(3,5-dimethylbenzoyl)-2-(2,4-dichlorophenylmethyl)-N-(4-quinolinylmethyl)-4-piperidinamine;

(2R*,4S*)-1-(3,5-dimethylbenzoyl)-2-(2-phenylethyl)-N-(4-quinolinylmethyl)-4-piperidinamine;

(2R*,4S*)-1-(3,5-dimethylbenzoyl)-2-(2-phenylethenyl)-N-(4-quinolinylmethyl)-4-piperidinamine;

(2R*,4S*)-1-(3,5-dimethylbenzoyl)-2-benzoyl-N-(4-quinolinylmethyl)-4-piperidinamine;

(2R*,4S*)-1-(3,5-dimethylbenzoyl)-2-(4-chlorobenzoyl)-N-(4-quinolinylmethyl)-4-piperidinamine;

(2R*,4S*)-1-(3,5-dimethylbenzoyl)-2-(2-naphthyl)-N-(4-quinolinylmethyl)-4-piperidinamine;

(2R*,4S*)-1-(3,5-dimethylbenzoyl)-2-(4-methoxybenzyl)-N-(4-quinolinylmethyl)-4-piperidinamine;

(2R*,4S*)-1-(3,5-dimethylbenzoyl)-2-(3-methoxybenzyl)-(4-quinolinylmethyl)-4-piperidinamine;

(2R*,4S*)-1-(3,5-dimethylbenzoyl)-2-(4-nitrobenzyl)-(4-quinolinylmethyl)-4-piperidinamine;

(2R*,4S*)-1-(3,5-dimethylbenzoyl)-2-(4-trifluoromethylbenzyl)-(4-quinolinylmethyl)-4-piperidinamine;

(2R*,4S*)-1-(3,5-dimethylbenzoyl)-2-(2,4-dichlorobenzyl)-(4-quinolinylmethyl)-4-piperidinamine;

(2R*,4S*)-1-(3,5-dimethylbenzoyl)-2-(2-phenylethyl)-(4-quinolinylmethyl)-4-piperidinamine;

(2R*,4S*)-1-(3,5-dimethylbenzoyl)-2-(2-phenylethenyl)-N-(4-quinolinylmethyl)-4-piperidinamine;

(2R*,4S*)-1-(3,5-dimethylbenzoyl)-2-(benzoylmethyl)-N-(4-quinolinylmethyl)-4-piperidinamine;

(2R*,4S*)-1-(3,5-dimethylbenzoyl)-2-(4-chlorobenzoylmethyl)-N-(4-quinolinylmethyl)-4-piperidinamine.

EXAMPLE 99

Tables each containing 50 mg of (2R,4S)-2-benzyl-1-(3,5-dimethylbenzoyl)-N-(2-phenethyl)-4-piperidinamine or a salt, for example the hydrochloride, thereof can be prepared as follows:

| Composition (10,000 tablets) | |
|---|---|
| Active substance | 500.0 g |
| Lactose | 500.0 g |
| Potato starch | 352.0 g |
| Gelatin | 8.0 g |
| Talc | 60.0 g |
| Magnesium stearate | 10.0 g |
| Silicon dioxide (highly disperse) | 20.0 g |
| Ethanol | q.s. |

The active substance is mixed with the lactose and 292 g of potato starch, the mixture is moistened with an ethanolic solution of the gelatin and granulated through a screen. After drying, the remainder of the potato starch, the magnesium stearate, the talc and the silicon dioxide are mixed in, and the mixture is compressed to tablets each weighing 145.0 mg and containing 50.0 mg of active substance, which can, if required, be provided with dividing grooves for more accurate adaptation of the dosage.

EXAMPLE 100

Lacquered tablets each containing 100 mg of (2R,4S)-2-benzyl-1-(3,5-dimethylbenzoyl)-N-(2-phenethyl)4-piperidinamine or a salt, for example hydrochloride, thereof can be prepared as follows:

| Composition (for 1000 lacquered tablets) | |
|---|---|
| Active substance | 100.0 g |
| Lactose | 100.0 g |
| Maize starch | 70.0 g |
| Talc | 8.5 g |
| Calcium stearate | 1.5 g |
| Hydroxypropylmethylcellulose | 2.36 g |
| Shellac | 0.64 g |
| Water | q.s. |
| Methylene chloride | q.s. |

The active substance, the lactose and 40 g of the maize starch are mixed and moistened with a paste prepared from 15 g of maize starch and water (with heating) and granulated. The granules are dried, the remainder of the maize starch, the talc and the calcium stearate are added and mixed with the granules. The mixture is compressed to tablets (weight: 280 mg) and these are lacquered with a solution of hydroxypropylmethylcellulose and of shellac in methylene chloride; final weight of the lacquered tablet: 283 mg.

EXAMPLE 101

Gelatin two-piece capsules containing 100 mg of active substance, for example (2R,4S)-2-benzyl-1-(3,5-dimethylbenzoyl)-N-(2-phenethyl)-4-piperidinamine or a salt, for example the hydrochloride, thereof can be prepared, for example, as follows:

| Composition (for 1000 capsules) | |
|---|---|
| Active substance | 100.0 g |
| Lactose | 250.0 g |
| Microcrystalline cellulose | 30.0 g |
| Sodium lauryl sulfate | 2.0 g |
| Magnesium stearate | 8.0 g |

The sodium lauryl sulfate is screened in through a screen with a mesh width of 0.2 mm into the lyophilised active substance. The two components are intimately mixed. Then first the lactose is screened in through a screen with a mesh width of 0.6 mm and then the microcrystalline cellulose is screened in through a screen with a mesh width of 0.9 Mm. This is followed by renewed intimate mixing for 10 minutes. Finally, the magnesium stearate is screened in through a screen with a mesh width of 0.8 mm. After mixing for a further 3 minutes, the resulting formulation is packed in 390 mg portions into size 0 gelatin two-piece capsules.

EXAMPLE 102

It is also possible to prepare pharmaceutical products containing another compound of the formula 1 according to one of the preceding preparation examples in an analogous manner as described in previous Examples 99 to 101.

We claim:

1. A 1-acylpiperidine compound of the formula I

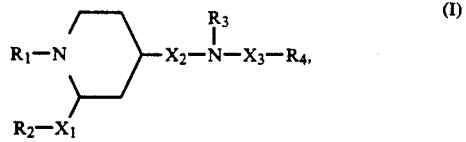

wherein $R_1$ is a benzoyl, naphthoyl or fluorenoyl radical, each of which is unsubstituted or substituted by lower alkyl, lower alkoxy, hydroxyl, di-lower-alkylamino, halogen, cyano and/or trifluoromethyl, $R_2$ is a phenyl or naphtyl radical, each of which is unsubstituted or substituted by lower alkyl, lower alkoxy, halogen and/or trifluoromethyl, $R_3$ is hydrogen, lower alkyl, carbamoyl, lower alkanoyl, carboxy-lower-alkanoyl or carboxy-lower-alkenoyl, lower alkoxycarbonyl-lower-alkyl, carbamoyl-lower-alkanoyl, N-mono- or N,N-di-lower-alkylcarbamoyl-lower-alkanoyl, N-cyclalkylcarbamoyl-lower-alkanoyl or N-phenylcarbamoyl-lower-alkanoyl, $R_4$ is a quinolinyl radical which is unsubstituted or C-substituted by lower alkyl, lower alkoxy, halogen and/or trifluoromethyl and optionally N-substituted by lower alkanoyl, $X_1$ is methylene or ethylene, $X_2$ is a direct linkage, and $X_3$ is a lower alkylene radical, or a salt thereof.

2. A compound according to claim 1 of the formula I in which $R_1$ is benzoyl which is unsubstituted or substituted by lower alkyl or lower alkoxy, or $R_1$ is naphthoyl which is unsubstituted or substituted by lower alkyl, lower alkoxy, di-lower-alkylamino, halogen and/or trifluoromethyl, $R_2$ is a phenyl or naphthyl radical, each of which is unsubstituted or substituted by $C_1$–$C_4$alkyl, $C_1$–$C_4$alkoxy, halogen and/or trifluoromethyl, $R_3$ is hydrogen, $C_1$–$C_7$alkyl, carbamoyl, $C_2$–$C_7$alkanoyl, carboxy-$C_1$–$C_4$alkanoyl or carboxy-$C_2$–$C_4$alkenoyl, $R_4$ is quinolyl, $X_1$ is methylene, $X_2$ is a direct linkage, and $X_3$ is $C_1$–$C_4$alkylene, or a salt thereof.

3. A compound according to claim 1 of the formula I in which $R_1$ is benzoyl or naphthoyl which is unsubstituted or substituted by $C_1$–$C_4$alkyl, $C_1$–$C_4$alkoxy, halogen and/or trifluoromethyl, $R_2$ is a phenyl or naphthyl radical, each of which is unsubstituted or substituted by $C_1$–$C_4$alkyl, $C_1$–$C_4$alkoxy, halogen and/or trifluoromethyl, $R_3$ is hydrogen, $C_1$–$C_7$alkyl, carbamoyl, $C_2$–$C_7$alkanoyl, carboxy-$C_1$–$C_4$alkanoyl or carboxy-$C_3$–$C_5$alkenoyl, $R_4$ is quinolyl, $X_1$ is methylene, $X_2$ is a direct linkage, and $X_3$ is $C_1$–$C_4$alkylene, or a salt thereof.

4. A compound according to claim 1 of the formula I in which $R_1$ is benzoyl which is unsubstituted or mono- or disubstituted by $C_1$–$C_4$alkyl, $C_1$–$C_4$alkoxy, halogen of atomic number up to and including 35 and/or trifluoromethyl, or unsubstituted naphthoyl, $R_2$ is phenyl or phenyl mono- oder disubstituted by halogen of atomic number up to and including 35 and/or trifluoromethyl, $R_3$ is hydrogen, $R_4$ is unsubstituted quinolinyl, $X_1$ is methylene, $X_2$ is a direct linkage and $X_3$ is $C_1C_4$alkylene, or a salt thereof.

5. A compound claimed in claim 1 being (2R*,4S*)-2-benzyl-1-(3,5-bis-(-trifluoromethyl)-benzoyl)-N-(4-quinolylmethyl)-4-piperidinamine or a salt thereof.

6. A compound claimed in claim 1 being (2R,4S)- or (2R,4R)2-benzyl-1-(3,5-dimethylbenzoyl)-N-(4-quinolylmethyl)-4-piperidinamine or a salt thereof.

7. A compound as claimed in claim 1 selected from
(2R*,4S*)-2-benzyl-1-(2-naphthoyl)-N-(4-quinolylmethyl)-4-piperidinamine;
   (2R*,4S*)-2-benzyl-1-(3-trifluoromethylbenzoyl)-N-(4-quinolylmethyl)-4-piperidinamine;
   (2R*,4S*)-2-benzyl-1-(3,5-bis-(trifluoromethyl)-benzoyl)-N-(4-quinolylmethyl)-4-piperidinamine;
   (2R*,4S*)-2-benzyl-1-(3,5-dimethoxybenzoyl)-N-(4-quinolylmethyl)-4-piperidinamine;
   (2R*,4S*)-2-benzyl-1-(1-naphthoyl)-N-(4-quinolylmethyl)-4-piperidinamine;
   (2R*,4S*)-2-benzyl-1-(3,5-dichlorobenzoyl)-N-(4-quinolylmethyl)-4-piperidinamine;
   (2R*,4S*)-2-benzyl-1-(3-methoxybenzoyl)-N-(4-quinolylmethyl)-4-piperidinamine;
   (2R*,4S*)-2-benzyl-1-(3-N,N-dimethylaminobenzoyl)-N-(4-quinolylmethyl)-4-piperidinamine;
   (2R*,4S*)-2-benzyl-1-benzoyl-N-(4-quinolylmethyl)-4-piperidinamine;
   (2R*,4S*)-2-benzyl-1-(3-chlorobenzoyl)-N-(4-quinolylmethyl)-4-piperidinamine;
   (2R*,4S*)-2-benzyl-1-(3,5-dichlorobenzoyl)-N-(4-quinolylmethyl)-N-(3-carboxamido-propionyl)-4-piperidinamine;
   (2R,4S)-2-benzyl-1-(3,5-bis-(trifluoromethyl)-benzoyl)-N-(4-quinolylmethyl)-4-piperidinamine;
   (2R,4S)-2-benzyl-1-(3,5-dichlorobenzoyl)-N-(4-quinolylmethyl)-4-piperidinamine;
   (2R*,4S*)-2-benzyl-1-(2,4-dichlorobenzoyl)-N-(4-quinolylmethyl)-4-piperidinamine;
   (2R*,4S*)-2-benzyl-1-(2,6-dichlorobenzoyl)-N-(4-quinolylmethyl)-4-piperidinamine;
   (2R*,4S*)-2-benzyl-1-(3,5-dibromobenzoyl)-N-(4-quinolylmethyl)-4-piperidinamine;
   (2R*,4S*)-2-benzyl-1-(9-fluorenoyl)-N-(4-quinolylmethyl)-4-piperidinamine;
   (2R*,4S*)-2-benzyl-1-(3-toluoyl)-N-(4-quinolylmethyl)-4-piperidinamine;
   (2R*,4S*)-2-benzyl-1-(3-bromobenzoyl)-N-(4-quinolylmethyl)-4-piperidinamine;
   (2R*,4S*)-2-benzyl-1-(3,5-dihydroxybenzoyl)-N-(4-quinolylmethyl)-4-piperidinamine;
   (2R*,4S*)-2-benzyl-1-(3-cyanobenzoyl)-N-(4-quinolylmethyl)-4-piperidinamine;
   (2R*,4S*)-2-benzyl-1-(2-chlorobenzoyl)-N-(4-quinolylmethyl)-4-piperidinamine;
   (2R*,4S*)-2-benzyl-1-(4-chlorobenzoyl)-N-(4-quinolylmethyl)-4-piperidinamine;
   (2R*,4S*)-2-benzyl-1-(3,5-dichlorobenzoyl)-N-(4-quinolylmethyl)-N-methyl-4-piperidinamine;
   (2R*,4S*)-2-benzyl-1-(3,5-dichlorobenzoyl)-N-(4-quinolylmethyl)-N-cyclohexylcarbamoyl-4-piperidinamine;
   (2R*,4S*)-2-benzyl-1-(3,5-dichlorobenzoyl)-N-(4-quinolylmethyl)-N-phenylcarbamoyl-4-piperidinamine;
   (2R*,4S*)-2-benzyl-1-(4-methoxybenzoyl)-N-(4-quinolylmethyl)-4-piperidinamine;
   (2R,4S)- or (2R,4R)2-benzyl-1-(3,5-dimethylbenzoyl)-N-(4-quinolylmethyl)-4-piperidinamine;
   (2R,4S)-2-benzyl-1-(3,5-dimethylbenzoyl)-N-(3-quinolylmethyl)-4-piperidinamine;
   (2R,4S)-2-benzyl-1-(3,5-dimethylbenzoyl)-N-(2-quinolylmethyl)-4-piperidinamine-dihydrochloride;
   (2R,4S) or (2S,4S)-2-benzyl-1-(3,5-dimethylbenzoyl)-N-(4-quinolylmethyl)-4-piperidinamine;
   (2R*,4S*)-2-(4-chlorobenzyl)-1-(3,5-dichlorobenzoyl)-N-(4-quinolylmethyl)-4-piperidinamine; and
   (2R*,4S*)-2-(3,4-dichlorobenzyl)-1-(3,5-dimethylbenzoyl)-N-(4-chinolinmethyl)-4-piperidinamine; or, in each case, a pharmaceutically acceptable salt thereof.

8. A pharmaceutical composition comprising a compound of formula I according to claim 2 in free form or in pharmaceutically acceptable salt form and a pharmaceutic carrier.

9. A method for the treatment of conditions responsive to substance P antagonism in warm-blooded animals comprising administering to that animal a therapeutically effective amount of a compound of formula I according to claim 2 or a pharmaceutically acceptable salt thereof.

10. A compound as claimed in claim 2 selected from
   (2R,4S)-2-benzyl-1-(3,5-dimethylbenzoyl)-N-(quinolin-2-ylmethyl)-4-piperidinamine;
   (2R,4S)-2-benzyl-1-(3,5-dimethylbenzoyl)-N-(quinolin-3-ylmethyl)-4-piperidinamine;
   (2S,4S)-2-benzyl-1-(3,5-dimethylbenzoyl)-N-(quinolin-2-ylmethyl)-4-piperidinamine;
   (2R,4S)-2-benzyl-1-(3,5-ditrifluoromethylbenzoyl)-N-(quinolin-2-ylmethyl)-4-piperidinamine;
   (2R,4S)-2-benzyl-1-(3,5-ditrifluoromethylbenzoyl)-N-(quinolin-3-ylmethyl)-4-piperidinamine;
   (2S,4S)-2-benzyl-1-(3,5-ditrifluoromethylbenzoyl)-N-(quinolin-2-ylmethyl)-4-piperidinamine;
   (2R,4S)-2-benzyl-1-(3,5-dichlorobenzoyl)-N-(quinolin-2-ylmethyl)-4-piperidinamine;
   (2S,4S)-2-benzyl-1-(3,5-dichlorobenzoyl)-N-(quinolin-2-ylmethyl)-4-piperidinamine;
   (2R,4S)-2-benzyl-1-(3,5-dichlorobenzoyl)-N-(quinolin-3-ylmethyl)-4-piperidinamine;
   (2S,4S)-2-benzyl-1-(3,5-dichlorobenzoyl)-N-(quinolin-3-ylmethyl)-4-piperidinamine;
   (2R,4S)-2-benzyl-1-(3,5-dimethoxybenzoyl)-N-(quinolin-2-ylmethyl)-4-piperidinamine;
   (2S,4S)-2-benzyl-1-(3,5-dimethoxybenzoyl)-N-(quinolin-2-ylmethyl)-4-piperidinamine;
   (2R,4S)-2-benzyl-1-(3,5-dimethoxybenzoyl)-N-(quinolin-3-ylmethyl)-4-piperidinamine;
   (2S,4S)-2-benzyl-1-(3,5-dimethoxybenzoyl)-N-(quinolin-2-ylmethyl)-4-piperidinamine;
   (2R*,4S*)-1-(3,5-dimethylbenzoyl)-2-(4-nitrobenzoyl)-N-(4-quinolinylmethyl)-4-piperidinamine;
   (2R*,4S*)-1-(3,5-dimethylbenzoyl)-2-(2-phenylethyl)-N-(4-quinolinylmethyl)-4-piperidinamine;
   (2R*,4S*)-1-(3,5-dimethylbenzoyl)-2-(2-phenylethenyl)-N-(4-quinolinylmethyl)-4-piperidinamine;
   (2R*,4S*)-1-(3,5-dimethylbenzoyl)-2-(4-methoxybenzyl)-N-(4-quinolinylmethyl)-4-piperidinamine;
   (2R*,4S*)-1-(3,5-dimethylbenzoyl)-2-(3-methoxybenzyl)-(4-quinolinylmethyl)-4-piperidinamine;
   (2R*,4S*)-1-(3,5-dimethylbenzoyl)-2-(4-trifluoromethylbenzyl)-(4-quinolinylmethyl)-4-piperidinamine;
   (2R*,4S*)-1-(3,5-dimethylbenzoyl)-2-(2,4-dichlorobenzyl)-(4-quinolinylmethyl)-4-piperidinamine; and
   (2R*,4S*)-1-(3,5-dimethylbenzoyl)-2-(2-phenylethyl)-(4-quinolinylmethyl)-4-piperidinamine; or, in each case, a pharmaceutically acceptable salt thereof.

* * * * *

UNITED STATES PATENT AND TRADEMARK OFFICE
CERTIFICATE OF CORRECTION

PATENT NO. : 5,310,743

DATED : May 10, 1994

INVENTOR(S) : Walter Schilling, Silvio Ofner and Siem J. Veenstra

It is certified that error appears in the above-indentified patent and that said Letters Patent is hereby corrected as shown below:

Column 104,

In claim 8, line 2 after "claim" delete "2" and insert --1-- in lieu thereof, and in line 3 after "and a " delete "pharmaceutic" and insert --pharmaceutical-- in lieu thereof.

In claim 9, line 5 after "claim" delete "2" and insert --1-- in lieu thereof.

In claim 10, line 1, after "claim" delete "2" and insert --1-- in lieu thereof.

In claim 7, column 104, line 1, delete "(2R,4S)" and insert --(2S,4R)-- in lieu thereof.

UNITED STATES PATENT AND TRADEMARK OFFICE
CERTIFICATE OF CORRECTION

PATENT NO. : 5,310,743

DATED : May 10, 1994

INVENTOR(S) : Walter Schilling, Silvio Ofner and Siem J. Veenstra

It is certified that error appears in the above-indentified patent and that said Letters Patent is hereby corrected as shown below:

In claim 7, column 104, line 3, after "3,5-" delete "dichlorobenzoyl" and insert -- dimethylbenzoyl-- in lieu thereof.

In claim 10, column 104, line 25, after "quinolin-" delete "2" and insert --3-- in lieu thereof.

In claim 10, column 104, line 31, after "quinolin-" delete "2" and insert --3-- in lieu thereof.

In claim 10, column 104, line 47, after "qionolin-" delete "2" and insert --3-- in lieu thereof.

Signed and Sealed this

Twenty-seventh Day of September, 1994

Attest:

BRUCE LEHMAN

*Attesting Officer*  *Commissioner of Patents and Trademarks*